(12) United States Patent
Kostrzewski

(10) Patent No.: US 10,765,438 B2
(45) Date of Patent: Sep. 8, 2020

(54) ANTI-SKID SURGICAL INSTRUMENT FOR USE IN PREPARING HOLES IN BONE TISSUE

(71) Applicant: KB Medical SA, Lausanne (CH)

(72) Inventor: Szymon Kostrzewski, Lausanne (CH)

( * ) Notice: Subject to any disclaimer, the term of this patent is extended or adjusted under 35 U.S.C. 154(b) by 685 days.

(21) Appl. No.: 15/405,743

(22) Filed: Jan. 13, 2017

(65) Prior Publication Data

US 2017/0224358 A1 Aug. 10, 2017

Related U.S. Application Data

(63) Continuation-in-part of application No. 14/799,170, filed on Jul. 14, 2015, now Pat. No. 10,357,257.

(60) Provisional application No. 62/395,795, filed on Sep. 16, 2016, provisional application No. 62/278,313, (Continued)

(51) Int. Cl.
*A61B 17/16* (2006.01)
*A61B 34/30* (2016.01)
*A61B 17/17* (2006.01)
*A61C 3/02* (2006.01)
(Continued)

(52) U.S. Cl.
CPC ........ *A61B 17/1615* (2013.01); *A61B 17/162* (2013.01); *A61B 17/1757* (2013.01); *A61B 34/20* (2016.02); *A61B 34/30* (2016.02); *A61C 3/02* (2013.01); *A61B 17/1671* (2013.01); *A61B 2017/1602* (2013.01); *A61B 2090/035* (2016.02); *A61B 2090/062* (2016.02)

(58) Field of Classification Search
CPC ............ A61B 17/1615; A61B 17/1671; A61B 17/162; A61B 17/1622; A61B 17/1624; A61B 17/17; A61B 17/1703; A61B 34/20
See application file for complete search history.

(56) References Cited

U.S. PATENT DOCUMENTS

| | | | |
|---|---|---|---|
| 4,150,293 A | 4/1979 | Franke | |
| 4,710,075 A | 12/1987 | Davison | |
| 5,246,010 A | 9/1993 | Gazzara et al. | |

(Continued)

FOREIGN PATENT DOCUMENTS

| | | | |
|---|---|---|---|
| CN | 102085110 A | 6/2011 | |
| CN | 103767759 A | 5/2014 | |

(Continued)

OTHER PUBLICATIONS

International Search Report, PCT/EP2015/066057, dated Oct. 22, 2015, 5 pages.
(Continued)

*Primary Examiner* — Anu Ramana

(57) ABSTRACT

Described herein is an anti-skid surgical instrument for use in preparing holes in bone tissue. The disclosed surgical instrument provides the ability to prepare a precise hole in bone tissue during surgery (e.g., spinal surgeries and pedicle screw placement, intramedullary screw placement). The disclosed surgical instrument accomplishes precise hole placement regardless of whether the angle between the drill axis and surface of the bone tissue is perpendicular. The disclosed technology includes a flat drilling surface which is perpendicular to the surface of the body of the surgical instrument. This reduces the likelihood of the surgical instrument skidding on the surface of the bone tissue and thereby increases the precision of the hole.

17 Claims, 40 Drawing Sheets

Related U.S. Application Data filed on Jan. 13, 2016, provisional application No. 62/024,402, filed on Jul. 14, 2014.

(51) Int. Cl.
  *A61B 34/20* (2016.01)
  *A61B 90/00* (2016.01)

(56) References Cited

U.S. PATENT DOCUMENTS

| | | | |
|---|---|---|---|
| 5,269,785 A * | 12/1993 | Bonutti | A61B 10/025 606/167 |
| 5,598,453 A | 1/1997 | Baba et al. | |
| 5,599,145 A * | 2/1997 | Reinauer | B23B 51/00 408/229 |
| 5,772,594 A | 6/1998 | Barrick | |
| 5,941,706 A | 8/1999 | Ura | |
| 5,987,960 A | 11/1999 | Messner et al. | |
| 6,031,888 A | 2/2000 | Ivan et al. | |
| 6,144,875 A | 11/2000 | Schweikard et al. | |
| 6,203,196 B1 | 3/2001 | Meyer et al. | |
| 6,306,126 B1 | 10/2001 | Montezuma | |
| 6,314,311 B1 | 11/2001 | Williams et al. | |
| 6,320,929 B1 | 11/2001 | Von Der Haar | |
| 6,477,400 B1 | 11/2002 | Barrick | |
| 6,484,049 B1 | 11/2002 | Seeley et al. | |
| 6,487,267 B1 | 11/2002 | Wolter | |
| 6,490,475 B1 | 12/2002 | Seeley et al. | |
| 6,501,981 B1 | 12/2002 | Schweikard et al. | |
| 6,535,756 B1 | 3/2003 | Simon et al. | |
| 6,614,453 B1 | 9/2003 | Suri et al. | |
| 6,614,871 B1 | 9/2003 | Kobiki et al. | |
| 6,619,840 B2 | 9/2003 | Rasche et al. | |
| 6,666,579 B2 | 12/2003 | Jensen | |
| 6,757,068 B2 | 6/2004 | Foxlin | |
| 6,782,287 B2 | 8/2004 | Grzeszczuk et al. | |
| 6,856,826 B2 | 2/2005 | Seeley et al. | |
| 6,856,827 B2 | 2/2005 | Seeley et al. | |
| 6,920,347 B2 | 7/2005 | Simon et al. | |
| 6,922,632 B2 | 7/2005 | Foxlin | |
| 6,988,009 B2 | 1/2006 | Grimm et al. | |
| 6,996,487 B2 | 2/2006 | Jutras et al. | |
| 7,016,457 B1 | 3/2006 | Senzig et al. | |
| 7,043,961 B2 | 5/2006 | Pandey et al. | |
| 7,048,477 B2 | 5/2006 | Abrams | |
| 7,062,006 B1 | 6/2006 | Pelc et al. | |
| 7,063,705 B2 | 6/2006 | Young et al. | |
| 7,072,707 B2 | 7/2006 | Galloway, Jr. et al. | |
| 7,099,428 B2 | 8/2006 | Clinthorne et al. | |
| 7,108,421 B2 | 9/2006 | Gregerson et al. | |
| 7,130,676 B2 | 10/2006 | Barrick | |
| 7,139,418 B2 | 11/2006 | Abovitz et al. | |
| 7,194,120 B2 | 3/2007 | Wicker et al. | |
| 7,197,107 B2 | 3/2007 | Arai et al. | |
| 7,231,014 B2 | 6/2007 | Levy | |
| 7,231,063 B2 | 6/2007 | Naimark et al. | |
| 7,301,648 B2 | 11/2007 | Foxlin | |
| 7,313,430 B2 | 12/2007 | Urquhart et al. | |
| 7,318,805 B2 | 1/2008 | Schweikard et al. | |
| 7,324,623 B2 | 1/2008 | Heuscher et al. | |
| 7,327,865 B2 | 2/2008 | Fu et al. | |
| 7,460,637 B2 | 12/2008 | Clinthorne et al. | |
| 7,493,153 B2 | 2/2009 | Ahmed et al. | |
| 7,505,617 B2 | 3/2009 | Fu et al. | |
| 7,623,902 B2 | 11/2009 | Pacheco | |
| 7,643,862 B2 | 1/2010 | Schoenefeld | |
| 7,661,881 B2 | 2/2010 | Gregerson et al. | |
| 7,683,331 B2 | 3/2010 | Chang | |
| 7,683,332 B2 | 3/2010 | Chang | |
| 7,702,379 B2 | 4/2010 | Avinash et al. | |
| 7,702,477 B2 | 4/2010 | Tuemmler et al. | |
| 7,711,083 B2 | 5/2010 | Heigl et al. | |
| 7,725,253 B2 | 5/2010 | Foxlin | |
| 7,726,171 B2 | 6/2010 | Langlotz et al. | |
| 7,760,849 B2 | 7/2010 | Zhang | |
| 7,796,728 B2 | 9/2010 | Bergfjord | |
| 7,813,838 B2 | 10/2010 | Sommer | |
| 7,835,778 B2 | 11/2010 | Foley et al. | |
| 7,835,784 B2 | 11/2010 | Mire et al. | |
| 7,840,256 B2 | 11/2010 | Lakin et al. | |
| 7,844,320 B2 | 11/2010 | Shahidi | |
| 7,853,305 B2 | 12/2010 | Simon et al. | |
| 7,853,313 B2 | 12/2010 | Thompson | |
| 7,900,524 B2 | 3/2011 | Calloway et al. | |
| 7,940,999 B2 | 5/2011 | Liao et al. | |
| 7,945,012 B2 | 5/2011 | Ye et al. | |
| 7,945,021 B2 | 5/2011 | Shapiro et al. | |
| 8,019,045 B2 | 9/2011 | Kato | |
| 8,021,310 B2 | 9/2011 | Sanborn et al. | |
| 8,052,688 B2 | 11/2011 | Wolf, II | |
| 8,086,299 B2 | 12/2011 | Adler et al. | |
| 8,098,914 B2 | 1/2012 | Liao et al. | |
| 8,100,950 B2 | 1/2012 | St. Clair et al. | |
| 8,116,430 B1 | 2/2012 | Shapiro et al. | |
| 8,121,249 B2 | 2/2012 | Wang et al. | |
| 8,150,494 B2 | 4/2012 | Simon et al. | |
| 8,208,708 B2 | 6/2012 | Homan et al. | |
| 8,224,024 B2 | 7/2012 | Foxlin et al. | |
| 8,311,611 B2 | 11/2012 | Csavoy et al. | |
| 8,335,557 B2 | 12/2012 | Maschke | |
| 8,358,818 B2 | 1/2013 | Miga et al. | |
| 8,379,791 B2 | 2/2013 | Forthmann et al. | |
| 8,386,019 B2 | 2/2013 | Camus et al. | |
| 8,394,099 B2 | 3/2013 | Patwardhan | |
| 8,462,911 B2 | 6/2013 | Vesel et al. | |
| 8,526,700 B2 | 9/2013 | Isaacs | |
| 8,541,970 B2 | 9/2013 | Nowlin et al. | |
| 8,560,118 B2 | 10/2013 | Greer et al. | |
| 8,597,198 B2 | 12/2013 | Sanborn et al. | |
| 8,611,985 B2 | 12/2013 | Lavallee et al. | |
| 8,630,389 B2 | 1/2014 | Kato | |
| 8,634,897 B2 | 1/2014 | Simon et al. | |
| 8,660,635 B2 | 2/2014 | Simon et al. | |
| 8,678,647 B2 | 3/2014 | Gregerson et al. | |
| 8,696,458 B2 | 4/2014 | Foxlin et al. | |
| 8,706,185 B2 | 4/2014 | Foley et al. | |
| 8,709,045 B1 | 4/2014 | Folsom | |
| 8,727,618 B2 | 5/2014 | Maschke et al. | |
| 8,738,115 B2 | 5/2014 | Amberg et al. | |
| 8,740,882 B2 | 6/2014 | Jun et al. | |
| 8,781,186 B2 | 7/2014 | Clements et al. | |
| 8,781,630 B2 | 7/2014 | Banks et al. | |
| 8,787,520 B2 | 7/2014 | Baba | |
| 8,792,704 B2 | 7/2014 | Isaacs | |
| 8,798,231 B2 | 8/2014 | Notohara et al. | |
| 8,812,077 B2 | 8/2014 | Dempsey | |
| 8,814,793 B2 | 8/2014 | Brabrand | |
| 8,818,105 B2 | 8/2014 | Myronenko et al. | |
| 8,821,511 B2 | 9/2014 | Von Jako et al. | |
| 8,867,703 B2 | 10/2014 | Shapiro et al. | |
| 8,888,821 B2 | 11/2014 | Rezach et al. | |
| 8,964,934 B2 | 2/2015 | Ein-Gal | |
| 8,992,580 B2 | 3/2015 | Bar et al. | |
| 8,996,169 B2 | 3/2015 | Lightcap et al. | |
| 9,001,963 B2 | 4/2015 | Sowards-Emmerd et al. | |
| 9,002,076 B2 | 4/2015 | Khadem et al. | |
| 9,044,190 B2 | 6/2015 | Rubner et al. | |
| 9,107,683 B2 | 8/2015 | Hourtash et al. | |
| 9,113,916 B2 * | 8/2015 | Lozier | A61B 17/1615 |
| 9,125,556 B2 | 9/2015 | Zehavi et al. | |
| 9,125,680 B2 | 9/2015 | Kostrzewski et al. | |
| 9,131,986 B2 | 9/2015 | Greer et al. | |
| 9,215,968 B2 | 12/2015 | Schostek et al. | |
| 9,241,771 B2 | 1/2016 | Kostrzewski et al. | |
| 9,283,048 B2 | 3/2016 | Kostrzewski et al. | |
| 9,308,050 B2 | 4/2016 | Kostrzewski et al. | |
| 9,380,984 B2 | 7/2016 | Li et al. | |
| 9,393,039 B2 | 7/2016 | Lechner et al. | |
| 9,398,886 B2 | 7/2016 | Gregerson et al. | |
| 9,398,890 B2 | 7/2016 | Dong et al. | |
| 9,414,859 B2 | 8/2016 | Ballard et al. | |
| 9,420,975 B2 | 8/2016 | Gutfleisch et al. | |
| 9,492,235 B2 | 11/2016 | Hourtash et al. | |
| 9,592,096 B2 | 3/2017 | Maillet et al. | |

(56) References Cited

U.S. PATENT DOCUMENTS

| | | |
|---|---|---|
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2004/0076259 A1 | 4/2004 | Jensen et al. |
| 2004/0265082 A1 | 12/2004 | Abrams |
| 2006/0184396 A1 | 8/2006 | Dennis et al. |
| 2006/0291612 A1 | 12/2006 | Nishide et al. |
| 2007/0038059 A1 | 2/2007 | Sheffer et al. |
| 2007/0073133 A1 | 3/2007 | Schoenefeld |
| 2007/0239187 A1 | 10/2007 | Brunnett |
| 2007/0293867 A1* | 12/2007 | Anitua ............... A61B 17/1615 606/80 |
| 2008/0004523 A1 | 1/2008 | Jensen |
| 2008/0013809 A1 | 1/2008 | Zhu et al. |
| 2008/0082109 A1 | 4/2008 | Moll et al. |
| 2008/0108991 A1 | 5/2008 | Von Jako |
| 2008/0144906 A1 | 6/2008 | Allred et al. |
| 2008/0161680 A1 | 7/2008 | Von Jako et al. |
| 2008/0235052 A1 | 9/2008 | Node-Langlois et al. |
| 2008/0269596 A1 | 10/2008 | Revie et al. |
| 2008/0287781 A1 | 11/2008 | Revie et al. |
| 2008/0300477 A1 | 12/2008 | Lloyd et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0024129 A1 | 1/2009 | Gordon et al. |
| 2009/0185655 A1 | 7/2009 | Koken et al. |
| 2009/0198121 A1 | 8/2009 | Hoheisel |
| 2009/0287222 A1 | 11/2009 | Lee et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0145341 A1 | 6/2010 | Ranck et al. |
| 2010/0228117 A1 | 9/2010 | Hartmann |
| 2010/0274120 A1 | 10/2010 | Heuscher |
| 2011/0098553 A1 | 4/2011 | Robbins et al. |
| 2011/0282189 A1 | 11/2011 | Graumann |
| 2011/0286573 A1 | 11/2011 | Schretter et al. |
| 2012/0035507 A1 | 2/2012 | George et al. |
| 2012/0051498 A1 | 3/2012 | Koishi |
| 2012/0143084 A1 | 6/2012 | Shoham |
| 2012/0226145 A1 | 9/2012 | Chang et al. |
| 2012/0235909 A1 | 9/2012 | Birkenbach et al. |
| 2012/0294498 A1 | 11/2012 | Popovic |
| 2012/0330315 A1 | 12/2012 | Ranck et al. |
| 2013/0016889 A1 | 1/2013 | Myronenko et al. |
| 2013/0060146 A1 | 3/2013 | Yang et al. |
| 2013/0094742 A1 | 4/2013 | Feilkas |
| 2013/0113791 A1 | 5/2013 | Isaacs et al. |
| 2013/0165937 A1 | 6/2013 | Patwardhan |
| 2013/0281821 A1 | 10/2013 | Liu et al. |
| 2013/0307955 A1 | 11/2013 | Deitz et al. |
| 2013/0342578 A1 | 12/2013 | Isaacs |
| 2013/0345757 A1 | 12/2013 | Stad |
| 2014/0046132 A1 | 2/2014 | Hoeg et al. |
| 2014/0049629 A1 | 2/2014 | Siewerdsen et al. |
| 2014/0080086 A1 | 3/2014 | Chen |
| 2014/0096369 A1 | 4/2014 | Matsumoto et al. |
| 2014/0121676 A1 | 5/2014 | Kostrzewski et al. |
| 2014/0135796 A1 | 5/2014 | Simon et al. |
| 2014/0130810 A1 | 8/2014 | Azizian et al. |
| 2014/0221819 A1 | 8/2014 | Sarment |
| 2014/0234804 A1 | 8/2014 | Huang et al. |
| 2014/0371577 A1 | 12/2014 | Mallet et al. |
| 2015/0039034 A1 | 2/2015 | Frankel et al. |
| 2015/0085970 A1 | 3/2015 | Bouhnik et al. |
| 2015/0100066 A1 | 4/2015 | Kostrzewski et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0305817 A1 | 10/2015 | Kostrzewski |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0008011 A1 | 1/2016 | Kostrzewski |
| 2016/0106442 A1 | 4/2016 | Guo et al. |
| 2016/0151120 A1 | 6/2016 | Kostrzewski et al. |
| 2016/0166329 A1 | 6/2016 | Langan et al. |
| 2016/0235480 A1 | 8/2016 | Scholl et al. |
| 2016/0235492 A1 | 8/2016 | Morard et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

FOREIGN PATENT DOCUMENTS

| | | |
|---|---|---|
| EP | 2698115 A1 | 2/2014 |
| WO | WO-1999/020196 A1 | 4/1999 |
| WO | WO-2007/055441 A1 | 5/2007 |
| WO | 2011147831 A1 | 12/2011 |
| WO | WO-2012/131660 A1 | 10/2012 |

OTHER PUBLICATIONS

Written Opinion, PCT/EP2015/066057, dated Oct. 22, 2015, 7 pages.

* cited by examiner

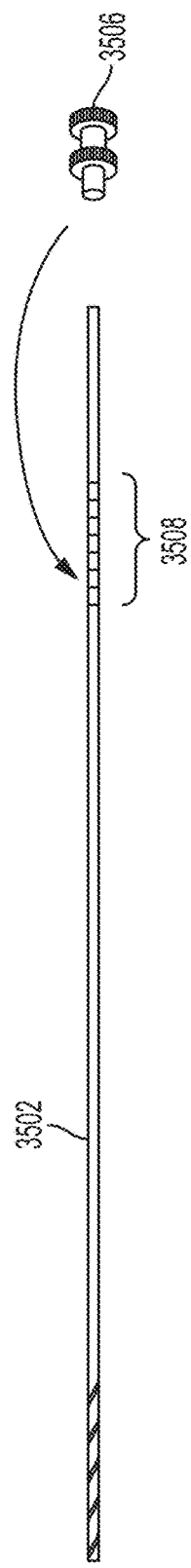
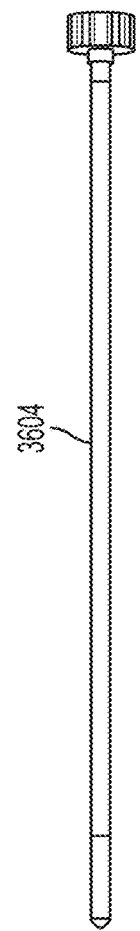
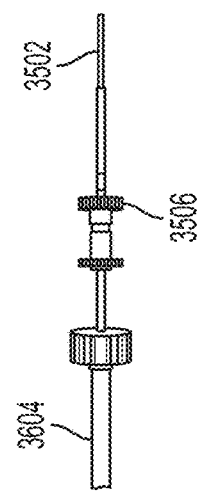
FIG. 35A
FIG. 35B
FIG. 35C

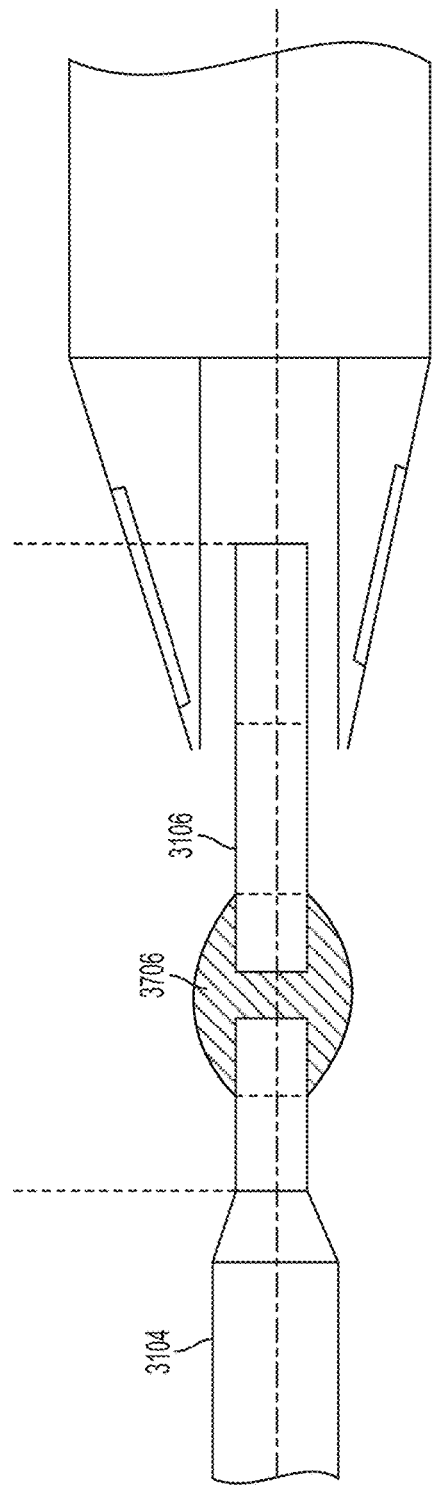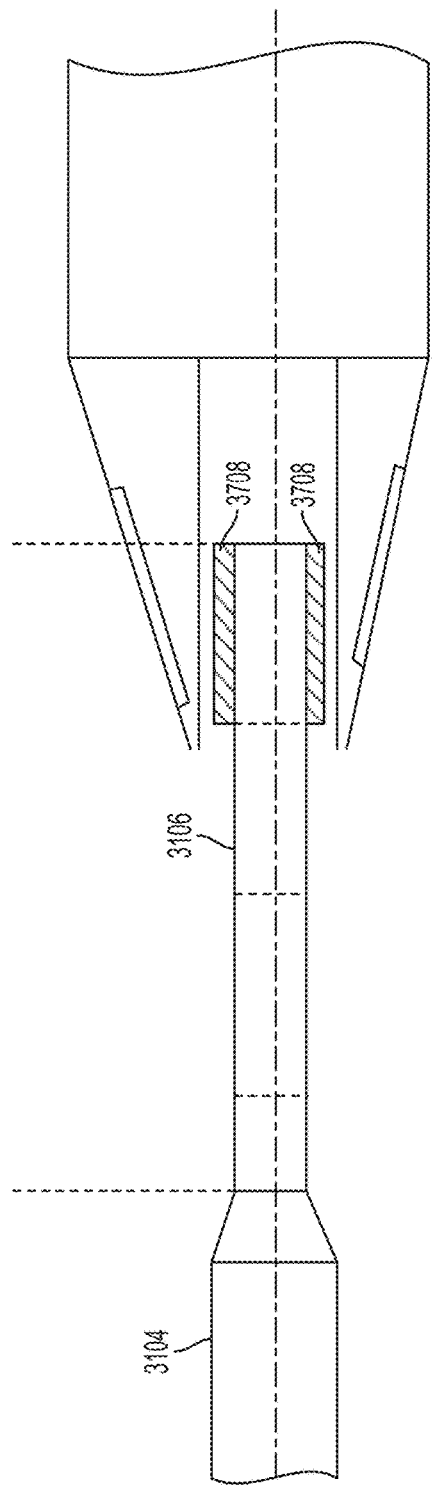
FIG. 37A
FIG. 37B

ANTI-SKID SURGICAL INSTRUMENT FOR USE IN PREPARING HOLES IN BONE TISSUE

RELATED APPLICATIONS

This application claims priority to U.S. Provisional Patent Application No. 62/278,313, filed Jan. 13, 2016, entitled "Anti-Skid Surgical Instrument for use in Preparing Holes in Bone Tissue" and U.S. Provisional Patent Application No. 62/395,795, filed Sep. 16, 2016, entitled "Anti-Skid Surgical Instrument for use in Preparing Holes in Bone Tissue," and is a Continuation-in-Part of U.S. patent application Ser. No. 14/799,170, filed Jul. 14, 2015, entitled "Anti-Skid Surgical Instrument for use in Preparing Holes in Bone Tissue," which claims priority to U.S. Provisional Patent Application No. 62/024,402, filed Jul. 14, 2014, entitled "Anti-Skid Surgical Instrument for use in Preparing Holes in Bone Tissue," the contents of each of which is incorporated by reference herein in its entirety.

FIELD OF THE INVENTION

The present invention relates to an anti-skid surgical instrument for use in preparing holes in bone tissue during an operation.

BACKGROUND OF THE INVENTION

Spinal surgeries often require precision drilling and placement of screws or other implements in bone tissue. Catastrophic damage or death may result from improper drilling or maneuvering of the body during spinal surgery due to the proximity of the spinal cord and arteries. Further, accurate placement is typically necessary for a successful outcome. For example, spinal fusion is typically augmented by stabilizing the vertebrae with fixation devices, such as metallic screws, rods, and plates, to facilitate bone fusion. In spinal fusion, as well as other surgeries, the accuracy with which the screws are placed in the bone has a direct effect on the outcome of the procedure. The less motion there is between the two bones trying to heal, the higher the change the bones will successfully fuse. The use of fixation devices has increased the success rate of spinal fusion procedures considerably.

Such procedures rely strongly on the expertise of the surgeon, and there is significant variation in success rate among different surgeons. A number of navigational and verification approaches have been developed. However, screw misplacement is still a common problem in such surgical procedures. Screws may be misaligned due to inaccurate holes drilled prior to inserting the screw. The angle of the tip of the drill may cause the drill bit to skid as the tip contacts the bone tissue, thereby causing the hole to be drilled along an incorrect trajectory. Typically, unless a bone drill is driven at 90 degrees to the bone surface there is a tendency for the drill bit to skid over the bone surface thereby placing the hole inappropriately. Thus, there is a need for an anti-skid surgical instrument for preparing holes in a patient's bone while minimizing the risk of the instrument skidding upon contact of the surgical instrument with the bone.

SUMMARY OF THE INVENTION

Described herein is an anti-skid surgical instrument for use in preparing holes in bone tissue. The disclosed surgical instrument provides the ability to prepare a precise hole in bone tissue during surgery (e.g., spinal surgeries and pedicle screw placement, intramedullary screw placement). The disclosed surgical instrument accomplishes precise hole placement regardless of whether the angle between the drill axis and surface of the bone tissue is perpendicular. The disclosed technology includes a flat drilling surface which is perpendicular to the surface of the body of the surgical instrument. This reduces the likelihood of the surgical instrument skidding on the surface of the bone tissue and thereby increases the precision of the hole.

In one aspect, the disclosed technology includes a robotic surgical system for preparing a hole in bone tissue of a patient during surgery, including: a robotic arm having an end effector with a surgical instrument guide attached thereto, the surgical instrument guide arranged to hold and/or restrict movement of an anti-skid surgical instrument therethrough; and the anti-skid surgical instrument having an elongate structure comprising: a mill head at the end of the elongate structure for removing bone tissue with reduced skidding (e.g., unintentional lateral movement of the surgical instrument) of the surgical instrument upon contact of the anti-ski surgical instrument with the bone tissue, wherein the mill head has a flat end substantially perpendicular to a longitudinal axis of the elongate structure, and one or more side-cutting flutes about the longitudinal axis of the elongate structure for cutting into bone tissue; a spike extending from the mill head; a shank for connection to a drill; and a shaft between the mill head and the shank, the shaft having one or more drill flutes (e.g., non-cutting flutes) for evacuating removed bone tissue.

In certain embodiments, the mill head comprises a concave face from which the spike extends.

In certain embodiments, the instrument includes a compliant part that absorbs energy from the mill head.

In certain embodiments, the instrument includes a cannulation in the surgical instrument.

In certain embodiments, the cannulation comprises a hole in the end of the elongate structure (e.g., a tip of the surgical instrument).

In certain embodiments, the compliant part comprises at least one of an elastic material, rubber, a bellow, and a universal joint.

In certain embodiments, the compliant part connects a first portion of the anti-ski surgical instrument to a second portion of the anti-skid surgical instrument.

In certain embodiments, the first portion comprises the mill head and a portion of the shaft and the second portion comprises the shank and a portion of the shaft.

In certain embodiments, the compliant part covers at least a portion of the shank.

In certain embodiments, the compliant part covers at least part of the shaft.

In certain embodiments, the compliant part covers at least part of the shaft and the shank.

In certain embodiments, a depth control.

In certain embodiments, the depth control comprises at least one of one or more markings and one or more colors for depicting depth of insertion.

In certain embodiments, the depth control comprises a first portion indicating when to start rotation of the anti-skid surgical instrument and a second portion indicating when to at least one of stop rotation and stop depth penetration of the anti-ski surgical instrument.

In certain embodiments, the depth control comprises a depth stop that adjustably attached to the anti-skid surgical instrument such that the depth of penetration of the anti-skid surgical instrument changes as a position of the depth stop is changed.

In certain embodiments, the shaft comprises one or more notches and the depth control engages at least one of the one or more notches when attached to the anti-skid surgical instrument.

In certain embodiments, the system comprises a tool support located between the shaft and the shank, wherein: the tool support is shaped and sized to slide through the surgical instrument guide along the axis defined by the guide, and a diameter of the tool support is greater than a diameter of the shank.

In certain embodiments, the end of the mill head has one or more end cutting flutes for cutting axially into the bone tissue.

In certain embodiments, the one or more drill flutes comprise at least two, three, four, six, eight, ten, or twenty flutes.

In certain embodiments, one or more side cutting flutes comprise at least two, three, four, six, eight, ten, or twenty flutes.

In certain embodiments, a longitudinal length of the shaft is greater than a longitudinal length of the mill head.

In certain embodiments, a longitudinal length of the shaft is greater than a longitudinal length of the shank.

In certain embodiments, the one or more drill flutes have a higher twist rate (i.e., larger flute angle) than the one or more side cutting flutes or the one or more drill flutes have a lower twist rate (i.e., smaller flute angle) than the one or more side cutting flutes.

In certain embodiments, the one or more drill flutes have a different twist rate (i.e., different flute angle) than the one or more side cutting flutes.

In certain embodiments, the surgery is spinal, orthopedic, dental, ear, nose, or throat surgery.

In certain embodiments, a manipulator is attached to the robotic arm or molded into the robotic arm.

In another aspect, the disclosed technology includes a robotic surgical system for preparing a hole in bone tissue of a patient during surgery, including: a robotic arm having an end effector with a surgical instrument guide attached thereto, the surgical instrument guide arranged to hold and/or restrict movement of an anti-skid surgical instrument therethrough; and the anti-skid surgical instrument having an elongate structure comprising: a mill head at the end of the elongate structure for removing bone tissue with reduced skidding (e.g., unintentional lateral movement of the surgical instrument) of the surgical instrument upon contact of the anti-ski surgical instrument with the bone tissue, wherein the mill head has a concave end substantially perpendicular to a longitudinal axis of the elongate structure, and one or more side-cutting flutes about the longitudinal axis of the elongate structure for cutting into bone tissue; a shank for connection to a drill; and a shaft between the mill head and the shank, the shaft having one or more drill flutes (e.g., non-cutting flutes) for evacuating removed bone tissue.

In certain embodiments, the instrument includes a spike extending from the concave end of the mill head.

In certain embodiments, the instrument includes a compliant part that absorbs energy from the mill head.

In certain embodiments, the instrument includes a cannulation in the surgical instrument.

In certain embodiments, the cannulation comprises a hole in the end of the elongate structure (e.g., a tip of the surgical instrument).

In certain embodiments, the compliant part comprises at least one of an elastic material, rubber, a bellow, and a universal joint.

In certain embodiments, the compliant part connects a first portion of the anti-ski surgical instrument to a second portion of the anti-skid surgical instrument.

In certain embodiments, the first portion comprises the mill head and a portion of the shaft and the second portion comprises the shank and a portion of the shaft.

In certain embodiments, the compliant part covers at least a portion of the shank.

In certain embodiments, the compliant part covers at least part of the shaft.

In certain embodiments, the compliant part covers at least part of the shaft and the shank.

In certain embodiments, a depth control.

In certain embodiments, the depth control comprises at least one of one or more markings and one or more colors for depicting depth of insertion.

In certain embodiments, the depth control comprises a first portion indicating when to start rotation of the anti-skid surgical instrument and a second portion indicating when to at least one of stop rotation and stop depth penetration of the anti-ski surgical instrument.

In certain embodiments, the depth control comprises a depth stop that adjustably attached to the anti-skid surgical instrument such that the depth of penetration of the anti-skid surgical instrument changes as a position of the depth stop is changed.

In certain embodiments, the shaft comprises one or more notches and the depth control engages at least one of the one or more notches when attached to the anti-skid surgical instrument.

In certain embodiments, the system comprises a tool support located between the shaft and the shank, wherein: the tool support is shaped and sized to slide through the surgical instrument guide along the axis defined by the guide, and a diameter of the tool support is greater than a diameter of the shank.

In certain embodiments, the end of the mill head has one or more end cutting flutes for cutting axially into the bone tissue.

In certain embodiments, the one or more drill flutes comprise at least two, three, four, six, eight, ten, or twenty flutes.

In certain embodiments, one or more side cutting flutes comprise at least two, three, four, six, eight, ten, or twenty flutes.

In certain embodiments, a longitudinal length of the shaft is greater than a longitudinal length of the mill head.

In certain embodiments, a longitudinal length of the shaft is greater than a longitudinal length of the shank.

In certain embodiments, the one or more drill flutes have a higher twist rate (i.e., larger flute angle) than the one or more side cutting flutes or the one or more drill flutes have a lower twist rate (i.e., smaller flute angle) than the one or more side cutting flutes.

In certain embodiments, the one or more drill flutes have a different twist rate (i.e., different flute angle) than the one or more side cutting flutes.

In certain embodiments, the surgery is spinal, orthopedic, dental, ear, nose, or throat surgery.

In certain embodiments, a manipulator is attached to the robotic arm or molded into the robotic arm.

In another aspect, the disclosed technology includes a robotic surgical system for preparing a hole in bone tissue of a patient during surgery, including: a robotic arm having an end effector with a surgical instrument guide attached thereto, the surgical instrument guide arranged to hold and/or restrict movement of an anti-skid surgical instrument therethrough; and the anti-skid surgical instrument having an elongate structure comprising: a mill head at the end of the elongate structure for removing bone tissue with reduced skidding (e.g., unintentional lateral movement of the surgical instrument) of the surgical instrument upon contact of the anti-ski surgical instrument with the bone tissue, wherein the mill head has a flat end substantially perpendicular to a longitudinal axis of the elongate structure, and one or more side-cutting flutes about the longitudinal axis of the elongate structure for cutting into bone tissue; a shank for connection to a drill; a shaft between the mill head and the shank, the shaft having one or more drill flutes (e.g., non-cutting flutes) for evacuating removed bone tissue; and a cannulation in the surgical instrument.

In certain embodiments, the cannulation comprises a hole in the end of the elongate structure (e.g., a tip of the surgical instrument).

In certain embodiments, the instrument includes a compliant part that absorbs energy from the mill head.

In certain embodiments, the instrument includes a spike extending from the mill head.

In certain embodiments, the mill head includes a concave face (e.g., from which the spike extends).

In certain embodiments, the compliant part comprises at least one of an elastic material, rubber, a bellow, and a universal joint.

In certain embodiments, the compliant part connects a first portion of the anti-ski surgical instrument to a second portion of the anti-skid surgical instrument.

In certain embodiments, the first portion comprises the mill head and a portion of the shaft and the second portion comprises the shank and a portion of the shaft.

In certain embodiments, the compliant part covers at least a portion of the shank.

In certain embodiments, the compliant part covers at least part of the shaft.

In certain embodiments, the compliant part covers at least part of the shaft and the shank.

In certain embodiments, a depth control.

In certain embodiments, the depth control comprises at least one of one or more markings and one or more colors for depicting depth of insertion.

In certain embodiments, the depth control comprises a first portion indicating when to start rotation of the anti-skid surgical instrument and a second portion indicating when to at least one of stop rotation and stop depth penetration of the anti-ski surgical instrument.

In certain embodiments, the depth control comprises a depth stop that adjustably attached to the anti-skid surgical instrument such that the depth of penetration of the anti-skid surgical instrument changes as a position of the depth stop is changed.

In certain embodiments, the shaft comprises one or more notches and the depth control engages at least one of the one or more notches when attached to the anti-skid surgical instrument.

In certain embodiments, the system comprises a tool support located between the shaft and the shank, wherein: the tool support is shaped and sized to slide through the surgical instrument guide along the axis defined by the guide, and a diameter of the tool support is greater than a diameter of the shank.

In certain embodiments, the end of the mill head has one or more end cutting flutes for cutting axially into the bone tissue.

In certain embodiments, the one or more drill flutes comprise at least two, three, four, six, eight, ten, or twenty flutes.

In certain embodiments, one or more side cutting flutes comprise at least two, three, four, six, eight, ten, or twenty flutes.

In certain embodiments, a longitudinal length of the shaft is greater than a longitudinal length of the mill head.

In certain embodiments, a longitudinal length of the shaft is greater than a longitudinal length of the shank.

In certain embodiments, the one or more drill flutes have a higher twist rate (i.e., larger flute angle) than the one or more side cutting flutes or the one or more drill flutes have a lower twist rate (i.e., smaller flute angle) than the one or more side cutting flutes.

In certain embodiments, the one or more drill flutes have a different twist rate (i.e., different flute angle) than the one or more side cutting flutes.

In certain embodiments, the surgery is spinal, orthopedic, dental, ear, nose, or throat surgery.

In certain embodiments, a manipulator is attached to the robotic arm or molded into the robotic arm.

In another aspect, the disclosed technology includes a robotic surgical system for preparing a hole in bone tissue of a patient during surgery, comprising:

a robotic arm having an end effector with a surgical instrument guide attached thereto, the surgical instrument guide arranged to hold and/or restrict movement of an anti-skid surgical instrument therethrough; and the anti-skid surgical instrument having an elongate structure comprising: a mill head at the end of the elongate structure for removing bone tissue with reduced skidding (e.g., unintentional lateral movement of the surgical instrument) of the surgical instrument upon contact of the anti-ski surgical instrument with the bone tissue, wherein the mill head has a flat end substantially perpendicular to a longitudinal axis of the elongate structure, and one or more side-cutting flutes about the longitudinal axis of the elongate structure for cutting into bone tissue; a shank for connection to a drill; a shaft between the mill head and the shank, the shaft having one or more drill flutes (e.g., non-cutting flutes) for evacuating removed bone tissue; and a compliant part that absorbs energy from the mill head.

In certain embodiments, the compliant part comprises at least one of an elastic material, rubber, a bellow, and a universal joint.

In certain embodiments, the compliant part connects a first portion of the anti-ski surgical instrument to a second portion of the anti-skid surgical instrument.

In certain embodiments, the first portion comprises the mill head and a portion of the shaft and the second portion comprises the shank and a portion of the shaft.

In certain embodiments, the compliant part covers at least a portion of the shank.

In certain embodiments, the compliant part covers at least part of the shaft.

In certain embodiments, the compliant part covers at least part of the shaft and the shank.

In certain embodiments, the instrument includes a cannulation in the surgical instrument.

In certain embodiments, the cannulation comprises a hole in the end of the elongate structure (e.g., a tip of the surgical instrument).

In certain embodiments, the instrument includes a spike extending from the mill head.

In certain embodiments, the mill head comprises a concave face (e.g., from which the spike extends).

In certain embodiments, the compliant part comprises at least one of an elastic material, rubber, a bellow, and a universal joint.

In certain embodiments, the compliant part connects a first portion of the anti-ski surgical instrument to a second portion of the anti-skid surgical instrument.

In certain embodiments, the first portion comprises the mill head and a portion of the shaft and the second portion comprises the shank and a portion of the shaft.

In certain embodiments, the compliant part covers at least a portion of the shank.

In certain embodiments, the compliant part covers at least part of the shaft.

In certain embodiments, the compliant part covers at least part of the shaft and the shank.

In certain embodiments, a depth control.

In certain embodiments, the depth control comprises at least one of one or more markings and one or more colors for depicting depth of insertion.

In certain embodiments, the depth control comprises a first portion indicating when to start rotation of the anti-skid surgical instrument and a second portion indicating when to at least one of stop rotation and stop depth penetration of the anti-ski surgical instrument.

In certain embodiments, the depth control comprises a depth stop that adjustably attached to the anti-skid surgical instrument such that the depth of penetration of the anti-skid surgical instrument changes as a position of the depth stop is changed.

In certain embodiments, the shaft comprises one or more notches and the depth control engages at least one of the one or more notches when attached to the anti-skid surgical instrument.

In certain embodiments, the system comprises a tool support located between the shaft and the shank, wherein: the tool support is shaped and sized to slide through the surgical instrument guide along the axis defined by the guide, and a diameter of the tool support is greater than a diameter of the shank.

In certain embodiments, the end of the mill head has one or more end cutting flutes for cutting axially into the bone tissue.

In certain embodiments, the one or more drill flutes comprise at least two, three, four, six, eight, ten, or twenty flutes.

In certain embodiments, one or more side cutting flutes comprise at least two, three, four, six, eight, ten, or twenty flutes.

In certain embodiments, a longitudinal length of the shaft is greater than a longitudinal length of the mill head.

In certain embodiments, a longitudinal length of the shaft is greater than a longitudinal length of the shank.

In certain embodiments, the one or more drill flutes have a higher twist rate (i.e., larger flute angle) than the one or more side cutting flutes or the one or more drill flutes have a lower twist rate (i.e., smaller flute angle) than the one or more side cutting flutes.

In certain embodiments, the one or more drill flutes have a different twist rate (i.e., different flute angle) than the one or more side cutting flutes.

In certain embodiments, the surgery is spinal, orthopedic, dental, ear, nose, or throat surgery.

In certain embodiments, a manipulator is attached to the robotic arm or molded into the robotic arm.

In one aspect, the disclosed technology includes a robotic surgical system for preparing a hole in bone tissue of a patient during surgery, including: a robotic arm having an end effector with a surgical instrument guide attached thereto, the surgical instrument guide arranged to hold and/or restrict movement of an anti-skid surgical instrument therethrough; and the anti-skid surgical instrument having an elongate structure comprising: a mill head at the end of the elongate structure for removing bone tissue with reduced skidding (e.g., unintentional lateral movement of the surgical instrument) of the surgical instrument upon contact of the anti-ski surgical instrument with the bone tissue, wherein the mill head has a flat end substantially perpendicular to a longitudinal axis of the elongate structure, and one or more side-cutting flutes about the longitudinal axis of the elongate structure for cutting into bone tissue; a shank for connection to a drill; a shaft between the mill head and the shank, the shaft having one or more drill flutes (e.g., non-cutting flutes) for evacuating removed bone tissue; and a depth control.

In certain embodiments, the depth control comprises one or more markings.

In certain embodiments, the depth control comprises one or more colors for depicting depth of insertion.

In certain embodiments, the depth control comprises a first portion indicating when to start rotation of the anti-skid surgical instrument and a second portion indicating when to at least one of stop rotation and stop depth penetration of the anti-ski surgical instrument.

In certain embodiments, the depth control comprises a depth stop that adjustably attached to the anti-skid surgical instrument such that the depth of penetration of the anti-skid surgical instrument changes as a position of the depth stop is changed.

In certain embodiments, the shaft comprises one or more notches and the depth control engages at least one of the one or more notches when attached to the anti-skid surgical instrument.

In certain embodiments, the instrument includes a compliant part that absorbs energy from the mill head.

In certain embodiments, the instrument includes a cannulation in the surgical instrument.

In certain embodiments, the cannulation comprises a hole in the end of the elongate structure (e.g., a tip of the surgical instrument).

In certain embodiments, the instrument includes a spike extending from the mill head.

In certain embodiments, the mill head comprises a concave face (e.g., from which the spike extends).

In certain embodiments, the compliant part comprises at least one of an elastic material, rubber, a bellow, and a universal joint.

In certain embodiments, the compliant part connects a first portion of the anti-ski surgical instrument to a second portion of the anti-skid surgical instrument.

In certain embodiments, the first portion comprises the mill head and a portion of the shaft and the second portion comprises the shank and a portion of the shaft.

In certain embodiments, the compliant part covers at least a portion of the shank.

In certain embodiments, the compliant part covers at least part of the shaft.

In certain embodiments, the compliant part covers at least part of the shaft and the shank.

In certain embodiments, a depth control.

In certain embodiments, the depth control comprises at least one of one or more markings and one or more colors for depicting depth of insertion.

In certain embodiments, the depth control comprises a first portion indicating when to start rotation of the anti-skid surgical instrument and a second portion indicating when to at least one of stop rotation and stop depth penetration of the anti-ski surgical instrument.

In certain embodiments, the depth control comprises a depth stop that adjustably attached to the anti-skid surgical instrument such that the depth of penetration of the anti-skid surgical instrument changes as a position of the depth stop is changed.

In certain embodiments, the shaft comprises one or more notches and the depth control engages at least one of the one or more notches when attached to the anti-skid surgical instrument.

In certain embodiments, the system comprises a tool support located between the shaft and the shank, wherein: the tool support is shaped and sized to slide through the surgical instrument guide along the axis defined by the guide, and a diameter of the tool support is greater than a diameter of the shank.

In certain embodiments, the end of the mill head has one or more end cutting flutes for cutting axially into the bone tissue.

In certain embodiments, the one or more drill flutes comprise at least two, three, four, six, eight, ten, or twenty flutes.

In certain embodiments, one or more side cutting flutes comprise at least two, three, four, six, eight, ten, or twenty flutes.

In certain embodiments, a longitudinal length of the shaft is greater than a longitudinal length of the mill head.

In certain embodiments, a longitudinal length of the shaft is greater than a longitudinal length of the shank.

In certain embodiments, the one or more drill flutes have a higher twist rate (i.e., larger flute angle) than the one or more side cutting flutes or the one or more drill flutes have a lower twist rate (i.e., smaller flute angle) than the one or more side cutting flutes.

In certain embodiments, the one or more drill flutes have a different twist rate (i.e., different flute angle) than the one or more side cutting flutes.

In certain embodiments, the surgery is spinal, orthopedic, dental, ear, nose, or throat surgery.

In certain embodiments, a manipulator is attached to the robotic arm or molded into the robotic arm.

In another aspect, the disclosed technology includes an anti-skid surgical instrument for preparing a hole in bone tissue of a patient during surgery, the anti-skid surgical instrument having an elongate structure comprising: a mill head at the end of the elongate structure for removing bone tissue with reduced skidding (e.g., unintentional lateral movement of the surgical instrument) of the surgical instrument upon contact of the anti-ski surgical instrument with the bone tissue, wherein the mill head has a flat end substantially perpendicular to a longitudinal axis of the elongate structure, and one or more side-cutting flutes about the longitudinal axis of the elongate structure for cutting into bone tissue; a spike extending from the mill head; a shank for connection to a drill; and a shaft between the mill head and the shank, the shaft having one or more drill flutes (e.g., non-cutting flutes) for evacuating removed bone tissue.

In certain embodiments, the mill head comprises a concave face from which the spike extends.

In certain embodiments, the instrument includes a cannulation in the surgical instrument.

In certain embodiments, the cannulation comprises a hole in the end of the elongate structure (e.g., a tip of the surgical instrument).

In certain embodiments, the instrument includes a compliant part that absorbs energy from the mill head.

In certain embodiments, the compliant part comprises at least one of an elastic material, rubber, a bellow, and a universal joint.

In certain embodiments, the compliant part connects a first portion of the anti-ski surgical instrument to a second portion of the anti-skid surgical instrument.

In certain embodiments, the first portion comprises the mill head and a portion of the shaft and the second portion comprises the shank and a portion of the shaft.

In certain embodiments, the compliant part covers at least a portion of the shank.

In certain embodiments, the compliant part covers at least part of the shaft.

In certain embodiments, the compliant part covers at least part of the shaft and the shank.

In certain embodiments, the instrument includes a depth control.

In certain embodiments, the depth control comprises at least one of one or more markings and one or more colors for depicting depth of insertion.

In certain embodiments, the depth control comprises a first portion indicating when to start rotation of the anti-skid surgical instrument and a second portion indicating when to at least one of stop rotation and stop depth penetration of the anti-ski surgical instrument.

In certain embodiments, the depth control comprises a depth stop that adjustably attached to the anti-skid surgical instrument such that the depth of penetration of the anti-skid surgical instrument changes as a position of the depth stop is changed.

In certain embodiments, the shaft comprises one or more notches and the depth control engages at least one of the one or more notches when attached to the anti-skid surgical instrument.

In certain embodiments, the instrument includes a tool support located between the shaft and the shank, wherein: the tool support is shaped and sized to slide through the surgical instrument guide along the axis defined by the guide, and a diameter of the tool support is greater than a diameter of the shank.

In certain embodiments, the end of the mill head has one or more end cutting flutes for cutting axially into the bone tissue.

In certain embodiments, the one or more drill flutes comprise at least two, three, four, six, eight, ten, or twenty flutes.

In certain embodiments, one or more side cutting flutes comprise at least two, three, four, six, eight, ten, or twenty flutes.

In certain embodiments, a longitudinal length of the shaft is greater than a longitudinal length of the mill head.

In certain embodiments, a longitudinal length of the shaft is greater than a longitudinal length of the shank.

In certain embodiments, the one or more drill flutes have a higher twist rate (i.e., larger flute angle) than the one or more side cutting flutes or the one or more drill flutes have a lower twist rate (i.e., smaller flute angle) than the one or more side cutting flutes.

In certain embodiments, the one or more drill flutes have a different twist rate (i.e., different flute angle) than the one or more side cutting flutes.

In certain embodiments, the surgery is spinal, orthopedic, dental, ear, nose, or throat surgery.

In certain embodiments, a manipulator is attached to the robotic arm or molded into the robotic arm.

In certain embodiments, the disclosed technology includes an anti-skid surgical instrument for preparing a hole in bone tissue of a patient during surgery, the anti-skid surgical instrument having an elongate structure comprising: a mill head at the end of the elongate structure for removing bone tissue with reduced skidding (e.g., unintentional lateral movement of the surgical instrument) of the surgical instrument upon contact of the anti-ski surgical instrument with the bone tissue, wherein the mill head has a concave end substantially perpendicular to a longitudinal axis of the elongate structure, and one or more side-cutting flutes about the longitudinal axis of the elongate structure for cutting into bone tissue; a shank for connection to a drill; and a shaft between the mill head and the shank, the shaft having one or more drill flutes (e.g., non-cutting flutes) for evacuating removed bone tissue.

In certain embodiments, the instrument includes a spike extending from the concave end of the mill head.

In certain embodiments, the instrument includes a cannulation in the surgical instrument.

In certain embodiments, the cannulation comprises a hole in the end of the elongate structure (e.g., a tip of the surgical instrument).

In certain embodiments, the instrument includes a compliant part that absorbs energy from the mill head.

In certain embodiments, the compliant part comprises at least one of an elastic material, rubber, a bellow, and a universal joint.

In certain embodiments, the compliant part connects a first portion of the anti-ski surgical instrument to a second portion of the anti-skid surgical instrument.

In certain embodiments, the first portion comprises the mill head and a portion of the shaft and the second portion comprises the shank and a portion of the shaft.

In certain embodiments, the compliant part covers at least a portion of the shank.

In certain embodiments, the compliant part covers at least part of the shaft.

In certain embodiments, the compliant part covers at least part of the shaft and the shank.

In certain embodiments, the instrument includes a depth control.

In certain embodiments, the depth control comprises at least one of one or more markings and one or more colors for depicting depth of insertion.

In certain embodiments, the depth control comprises a first portion indicating when to start rotation of the anti-skid surgical instrument and a second portion indicating when to at least one of stop rotation and stop depth penetration of the anti-ski surgical instrument.

In certain embodiments, the depth control comprises a depth stop that adjustably attached to the anti-skid surgical instrument such that the depth of penetration of the anti-skid surgical instrument changes as a position of the depth stop is changed.

In certain embodiments, the shaft comprises one or more notches and the depth control engages at least one of the one or more notches when attached to the anti-skid surgical instrument.

In certain embodiments, the instrument includes a tool support located between the shaft and the shank, wherein: the tool support is shaped and sized to slide through the surgical instrument guide along the axis defined by the guide, and a diameter of the tool support is greater than a diameter of the shank.

In certain embodiments, the end of the mill head has one or more end cutting flutes for cutting axially into the bone tissue.

In certain embodiments, the one or more drill flutes comprise at least two, three, four, six, eight, ten, or twenty flutes.

In certain embodiments, one or more side cutting flutes comprise at least two, three, four, six, eight, ten, or twenty flutes.

In certain embodiments, a longitudinal length of the shaft is greater than a longitudinal length of the mill head.

In certain embodiments, a longitudinal length of the shaft is greater than a longitudinal length of the shank.

In certain embodiments, the one or more drill flutes have a higher twist rate (i.e., larger flute angle) than the one or more side cutting flutes or the one or more drill flutes have a lower twist rate (i.e., smaller flute angle) than the one or more side cutting flutes.

In certain embodiments, the one or more drill flutes have a different twist rate (i.e., different flute angle) than the one or more side cutting flutes.

In certain embodiments, the surgery is spinal, orthopedic, dental, ear, nose, or throat surgery.

In certain embodiments, a manipulator is attached to the robotic arm or molded into the robotic arm.

In another aspect, the disclosed technology includes an anti-skid surgical instrument for preparing a hole in bone tissue of a patient during surgery, the anti-skid surgical instrument having an elongate structure comprising: a mill head at the end of the elongate structure for removing bone tissue with reduced skidding (e.g., unintentional lateral movement of the surgical instrument) of the surgical instrument upon contact of the anti-ski surgical instrument with the bone tissue, wherein the mill head has a flat end substantially perpendicular to a longitudinal axis of the elongate structure, and one or more side-cutting flutes about the longitudinal axis of the elongate structure for cutting into bone tissue; a shank for connection to a drill; a shaft between the mill head and the shank, the shaft having one or more drill flutes (e.g., non-cutting flutes) for evacuating removed bone tissue; and a cannulation in the surgical instrument.

In certain embodiments, the cannulation comprises a hole in the end of the elongate structure (e.g., a tip of the surgical instrument).

In certain embodiments, the instrument includes a spike extending from the mill head.

In certain embodiments, the mill head comprises a concave face (e.g., from which the spike extends).

In certain embodiments, the instrument includes a compliant part that absorbs energy from the mill head.

In certain embodiments, the compliant part comprises at least one of an elastic material, rubber, a bellow, and a universal joint.

In certain embodiments, the compliant part connects a first portion of the anti-ski surgical instrument to a second portion of the anti-skid surgical instrument.

In certain embodiments, the first portion comprises the mill head and a portion of the shaft and the second portion comprises the shank and a portion of the shaft.

In certain embodiments, the compliant part covers at least a portion of the shank.

In certain embodiments, the compliant part covers at least part of the shaft.

In certain embodiments, the compliant part covers at least part of the shaft and the shank.

In certain embodiments, the instrument includes a depth control.

In certain embodiments, the depth control comprises at least one of one or more markings and one or more colors for depicting depth of insertion.

In certain embodiments, the depth control comprises a first portion indicating when to start rotation of the anti-skid surgical instrument and a second portion indicating when to at least one of stop rotation and stop depth penetration of the anti-ski surgical instrument.

In certain embodiments, the depth control comprises a depth stop that adjustably attached to the anti-skid surgical instrument such that the depth of penetration of the anti-skid surgical instrument changes as a position of the depth stop is changed.

In certain embodiments, the shaft comprises one or more notches and the depth control engages at least one of the one or more notches when attached to the anti-skid surgical instrument.

In certain embodiments, the instrument includes a tool support located between the shaft and the shank, wherein: the tool support is shaped and sized to slide through the surgical instrument guide along the axis defined by the guide, and a diameter of the tool support is greater than a diameter of the shank.

In certain embodiments, the end of the mill head has one or more end cutting flutes for cutting axially into the bone tissue.

In certain embodiments, the one or more drill flutes comprise at least two, three, four, six, eight, ten, or twenty flutes.

In certain embodiments, one or more side cutting flutes comprise at least two, three, four, six, eight, ten, or twenty flutes.

In certain embodiments, a longitudinal length of the shaft is greater than a longitudinal length of the mill head.

In certain embodiments, a longitudinal length of the shaft is greater than a longitudinal length of the shank.

In certain embodiments, the one or more drill flutes have a higher twist rate (i.e., larger flute angle) than the one or more side cutting flutes or the one or more drill flutes have a lower twist rate (i.e., smaller flute angle) than the one or more side cutting flutes.

In certain embodiments, the one or more drill flutes have a different twist rate (i.e., different flute angle) than the one or more side cutting flutes.

In certain embodiments, the surgery is spinal, orthopedic, dental, ear, nose, or throat surgery.

In certain embodiments, a manipulator is attached to the robotic arm or molded into the robotic arm.

In another aspect, the disclosed technology includes an anti-skid surgical instrument for preparing a hole in bone tissue of a patient during surgery, the anti-skid surgical instrument having an elongate structure comprising: a mill head at the end of the elongate structure for removing bone tissue with reduced skidding (e.g., unintentional lateral movement of the surgical instrument) of the surgical instrument upon contact of the anti-ski surgical instrument with the bone tissue, wherein the mill head has a flat end substantially perpendicular to a longitudinal axis of the elongate structure, and one or more side-cutting flutes about the longitudinal axis of the elongate structure for cutting into bone tissue; a shank for connection to a drill; a shaft between the mill head and the shank, the shaft having one or more drill flutes (e.g., non-cutting flutes) for evacuating removed bone tissue; and a compliant part that absorbs energy from the mill head.

In certain embodiments, the compliant part comprises at least one of an elastic material, rubber, a bellow, and a universal joint.

In certain embodiments, the compliant part connects a first portion of the anti-ski surgical instrument to a second portion of the anti-skid surgical instrument.

In certain embodiments, the first portion comprises the mill head and a portion of the shaft and the second portion comprises the shank and a portion of the shaft.

In certain embodiments, the compliant part covers at least a portion of the shank.

In certain embodiments, the compliant part covers at least part of the shaft.

In certain embodiments, the compliant part covers at least part of the shaft and the shank.

In certain embodiments, the instrument includes a spike extending from the mill head.

In certain embodiments, the mill head comprises a concave face (e.g., from which the spike extends).

In certain embodiments, the instrument includes a cannulation in the surgical instrument.

In certain embodiments, the cannulation comprises a hole in the end of the elongate structure (e.g., a tip of the surgical instrument).

In certain embodiments, the instrument includes a depth control.

In certain embodiments, the depth control comprises at least one of one or more markings and one or more colors for depicting depth of insertion.

In certain embodiments, the depth control comprises a first portion indicating when to start rotation of the anti-skid surgical instrument and a second portion indicating when to at least one of stop rotation and stop depth penetration of the anti-ski surgical instrument.

In certain embodiments, the depth control comprises a depth stop that adjustably attached to the anti-skid surgical instrument such that the depth of penetration of the anti-skid surgical instrument changes as a position of the depth stop is changed.

In certain embodiments, the shaft comprises one or more notches and the depth control engages at least one of the one or more notches when attached to the anti-skid surgical instrument.

In certain embodiments, the instrument includes a tool support located between the shaft and the shank, wherein: the tool support is shaped and sized to slide through the surgical instrument guide along the axis defined by the guide, and a diameter of the tool support is greater than a diameter of the shank.

In certain embodiments, the end of the mill head has one or more end cutting flutes for cutting axially into the bone tissue.

In certain embodiments, the one or more drill flutes comprise at least two, three, four, six, eight, ten, or twenty flutes.

In certain embodiments, one or more side cutting flutes comprise at least two, three, four, six, eight, ten, or twenty flutes.

In certain embodiments, a longitudinal length of the shaft is greater than a longitudinal length of the mill head.

In certain embodiments, a longitudinal length of the shaft is greater than a longitudinal length of the shank.

In certain embodiments, the one or more drill flutes have a higher twist rate (i.e., larger flute angle) than the one or more side cutting flutes or the one or more drill flutes have a lower twist rate (i.e., smaller flute angle) than the one or more side cutting flutes.

In certain embodiments, the one or more drill flutes have a different twist rate (i.e., different flute angle) than the one or more side cutting flutes.

In certain embodiments, the surgery is spinal, orthopedic, dental, ear, nose, or throat surgery.

In certain embodiments, a manipulator is attached to the robotic arm or molded into the robotic arm.

In another aspect, the disclosed technology includes an anti-skid surgical instrument for preparing a hole in bone tissue of a patient during surgery, the anti-skid surgical instrument having an elongate structure comprising: a mill head at the end of the elongate structure for removing bone tissue with reduced skidding (e.g., unintentional lateral movement of the surgical instrument) of the surgical instrument upon contact of the anti-ski surgical instrument with the bone tissue, wherein the mill head has a flat end substantially perpendicular to a longitudinal axis of the elongate structure, and one or more side-cutting flutes about the longitudinal axis of the elongate structure for cutting into bone tissue; a shank for connection to a drill; a shaft between the mill head and the shank, the shaft having one or more drill flutes (e.g., non-cutting flutes) for evacuating removed bone tissue; and a depth control.

In certain embodiments, the depth control comprises one or more markings.

In certain embodiments, the depth control comprises one or more colors.

In certain embodiments, the depth control comprises a first portion indicating when to start rotation of the anti-skid surgical instrument and a second portion indicating when to at least one of stop rotation and stop depth penetration of the anti-ski surgical instrument.

In certain embodiments, the depth control comprises a depth stop that adjustably attached to the anti-skid surgical instrument such that the depth of penetration of the anti-skid surgical instrument changes as a position of the depth stop is changed.

In certain embodiments, the shaft comprises one or more notches and the depth control engages at least one of the one or more notches when attached to the anti-skid surgical instrument.

In certain embodiments, instrument includes a spike extending from the mill head.

In certain embodiments, the mill head comprises a concave face (e.g., from which the spike extends).

In certain embodiments, the instrument includes a cannulation in the surgical instrument.

In certain embodiments, the cannulation comprises a hole in the end of the elongate structure (e.g., a tip of the surgical instrument).

In certain embodiments, the instrument includes a compliant part that absorbs energy from the mill head.

In certain embodiments, the compliant part comprises at least one of an elastic material, rubber, a bellow, and a universal joint.

In certain embodiments, the compliant part connects a first portion of the anti-ski surgical instrument to a second portion of the anti-skid surgical instrument.

In certain embodiments, the first portion comprises the mill head and a portion of the shaft and the second portion comprises the shank and a portion of the shaft.

In certain embodiments, the compliant part covers at least a portion of the shank.

In certain embodiments, the compliant part covers at least part of the shaft.

In certain embodiments, the compliant part covers at least part of the shaft and the shank.

In certain embodiments, the instrument includes a tool support located between the shaft and the shank, wherein: the tool support is shaped and sized to slide through the surgical instrument guide along the axis defined by the guide, and a diameter of the tool support is greater than a diameter of the shank.

In certain embodiments, the end of the mill head has one or more end cutting flutes for cutting axially into the bone tissue.

In certain embodiments, the one or more drill flutes comprise at least two, three, four, six, eight, ten, or twenty flutes.

In certain embodiments, one or more side cutting flutes comprise at least two, three, four, six, eight, ten, or twenty flutes.

In certain embodiments, a longitudinal length of the shaft is greater than a longitudinal length of the mill head.

In certain embodiments, a longitudinal length of the shaft is greater than a longitudinal length of the shank.

In certain embodiments, the one or more drill flutes have a higher twist rate (i.e., larger flute angle) than the one or more side cutting flutes or the one or more drill flutes have a lower twist rate (i.e., smaller flute angle) than the one or more side cutting flutes.

In certain embodiments, the one or more drill flutes have a different twist rate (i.e., different flute angle) than the one or more side cutting flutes.

In certain embodiments, the surgery is spinal, orthopedic, dental, ear, nose, or throat surgery.

In certain embodiments, a manipulator is attached to the robotic arm or molded into the robotic arm.

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIG. 35A, FIG. 35B, and FIG. 35C illustrate an anti-skive drill bit in accordance with embodiments of the disclosed technology;

FIG. 37A and FIG. 37B illustrate example compliant parts in accordance with an embodiment of the invention;

Figure 1:
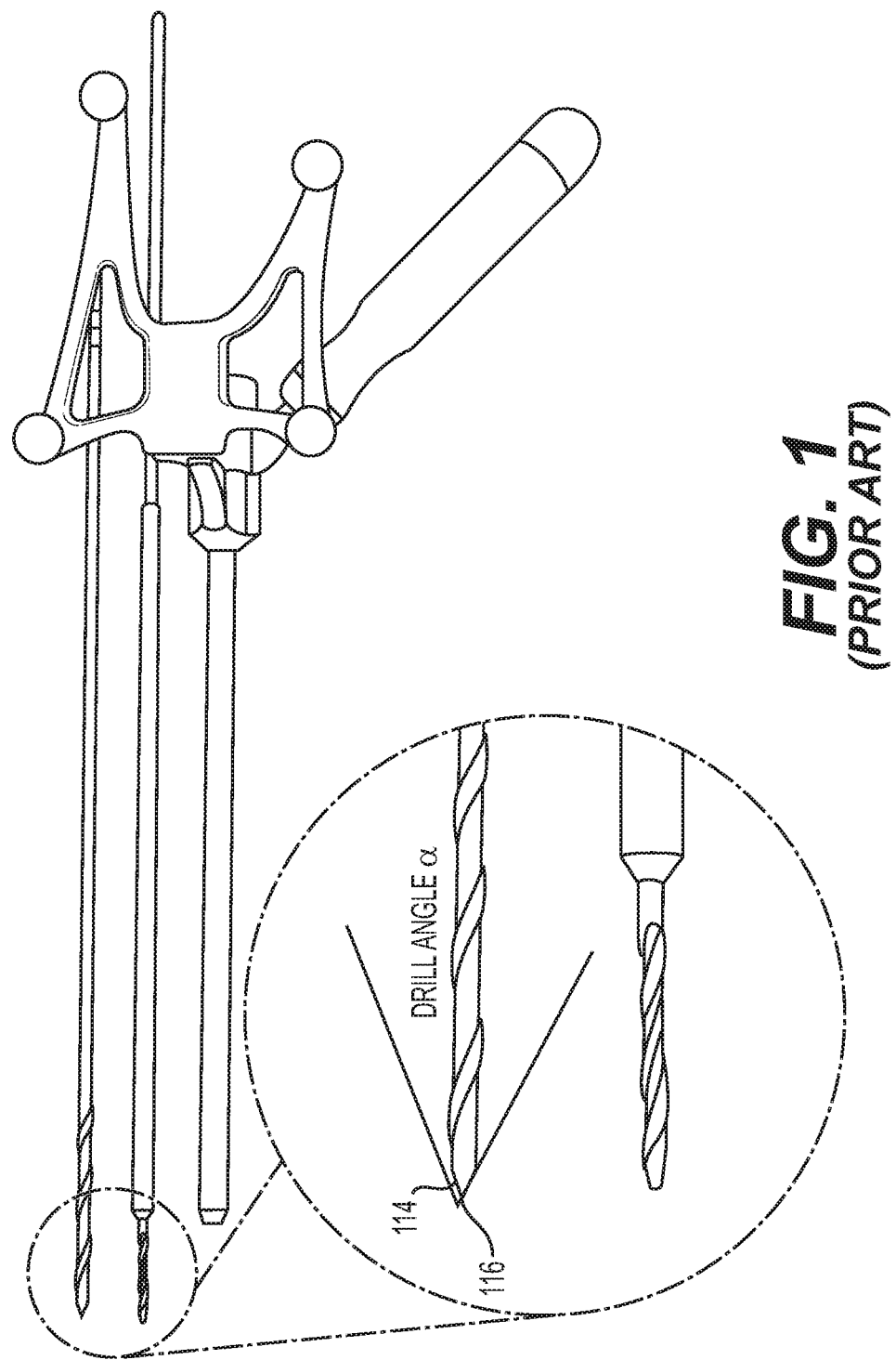
FIG. 1 is an illustration of example drill bits for preparing holes in bone tissue.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

Described herein is an anti-skid surgical instrument for use in preparing holes in bone tissue. In certain types of surgeries it is necessary to prepare a precise hole in bone tissue (e.g. spinal surgeries and pedicle screw placement, intramedullary screw placement); however, in many instances, human anatomy is not well adapted for drilling in these regions because the angle between the drill axis and surface of the bone is not perpendicular. The disclosed technology provides the ability to precisely prepare a hole in bone tissue by minimizing the likelihood that the surgical instrument skids upon contact with bone tissue.

As used herein, the phrase "prepare a hole in bone tissue" encompasses milling, drilling, grinding, and/or cutting bone tissue and/or bone-like tissue. A "hole" encompasses any cavity, dent, or depression.

FIG. 1 is an illustration of example prior art drill bits 102 and 104 and an example surgical instrument guide 106. Typically, surgical instruments include a tapered end 114 that narrows to a point 116. The point 116 is used to guide the drill bit. Standard surgical instruments, especially drill bits, may skid on the surface of bone tissue which significantly decreases precision of the hole. The skidding can be linked with drill angle α which is not well adapted to drilling at an angle (different from the right angle) to the bone tissue surface. Given that the surface of most bones are not perfectly flat, standard drill bits often result in imprecise holes in the bone. For example, if the side of the drill (e.g., the side of the tapered tip 114 of the drill) touches the bone tissue before tip 116 of the drill bit has entered the tissue and provides guidance, drill skid is more likely.

Figure 2:
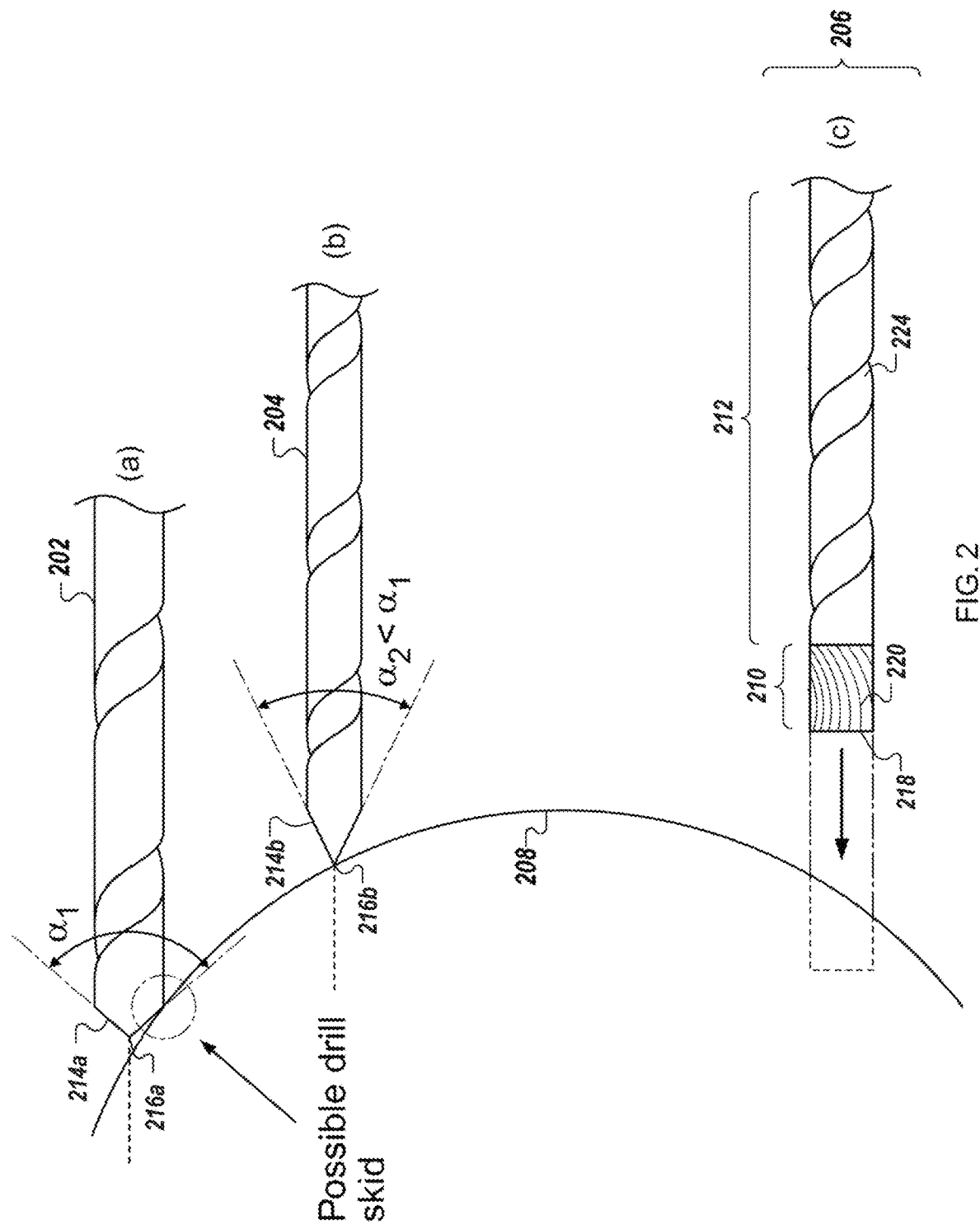
FIG. 2 is an illustration of example surgical instruments for preparing holes in bone tissue.

FIG. 2 is a comparison of three drill bits contacting the surface of bone tissue 208. As shown in FIG. 2, drill bit 202 is likely to skid because the tip 216a of the drill bit 202 will not contract the surface of the bone tissue 208 first. Instead, the side 214a of the tapered tip will contract the bone tissue 208 before the tip 216a. Relative to drill bit 202, the tip 216b of drill bit 204 is less likely to skid because the tip 216b of the drill bit 204 contracts the bone tissue 208 first. However, one of the reasons it is difficult to predict if and when a drill bit will skid during surgeries is the difficulty of determining whether the tip of the drill bit will contract the bone tissue 208 first. The anti-skid surgical instrument 206 as shown in FIG. 2 reduces the risk of drill bit skid because the "tip" is a flat milling surface 218 which is perpendicular to the surface of the body of the surgical instrument. The mill head 210 of the anti-skid surgical instrument 206 is adapted for milling (e.g., rather than drilling) when entering the bone tissue 208. The portion of the instrument body 212 after the head 210, in some implementations, is adapted for drilling (e.g., contains evacuating holes, spirals, twists, etc.).

In some implementations, the anti-skid surgical instrument 206 has a mill head 210 at the end of the elongate structure for removing bone tissue with reduced skidding (e.g., unintentional lateral movement of the surgical instrument) of the surgical instrument upon contact of the anti-ski surgical instrument with the bone tissue 208. The mill head 210 has a flat end 218 substantially perpendicular to a longitudinal axis of the elongate structure. In some implementations, the mill head 210 has one or more side-cutting flutes 220 (e.g., sharpened) about the longitudinal axis of the elongate structure for cutting into bone tissue. The one or more side cutting flutes 220 can include two, three, four, six, eight, ten, or twenty flutes.

In some implementations, the anti-skid surgical instrument 206 has a shank (not shown) for connection to a drill. In some implementations, the anti-skid surgical instrument 206 has a shaft 212 between the mill head 210 and the shank, the shaft 212 having one or more drill flutes 224 (e.g., non-cutting flutes; e.g., unsharpened) for evacuating removed bone tissue. In some implementations, the one or more drill flutes 224 include two, three, four, six, eight, ten, or twenty flutes. The one or more drill flutes 224 are different than the one or more side cutting flutes 220. For example, the drill flutes 224 may have a different (e.g., larger or smaller) twist rate, (e.g., flute angle) than the side cutting flutes 220.

In some implementations, the flat end 218 of the mill head 210 has one or more end cutting flutes (not shown) for cutting axially into the bone tissue. In some implementations, the one or more end cutting flutes are cutting teeth. Additionally, a longitudinal length of the shaft, in some implementations, is greater than a longitudinal length of the mill head. The longitudinal length of the shaft, in some implementations, is less than a longitudinal length of the mill head.

As shown in FIG. 2, the anti-skid surgical instrument 206 has an elongate structure with a mill head 210 with milling surface 218, a shaft 212 with a drill surface. In some implementations, the instrument 206 includes a second end, opposite the first end 210, with a shank configured to be grasped by a drill. The mill head 210 of the anti-skid surgical instrument 206 is flat and substantially perpendicular to the surface of the elongate structure, thereby reducing skidding (e.g., unintentional lateral movement of the surgical instrument 206) of the surgical instrument 206 upon contact of the milling surface 218 with bone tissue 208.

The mill end 210, in some implementations, utilizes rotary cutters to remove material. The mill end 210 can take the form of several shapes and sizes. For example, the mill end 210 can be an end mill, slab mill, or other types of milling devices.

The flutes 220 of the mill head 210, in some implementations, are deep helical grooves running up the cutter, while the sharp blade along the edge of the flute 220 is known as the tooth. The tooth cuts the material, and chips of this material are pulled up the flute 220 by the rotation of the cutter. In some implementations, there is one tooth per flute. In some implementations, there are two or more teeth per flute. For example, the cutter of each flute 220 may have 2, 3, 4, 5, or more teeth (e.g., 1-4, 5-10, or 10-20 teeth). Typically, the more teeth a cutter has, the more rapidly it can remove material. Thus, typically a 4-tooth cutter can remove material at twice the rate of a 2-tooth cutter. The mill head 210 may be an end mill with cutting teeth at one end (i.e., the flat end 218) and on the sides 220 of mill end 210. For example, the flat end 218 can be a flat bottom cutter.

In some implementations, the surgical instrument 206 is rigidly guided (e.g., by a robotic surgical system). The surgical instrument 206 may cause higher radial forces when entering bone tissue 208, thus a rigid guide ensures that the hole will be placed accurately. The drill used with the surgical instrument 206, in some implementations, is sufficiently rigid to avoid deflection of the drill itself. A high rotational velocity drill (e.g., power drill) may be used to reduce radial forces.

In certain embodiments, hole placement accuracy is achieved by the combination of the anti-skid drill bit and the robotic surgical system. The rigidity provided by the robotic surgical system along with the anti-skid drill bit allows precise drilling of holes, thereby minimizing (or eliminating) skiving along the bone upon contact between the bone and the anti-skid drill bit. The robotic surgical system provides rigidity from the floor of the operating room (and/or the surgical table) to the surgical instrument itself. This is achieved by each component within the "chain" providing rigidity. An example surgical system is described in U.S. Pat. No. 9,283,048, filed Apr. 30, 2014 and entitled "Apparatus, Systems, and Methods for Precise Guidance of Surgical Tools," the contents of which are hereby incorporated by reference in its entirety. In this example, the mobile cart is designed to rest on legs during surgery such that the robot is fixed in place. Further, the robotic arm is rigidly attached to the base and is an active arm. Similarly, the notched guide and the surgical instrument holder are designed to provide rigidity. Examples of notched guides are provided in U.S. Pat. No. 9,241,771, filed Jan. 15, 2015, entitled "Notched Apparatus for Guidance of an Insertable Instrument along an Axis during Spinal Surgery," which is hereby incorporated by reference in its entirety. Examples of surgical instrument holders are provided in U.S. Patent Application Publication No. 2015/0305817, filed Apr. 24, 2015, entitled "Surgical Instrument Holder for use with a Robotic Surgical System," which is hereby incorporated by reference in its entirety. The combination of the notched guide or surgical instrument holder, active robotic arm, and robot (e.g., robot base), along with the anti-skid drill bit, reduces skidding (e.g., skiving) when the drill bit contacts the bone, thereby allowing accurate placement of holes for surgical screws.

In some implementations, the surgical instrument 206 is used in combination with a robotic surgical system, such as the robotic surgical system described in U.S. Pat. No. 9,283,048, filed Apr. 30, 2014 and entitled "Apparatus, Systems, and Methods for Precise Guidance of Surgical Tools," the contents of which are hereby incorporated by reference in its entirety.

In some implementations, the surgical instrument 206 is used with a passive arm or any device that provides rigid fixation of the surgical instrument 206. The surgical instrument 206 may be insertable into a surgical instrument guide such that the surgical instrument 206 is constrained by the surgical instrument guide. The surgical instrument guide may include a rigid hollow tubular structure having a first open end and a second open end. The structure of the guide may define the axis along which movement of a surgical instrument sliding through the structure is restricted. The tubular structure may have an interior surface shaped and sized to accommodate the anti-skid surgical instrument 206 sliding through the guide such that movement of the surgical instrument 206 (e.g., fitted with a tool support) is constrained in all directions except along the axis defined by the guide. The surgical instrument 206 may be fitted with or have an integrated tool support such that the tool support engages the guide to provide accurate guidance of the surgical instrument 206. For example, the anti-skid surgical instrument 206 may be fitted with a tool support shaped and sized to slide through the surgical instrument guide along the axis defined by the guide.

In instances in which the surgical instrument 206 is guided by a robotic surgical system, the robotic surgical system may include a robotic arm. In some implementations, the robotic arm has an end effector including a surgical instrument guide attached thereto, the surgical instrument guide configured to hold and/or restrict movement of a surgical instrument therethrough. A navigation marker may be used to track the surgical instrument 206. The axis of the surgical instrument guide can be aligned with the desired trajectory in relation to the patient situation via the manipulator.

Figure 3:
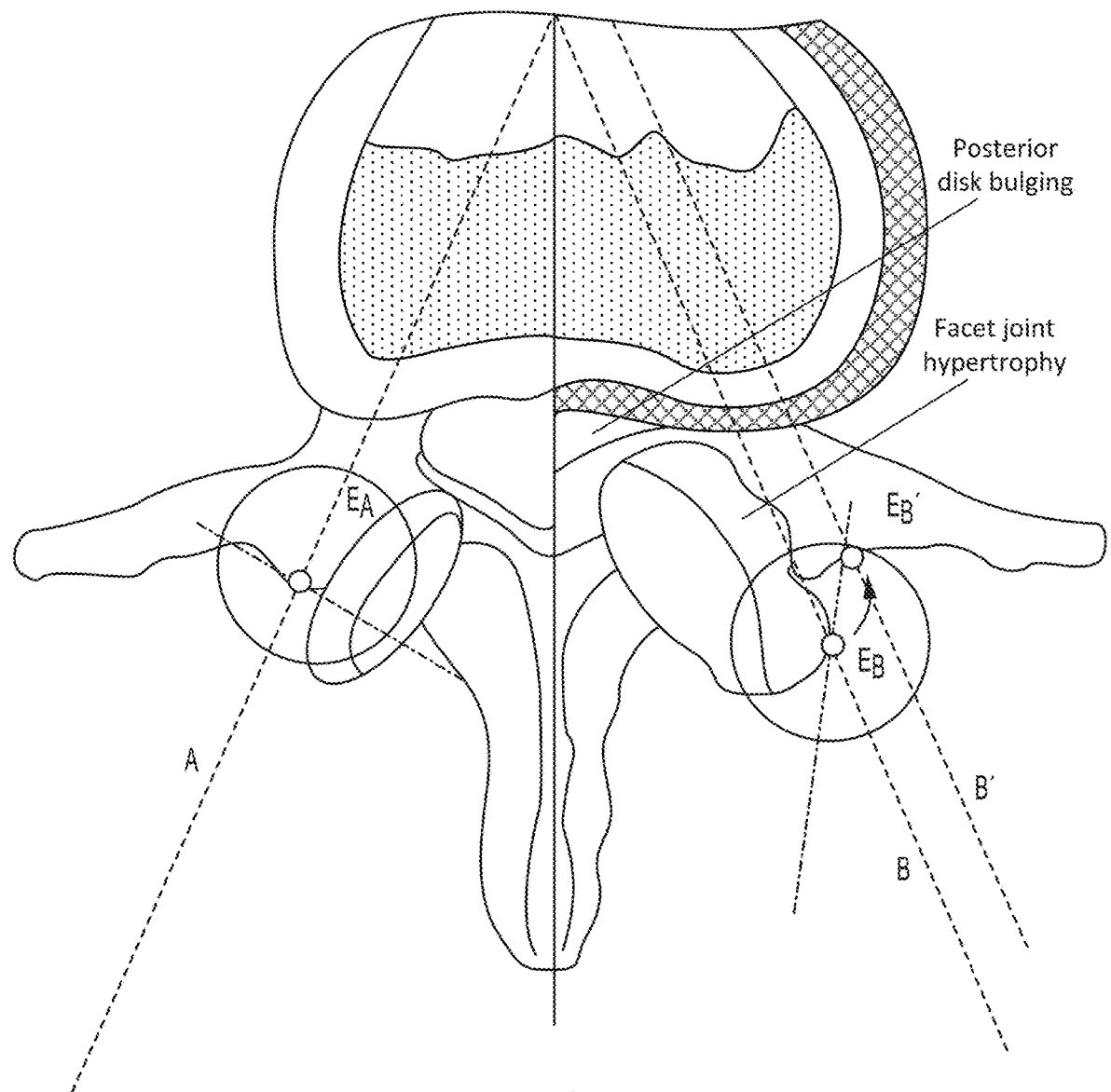
FIG. 3 illustrates why a drill bit skiving on the surface vertebrae can be particularly problematic for abnormal vertebrae (e.g. arthritic)

FIG. 3 illustrates why drill bit skiving on the surface vertebrae can be particularly problematic for abnormal vertebrae (e.g. arthritic). On the left side of the image, a "normal" vertebra is shown with standard trajectory A going through a pedicle. In this case entry point $E_A$ is located where surface of the bone is close to being perpendicular to drilling axis. This decreases the possibility of skiving.

In contrast, situation on the right side of the image shows an arthritic vertebrae (e.g., of an older person). Due to additional hard bony tissue, facet joint increases its volume and interferes with the trajectory. It places ideal entry point $E_B$ on the angled surface and increases chances of skiving. If skiving occurs, it will likely displace entry point to $E_{B1}$. Instead of the trajectory being trajectory B, it likely will be trajectory B1 and might lead to screw implant going out of the pedicle. This can result in serious clinical consequences (neurologic, vascular, etc.) for the patient. It should be noted that in most operated patients arthritis appears at various levels of advancement (e.g., healthy patients would have surgery principally as a result of trauma only).

Figure 4B:
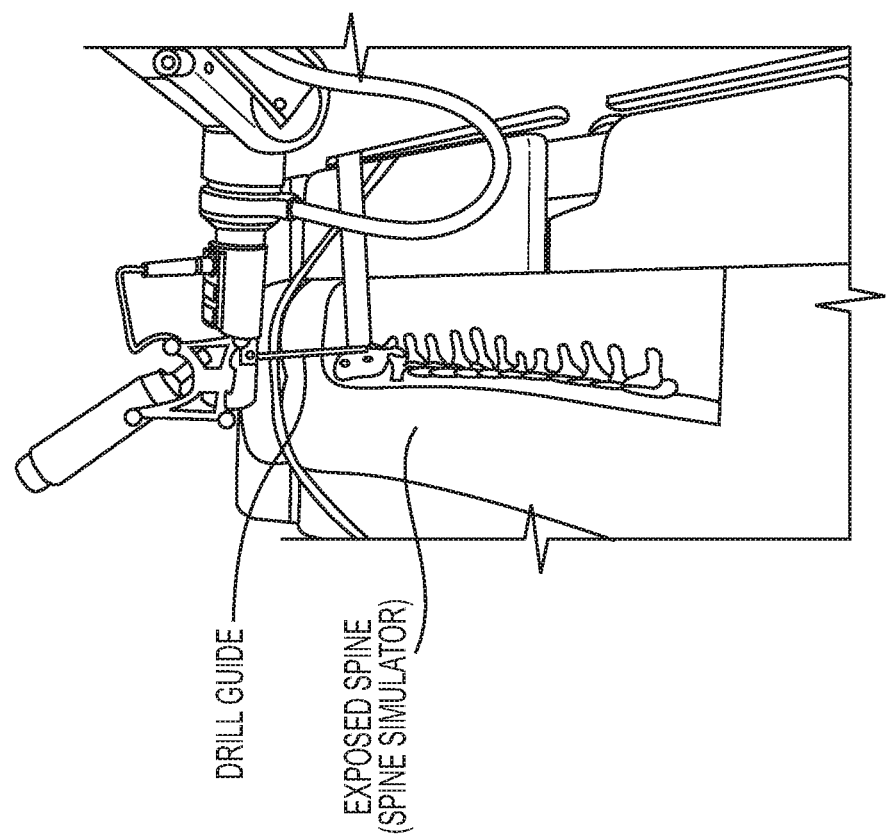
FIG. 4A and FIG. 4B are still photographs taken during an experiment performed using the disclosed technology and standard drill bits to measure the amount of skiving experienced with different drill bit designs.
Figure 4A:
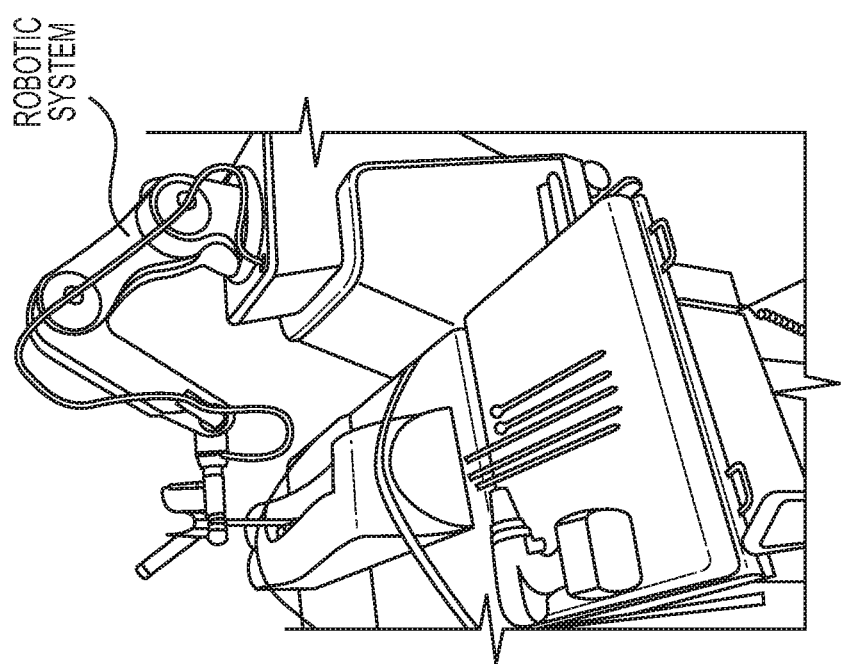

FIGS. 4A through 30 are still photographs taken during an experiment performed using the disclosed technology and standard drill bits to measure the amount of skiving experienced with different drill bit designs. As discussed above, a problem with drilling bone with traditional drill bits is drill skiving on the surface of the bone (e.g., vertebrae). The test setup is shown in FIGS. 4A-4B. A robot and a drill guide were used to drill holes in simulated patient anatomy. An example robot that can be used with the disclosed technology is described in U.S. Pat. No. 9,283,048, filed Apr. 30, 2014 and entitled "Apparatus, Systems, and Methods for Precise Guidance of Surgical Tools," which is hereby incorporated by reference in its entirety. The patient's anatomy was simulated by a custom-made spine simulator which integrates bony tissue and foam representing soft tissue to provide a model with sufficient vertebrae mechanical behavior (resistance, elasticity, bone quality, etc.).

Figure 5:
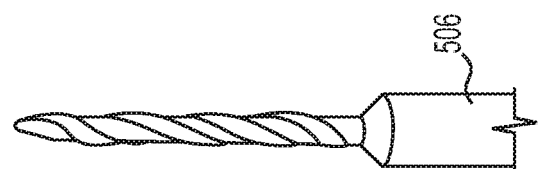
FIG. 5 is a still photograph taken during an experiment performed using the disclosed technology and standard drill bits to measure the amount of skiving experienced with different drill bit designs.
Figure 5:
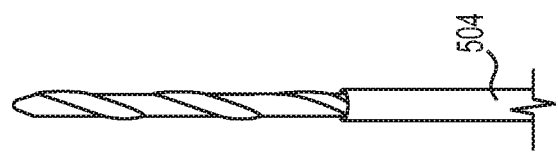
Figure 5:
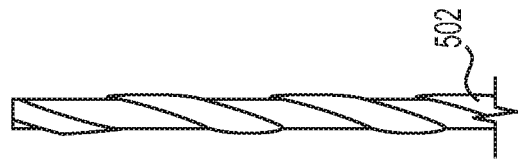
Figure 6:
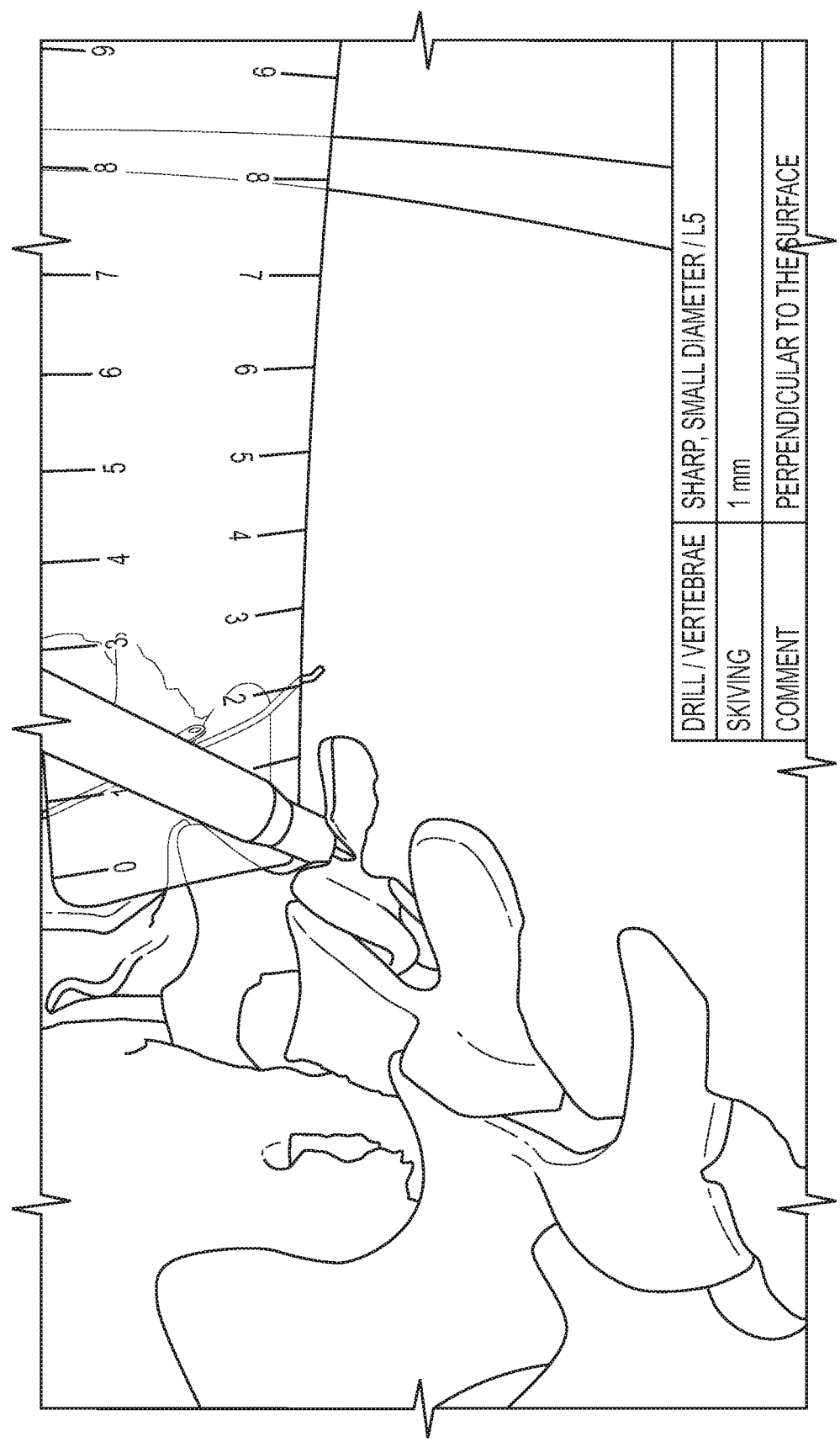
FIG. 6 is a still photograph taken during an experiment performed using the disclosed technology and standard drill bits to measure the amount of skiving experienced with different drill bit designs.
Figure 7:
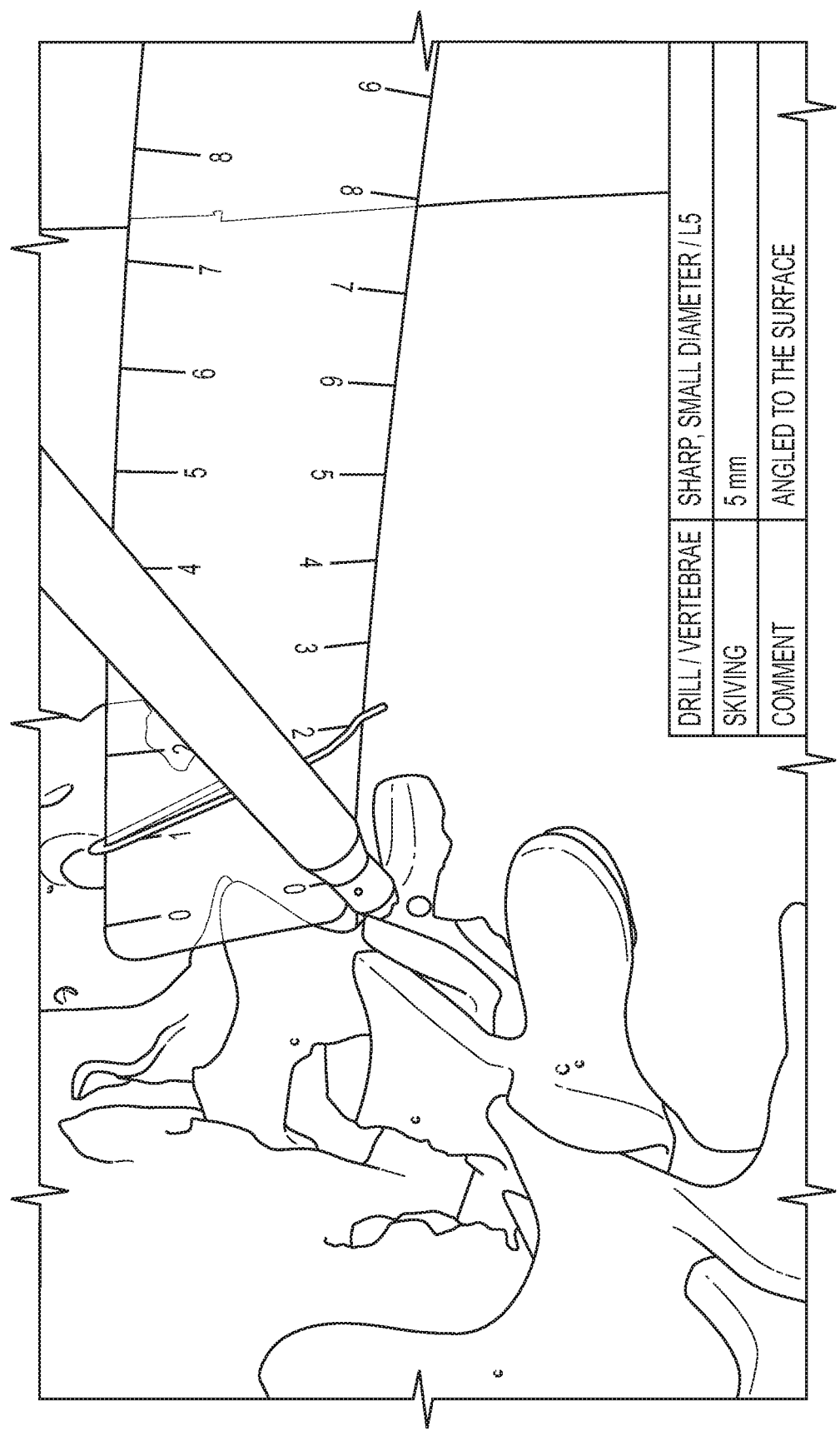
FIG. 7 is a still photograph taken during an experiment performed using the disclosed technology and standard drill bits to measure the amount of skiving experienced with different drill bit designs.
Figure 8:
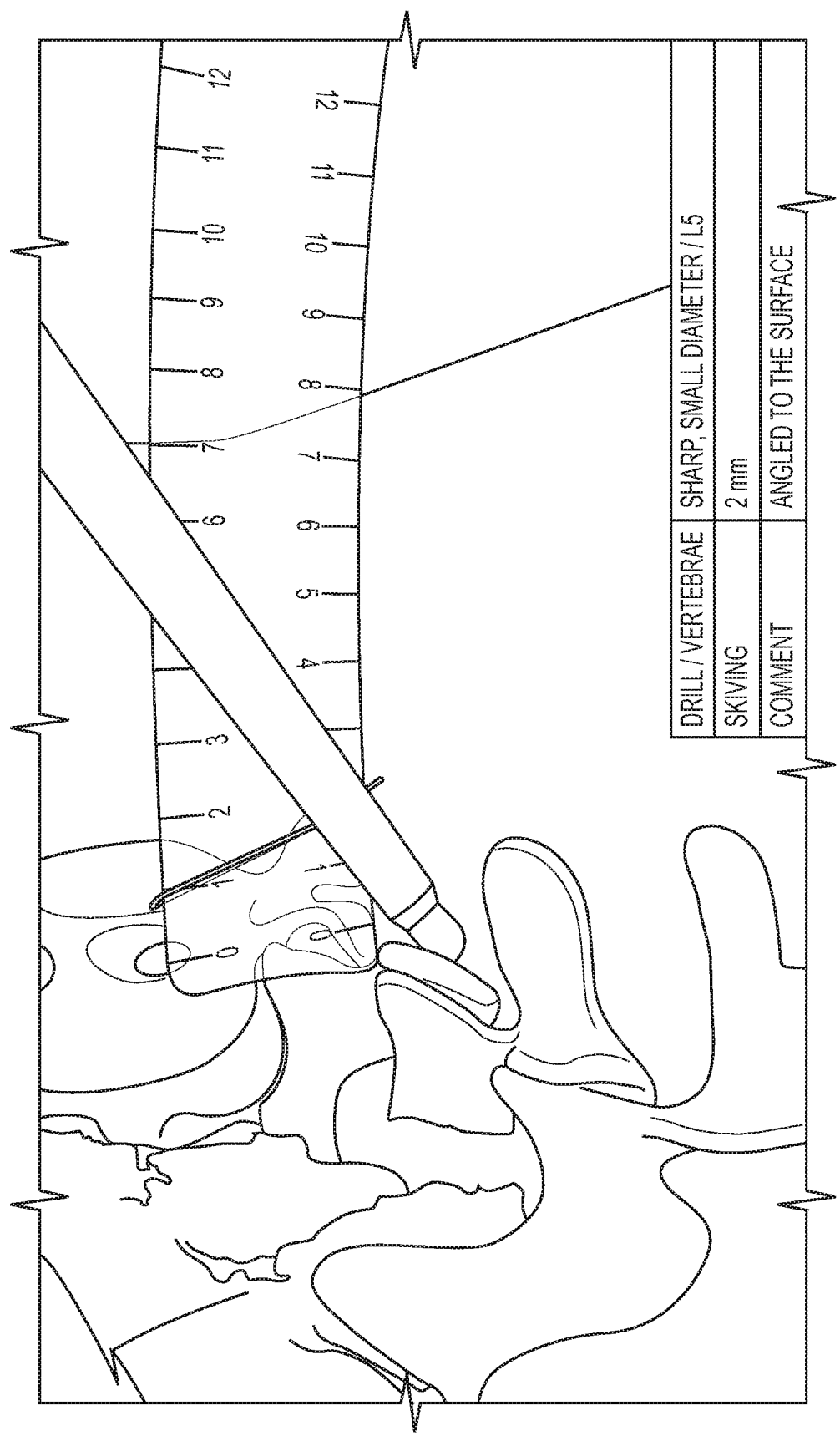
FIG. 8 is a still photograph taken during an experiment performed using the disclosed technology and standard drill bits to measure the amount of skiving experienced with different drill bit designs.
Figure 9:
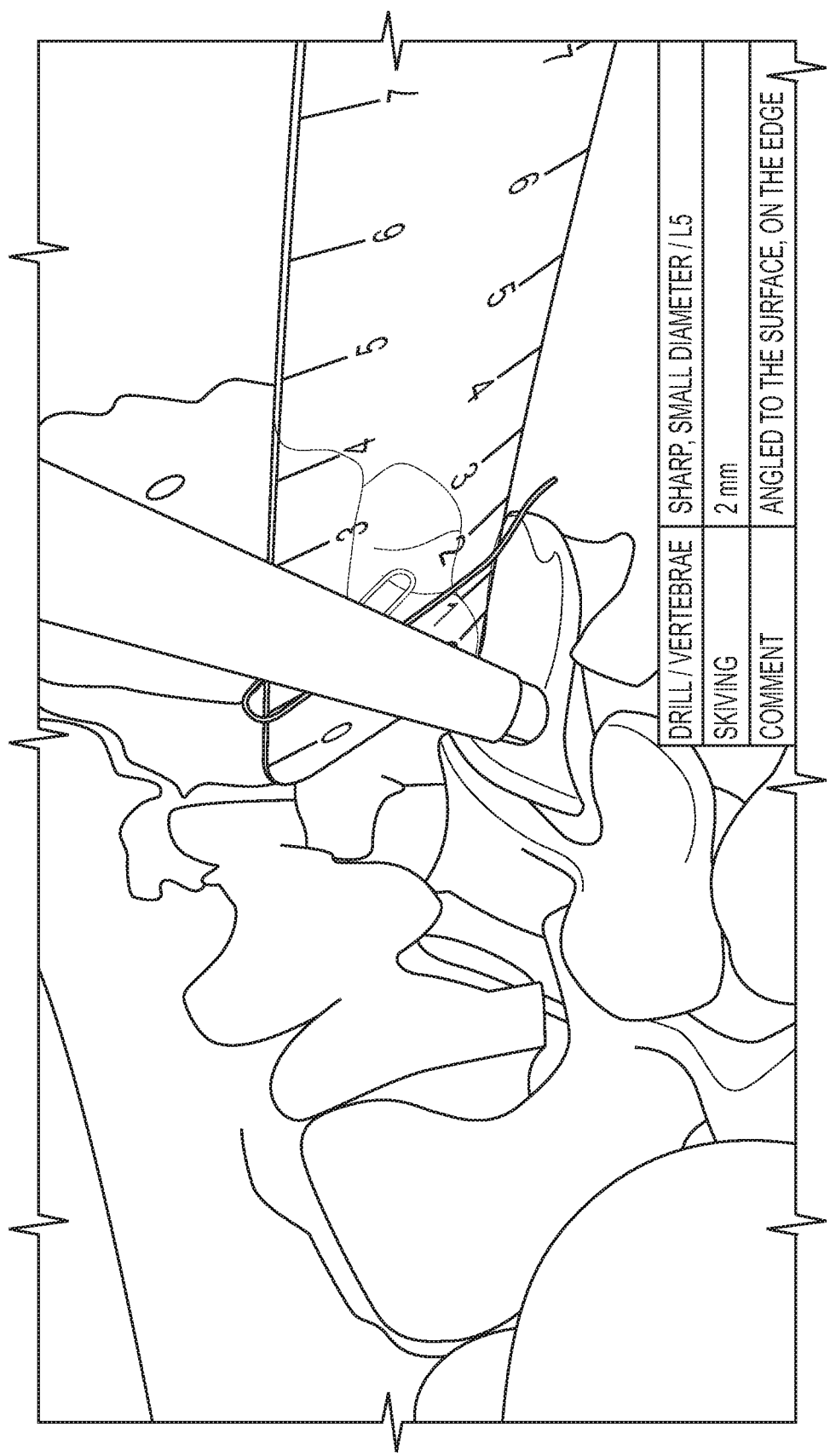
FIG. 9 is a still photograph taken during an experiment performed using the disclosed technology and standard drill bits to measure the amount of skiving experienced with different drill bit designs.
Figure 10:
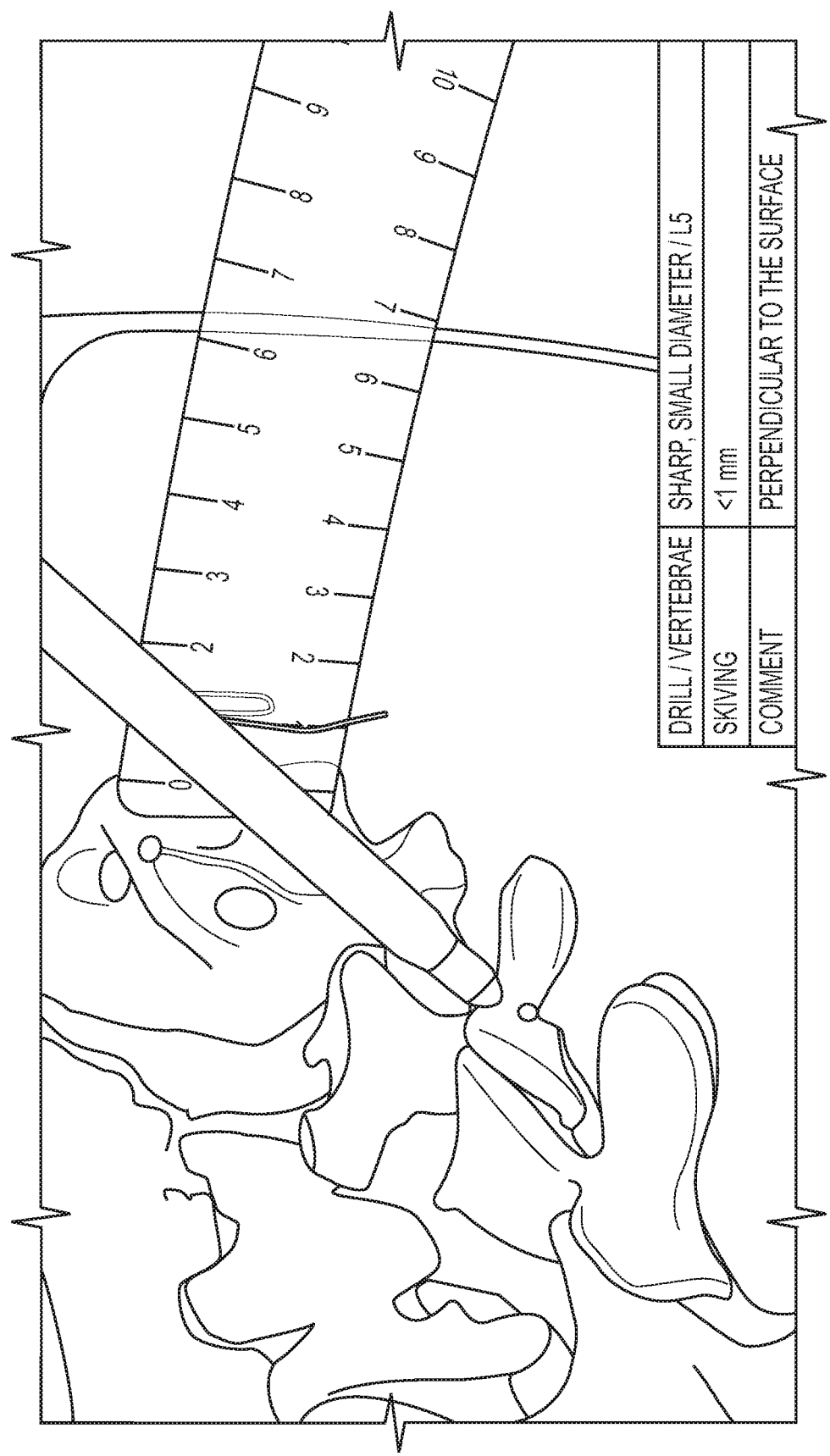
FIG. 10 is a still photograph taken during an experiment performed using the disclosed technology and standard drill bits to measure the amount of skiving experienced with different drill bit designs.
Figure 11:
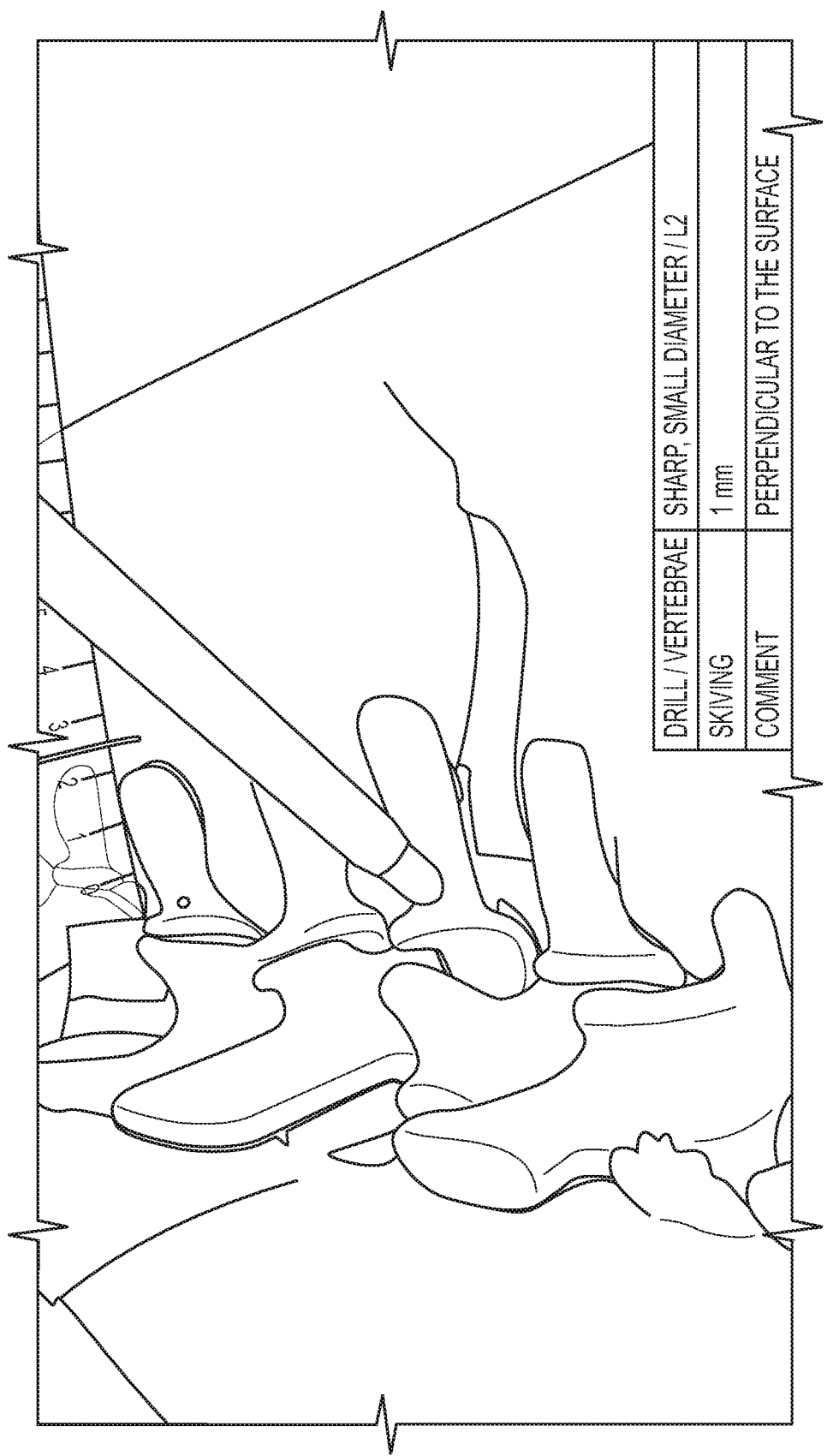
FIG. 11 is a still photograph taken during an experiment performed using the disclosed technology and standard drill bits to measure the amount of skiving experienced with different drill bit designs.
Figure 12:
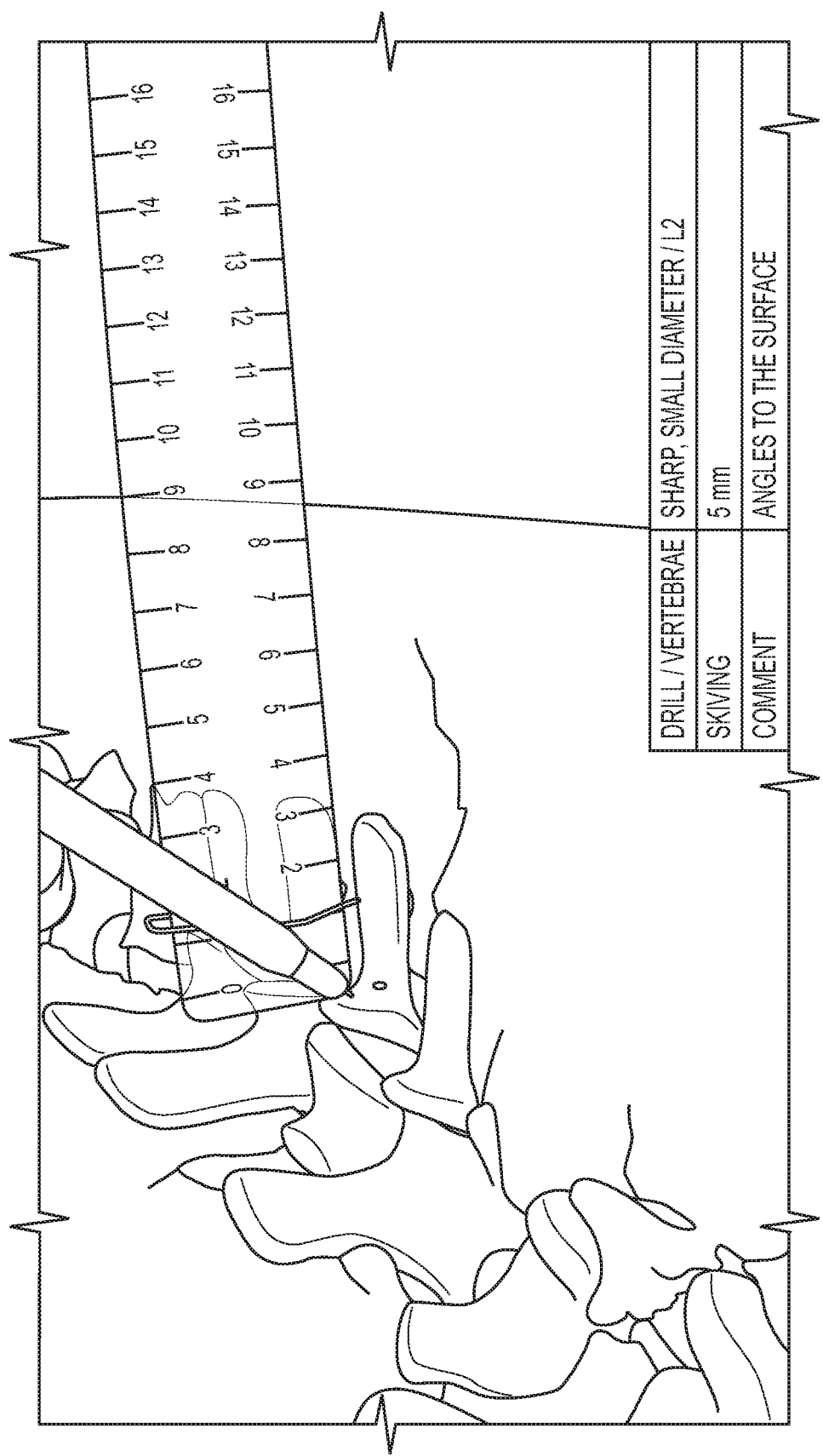
FIG. 12 is a still photograph taken during an experiment performed using the disclosed technology and standard drill bits to measure the amount of skiving experienced with different drill bit designs.
Figure 13:
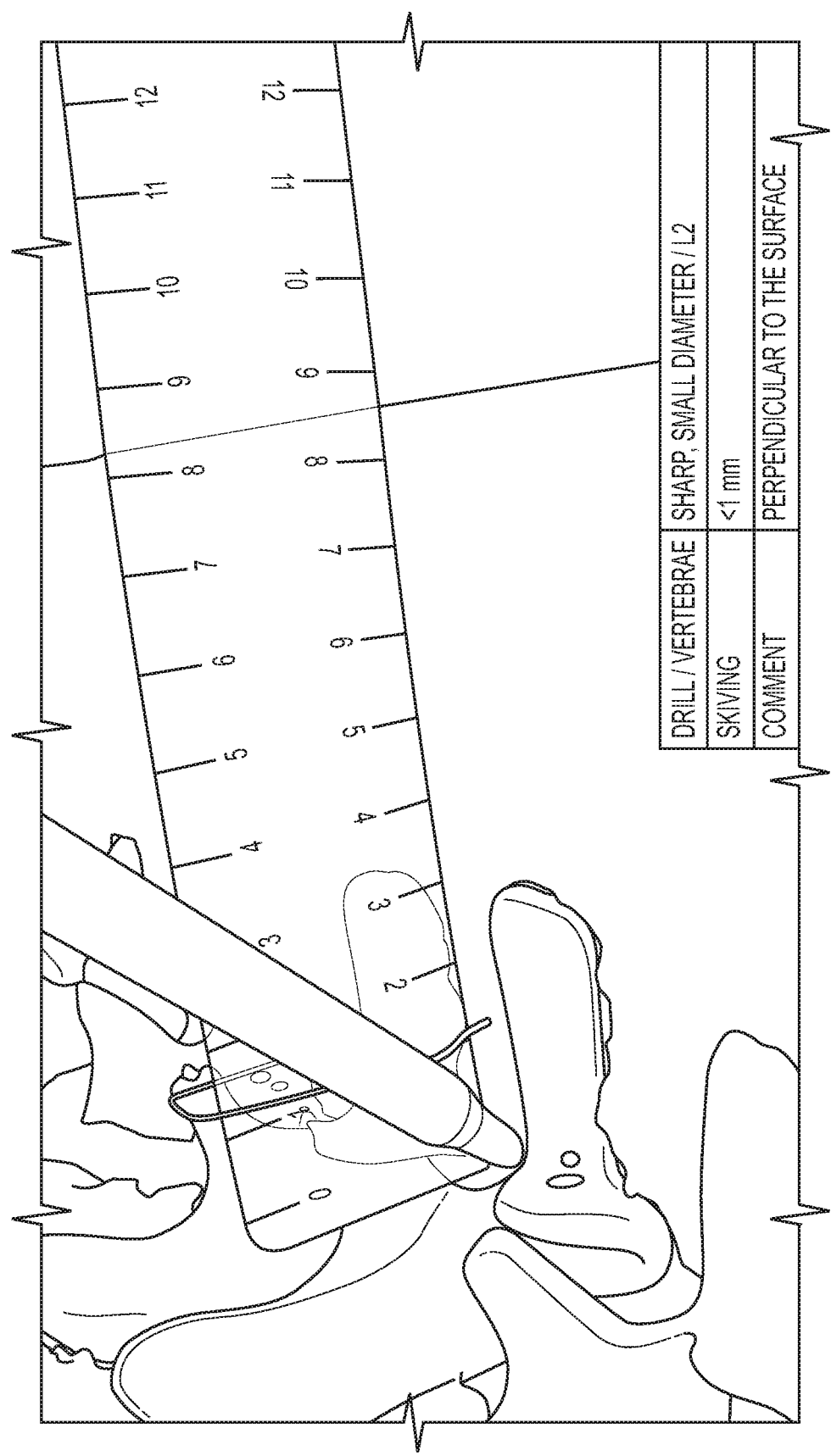
FIG. 13 is a still photograph taken during an experiment performed using the disclosed technology and standard drill bits to measure the amount of skiving experienced with different drill bit designs.
Figure 14:
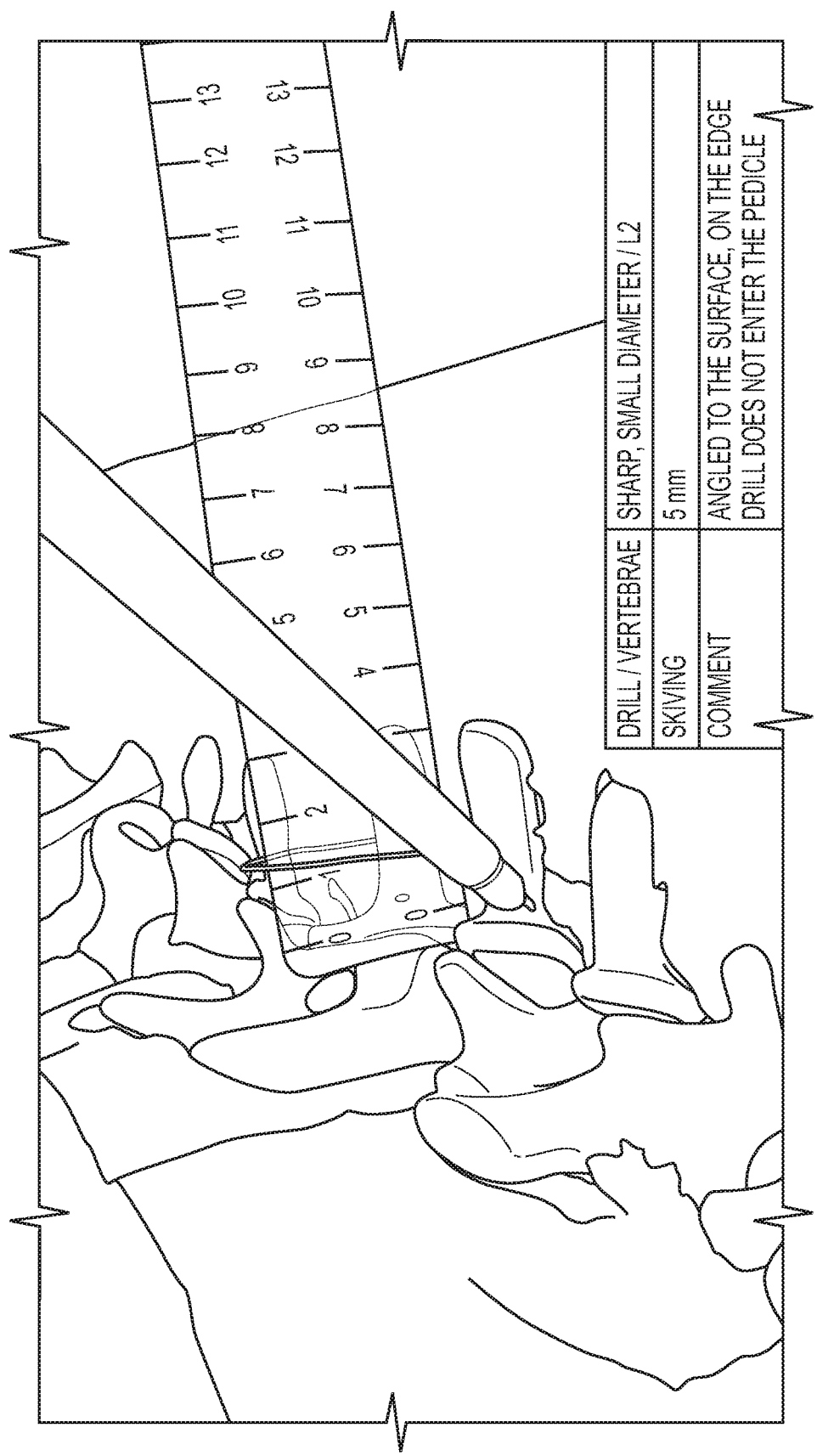
FIG. 14 is a still photograph taken during an experiment performed using the disclosed technology and standard drill bits to measure the amount of skiving experienced with different drill bit designs.
Figure 15:
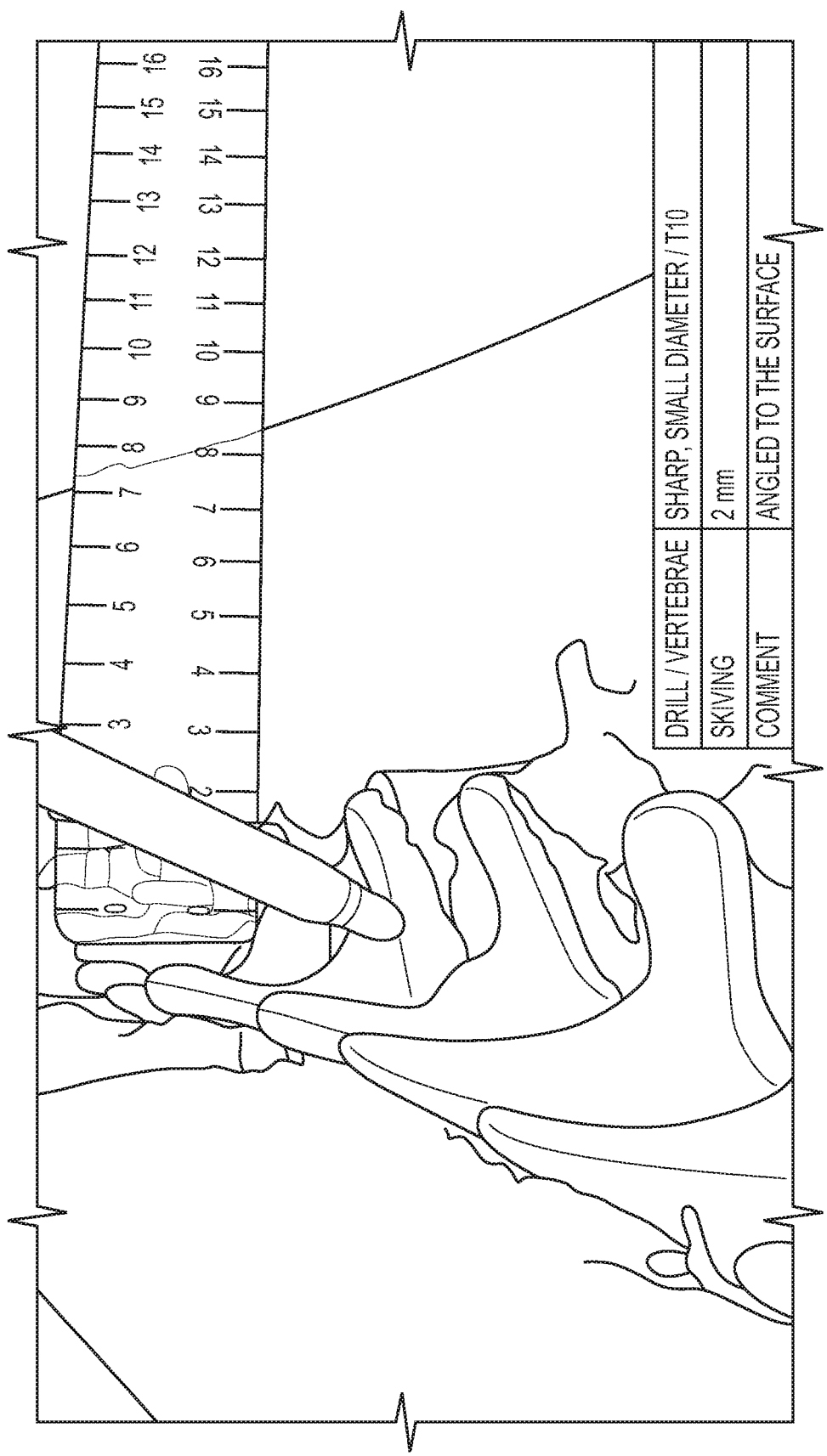
FIG. 15 is a still photograph taken during an experiment performed using the disclosed technology and standard drill bits to measure the amount of skiving experienced with different drill bit designs.
Figure 16:
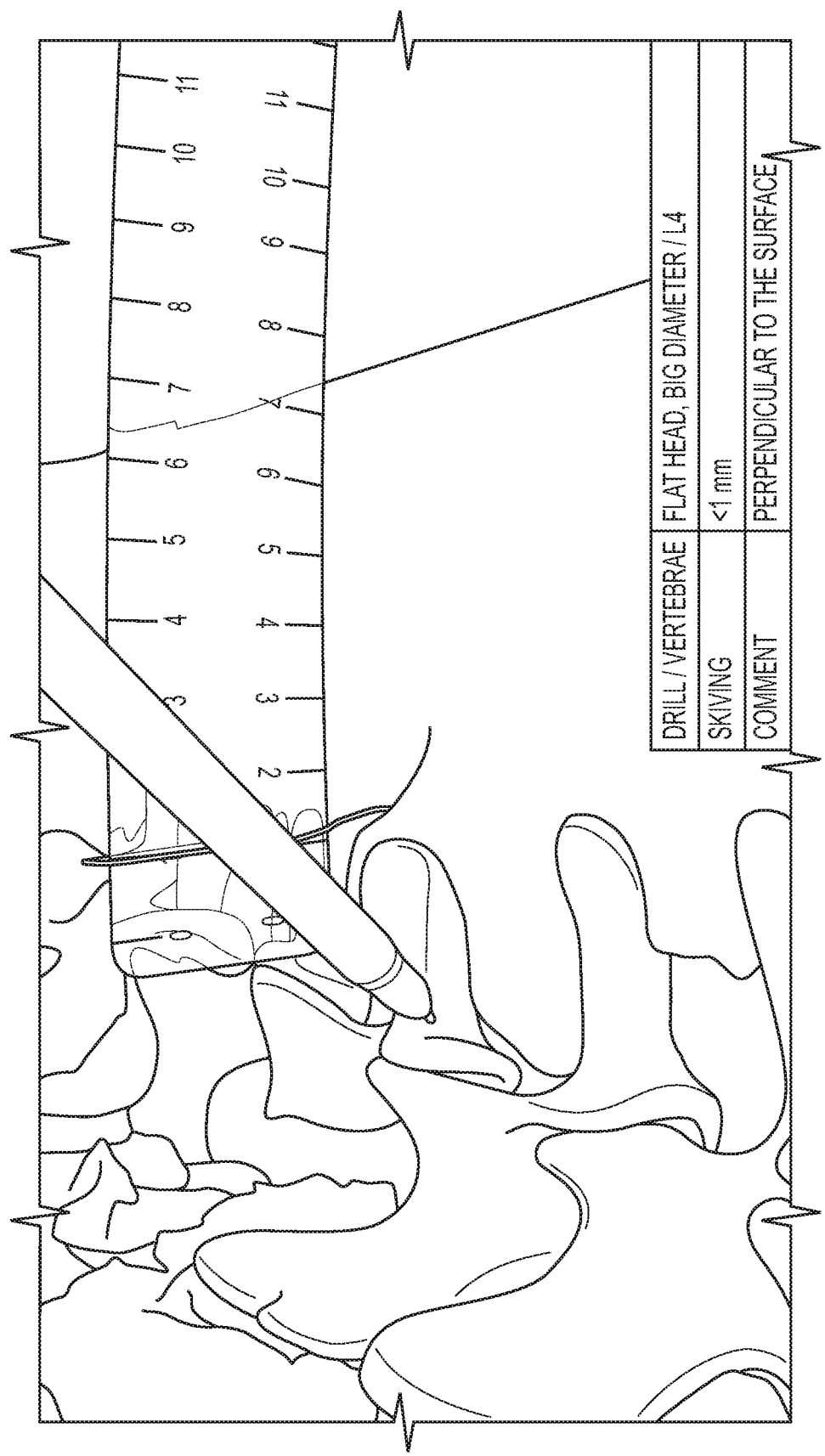
FIG. 16 is a still photograph taken during an experiment performed using the disclosed technology and standard drill bits to measure the amount of skiving experienced with different drill bit designs.
Figure 17:
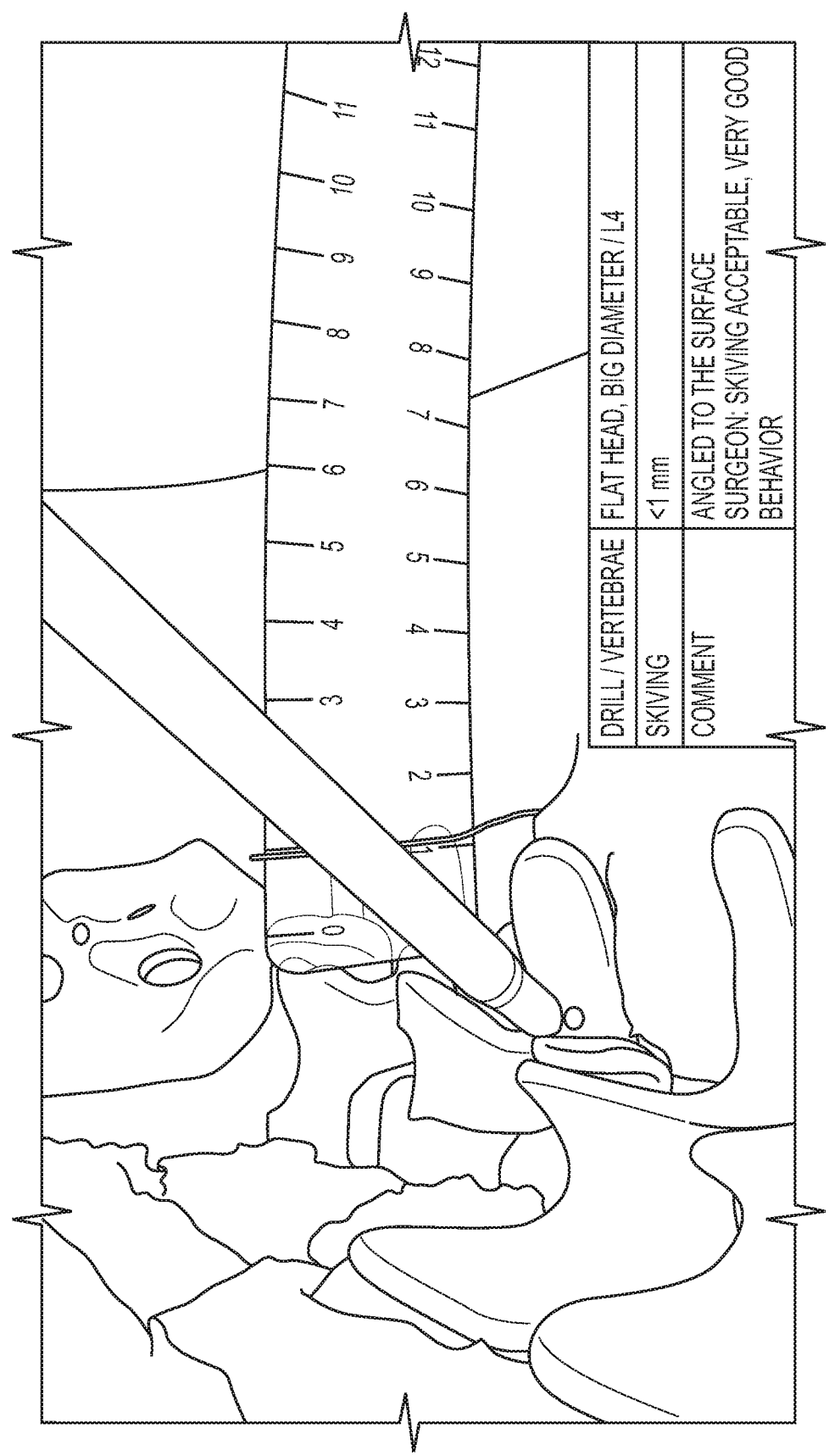
FIG. 17 is a still photograph taken during an experiment performed using the disclosed technology and standard drill bits to measure the amount of skiving experienced with different drill bit designs.
Figure 18:
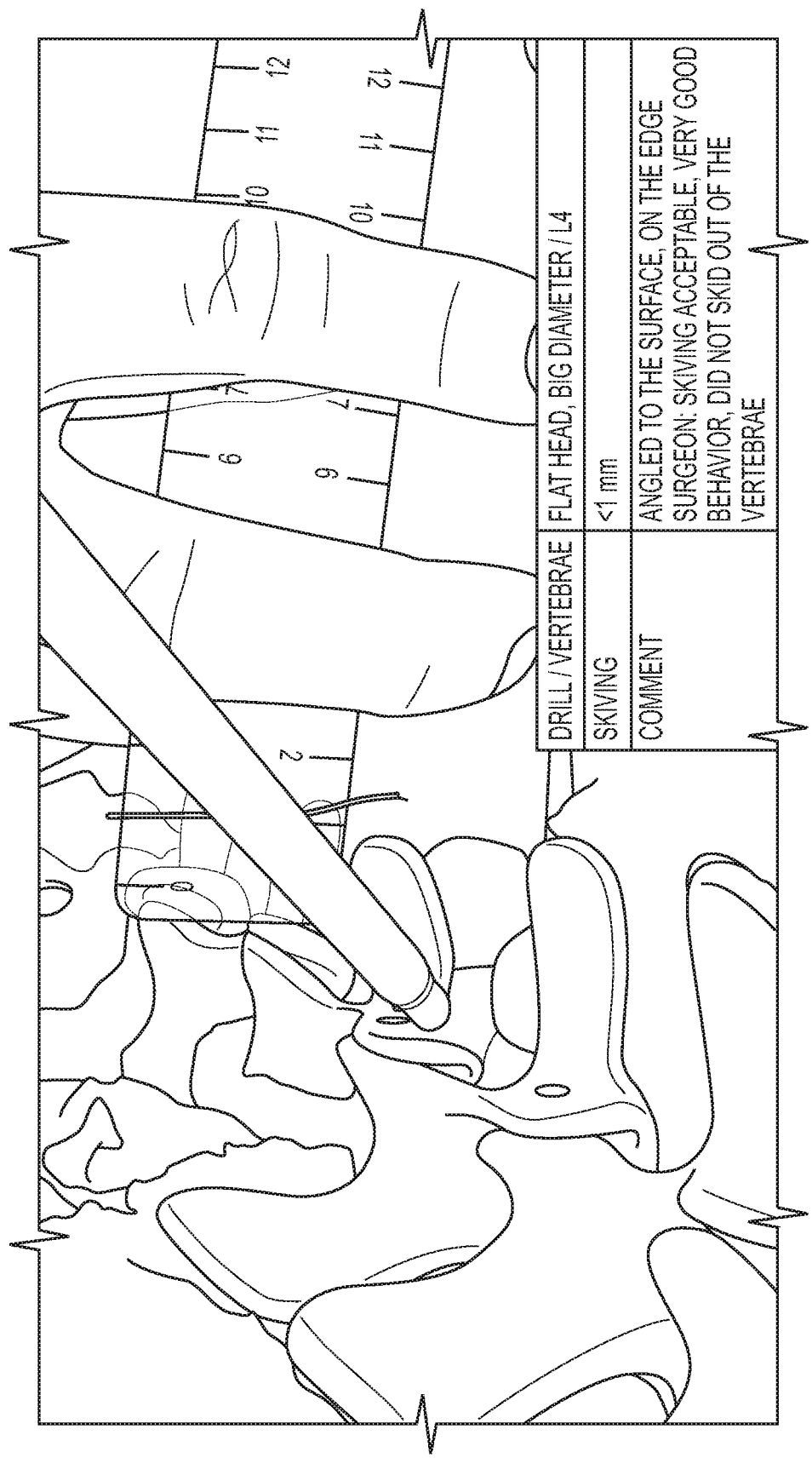
FIG. 18 is a still photograph taken during an experiment performed using the disclosed technology and standard drill bits to measure the amount of skiving experienced with different drill bit designs.
Figure 19:
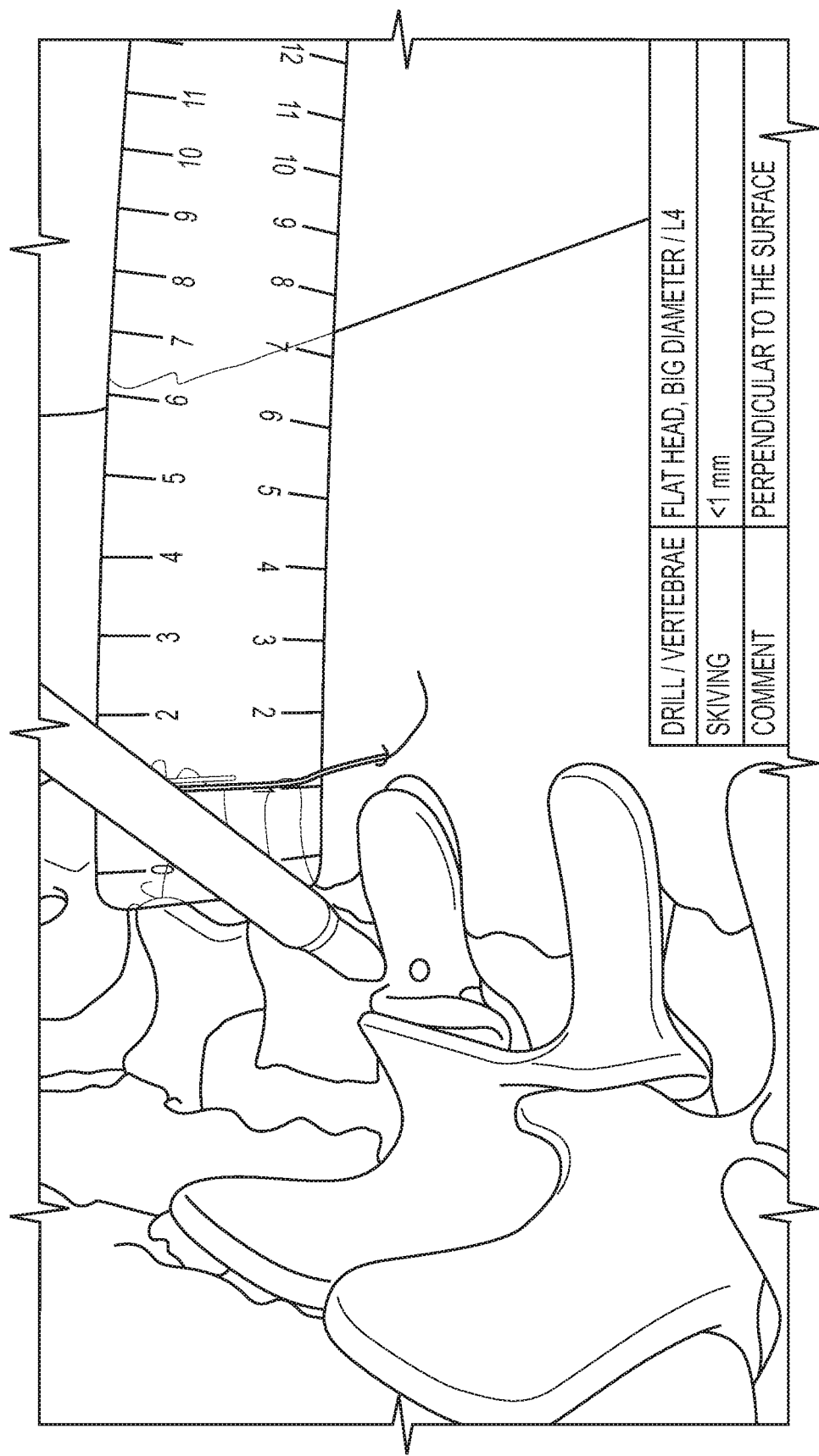
FIG. 19 is a still photograph taken during an experiment performed using the disclosed technology and standard drill bits to measure the amount of skiving experienced with different drill bit designs.
Figure 20:
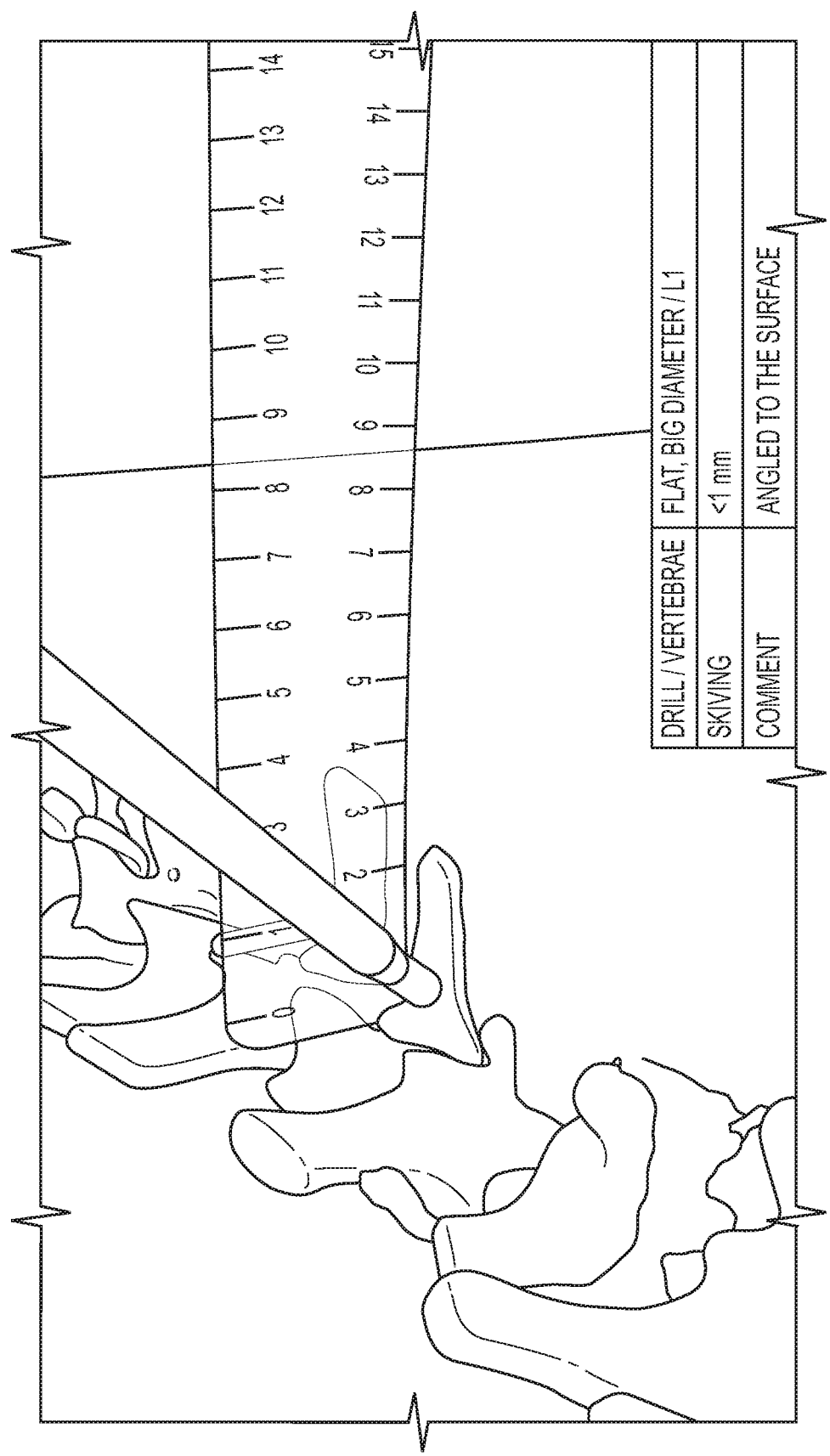
FIG. 20 is a still photograph taken during an experiment performed using the disclosed technology and standard drill bits to measure the amount of skiving experienced with different drill bit designs.
Figure 21:
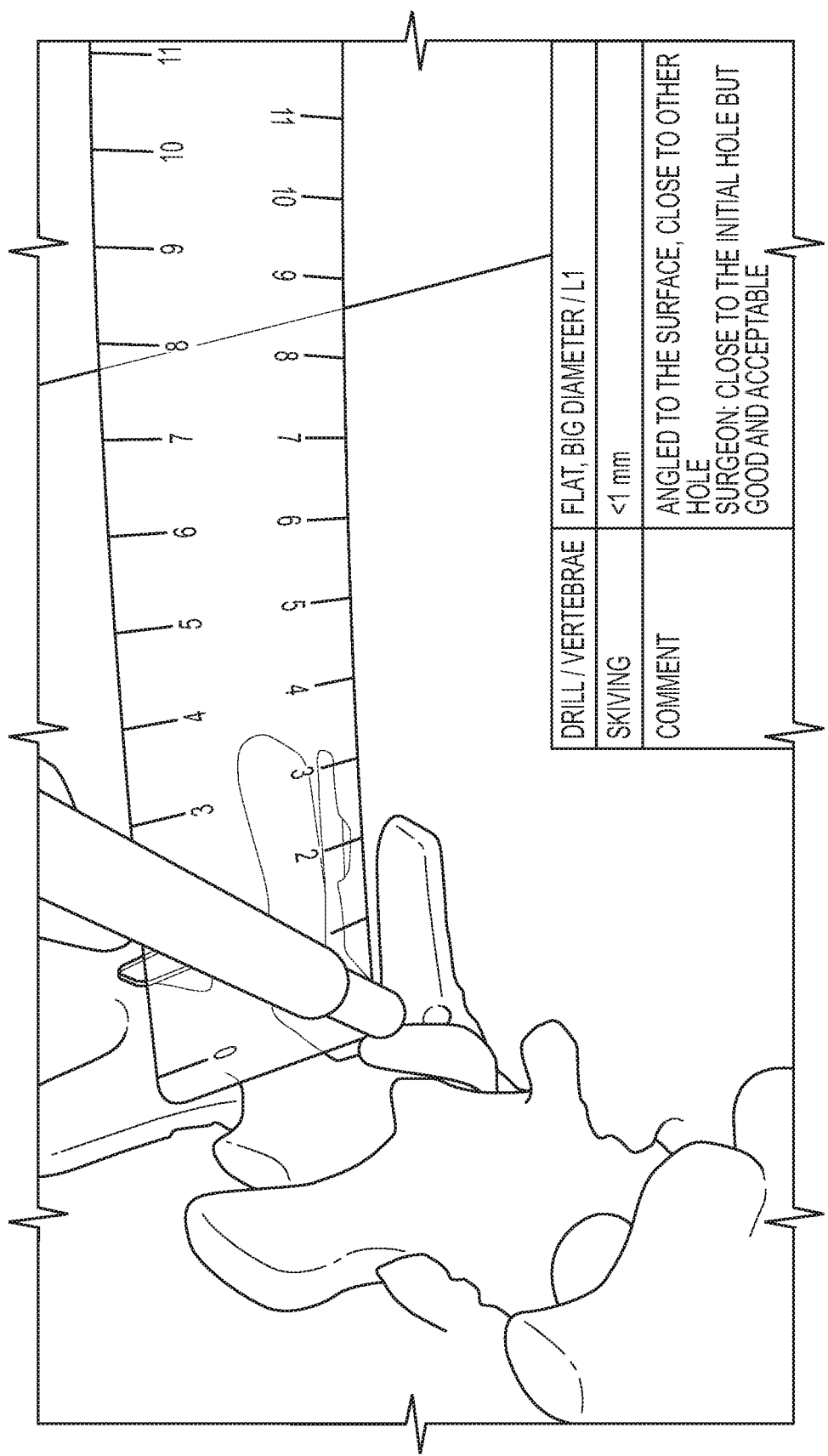
FIG. 21 is a still photograph taken during an experiment performed using the disclosed technology and standard drill bits to measure the amount of skiving experienced with different drill bit designs.
Figure 22:
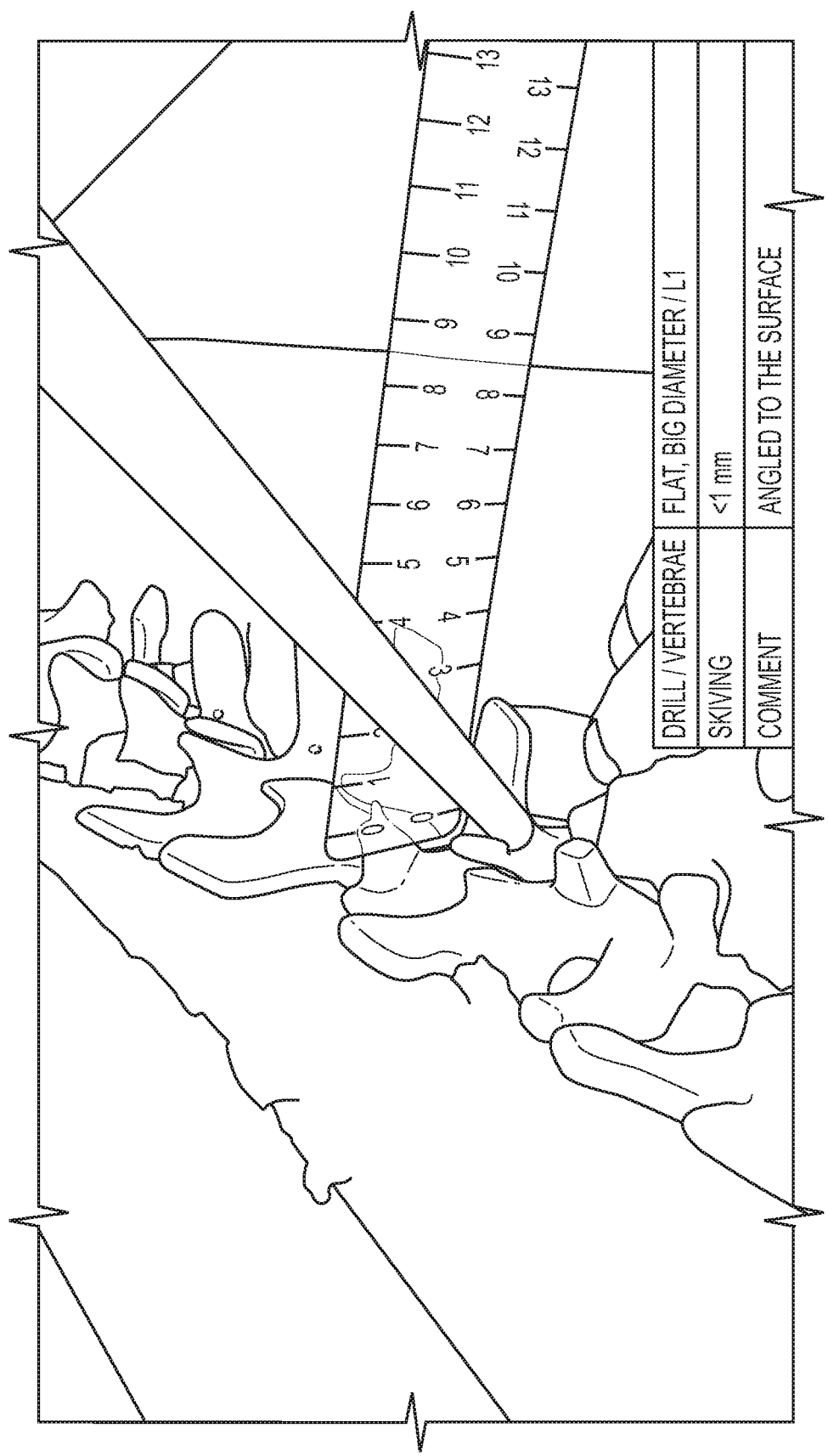
FIG. 22 is a still photograph taken during an experiment performed using the disclosed technology and standard drill bits to measure the amount of skiving experienced with different drill bit designs.
Figure 23:
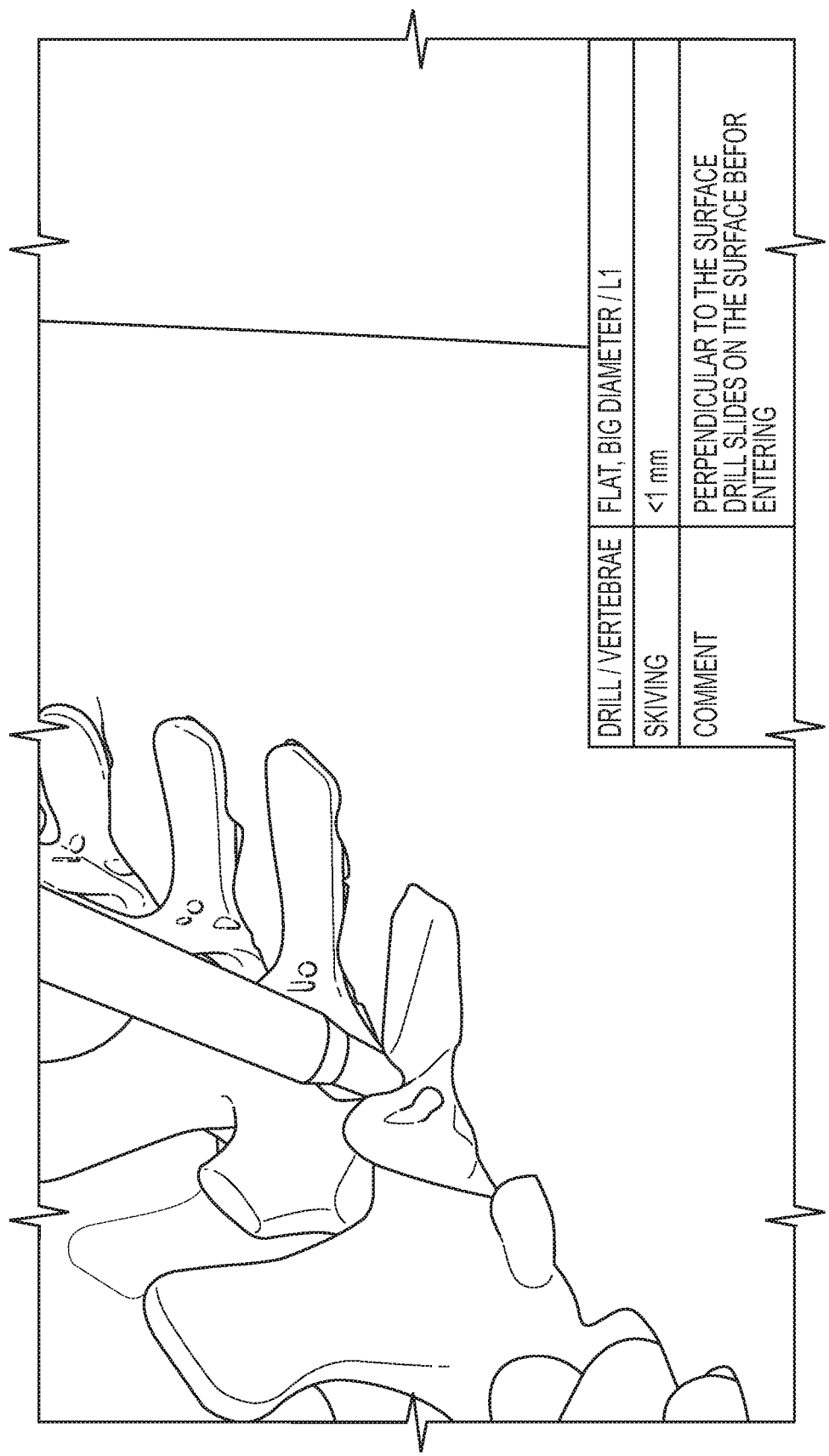
FIG. 23 is a still photograph taken during an experiment performed using the disclosed technology and standard drill bits to measure the amount of skiving experienced with different drill bit designs.
Figure 24:
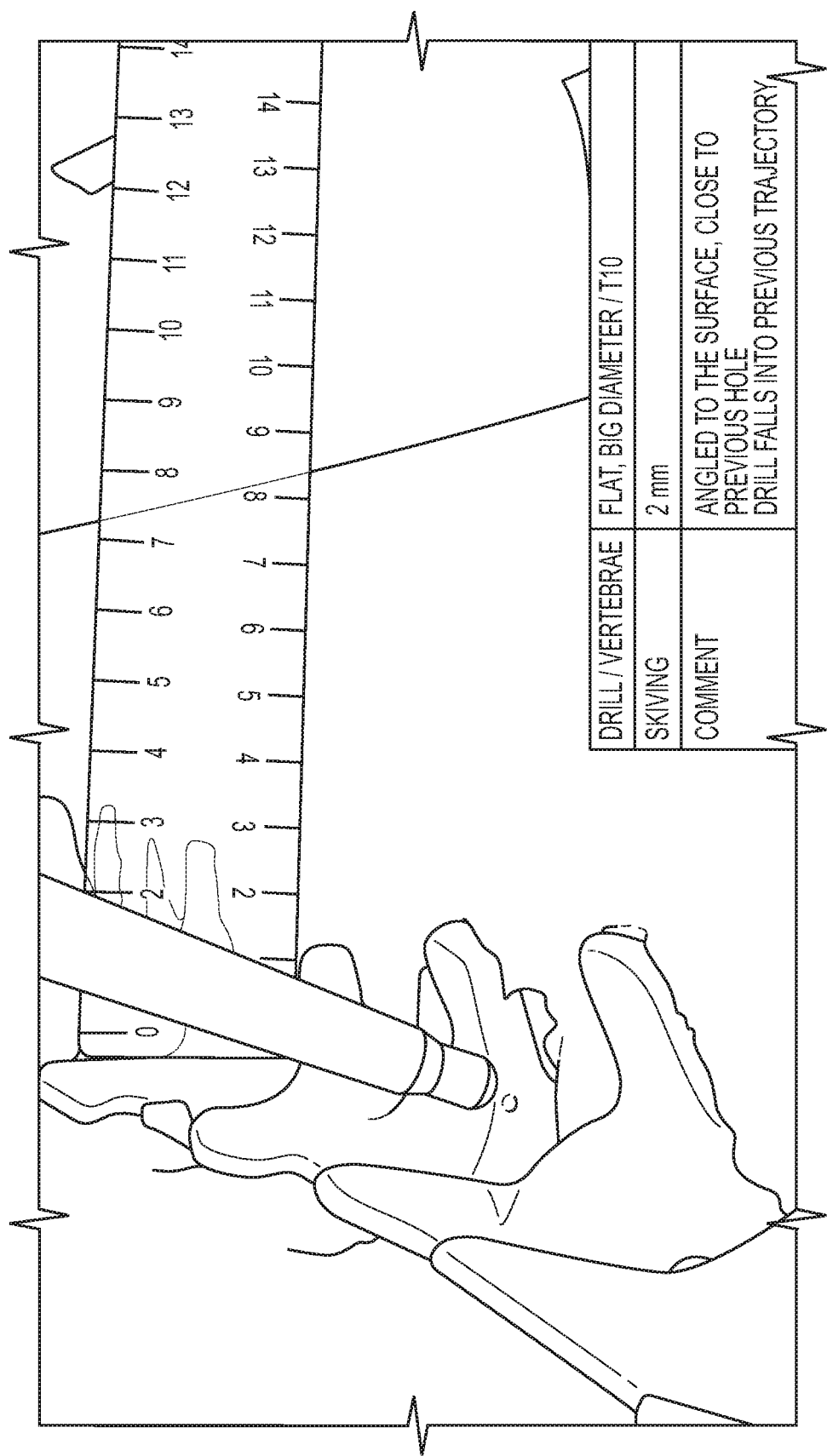
FIG. 24 is a still photograph taken during an experiment performed using the disclosed technology and standard drill bits to measure the amount of skiving experienced with different drill bit designs.
Figure 25:
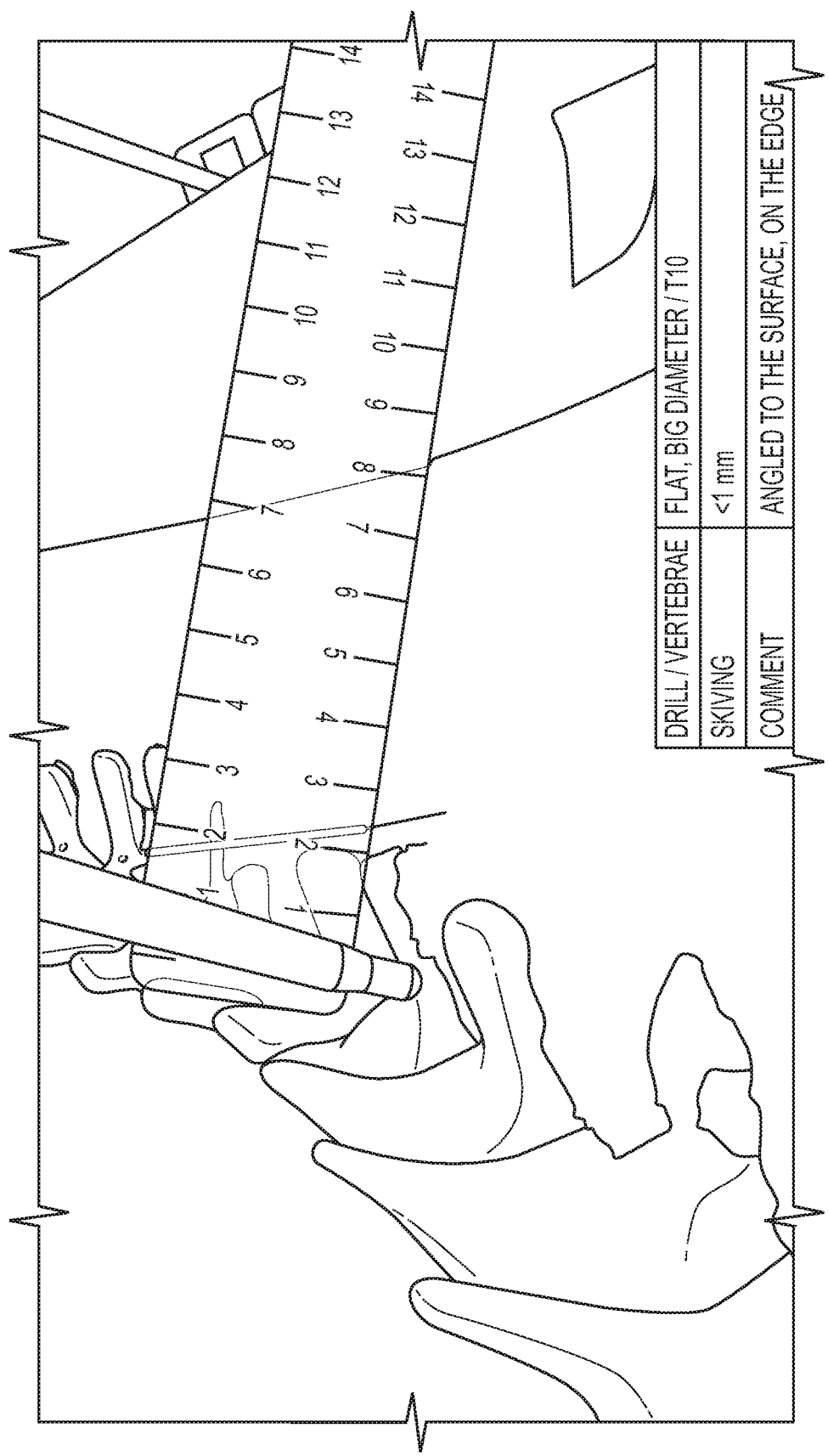
FIG. 25 is a still photograph taken during an experiment performed using the disclosed technology and standard drill bits to measure the amount of skiving experienced with different drill bit designs.
Figure 26:
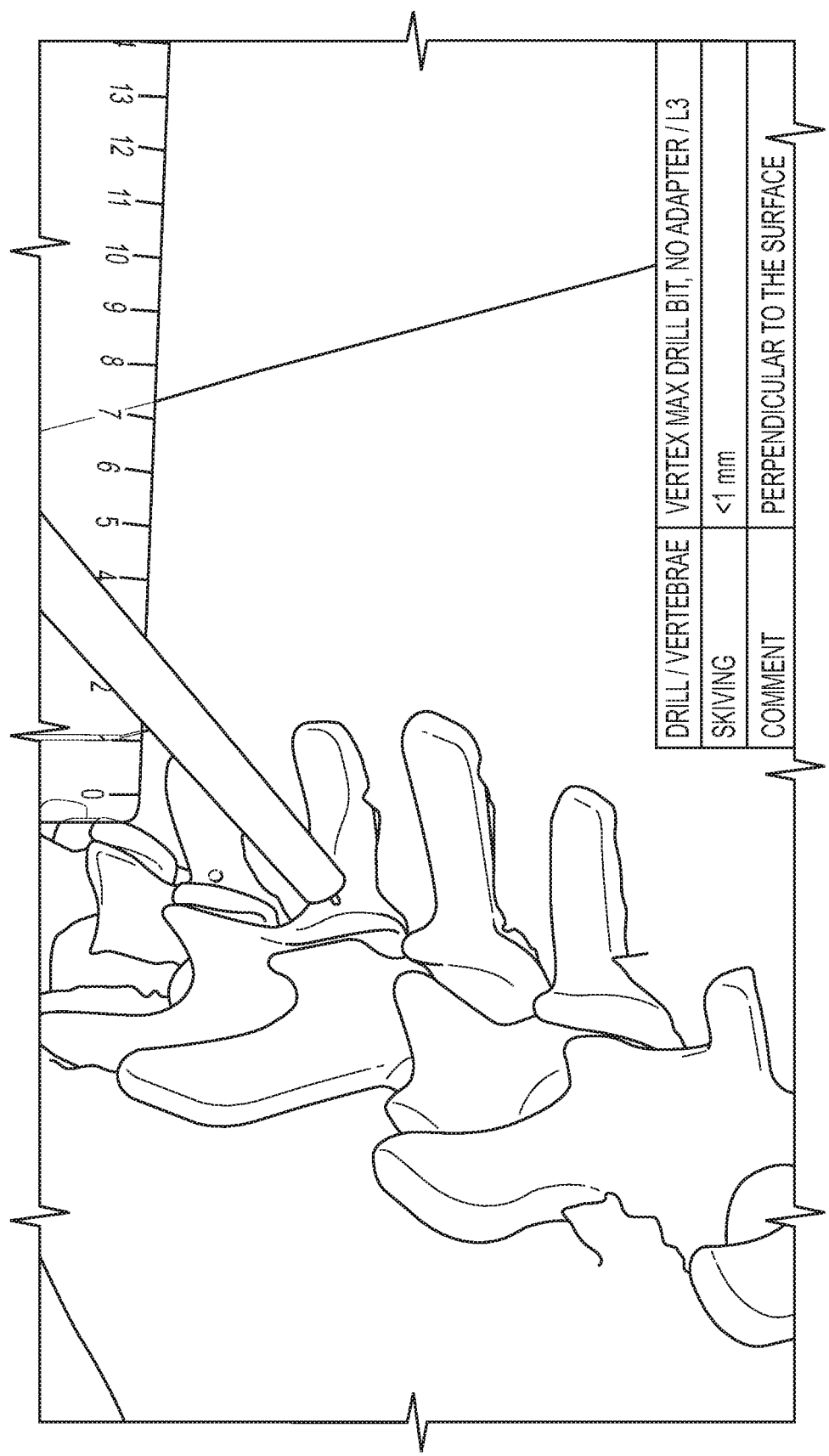
FIG. 26 is a still photograph taken during an experiment performed using the disclosed technology and standard drill bits to measure the amount of skiving experienced with different drill bit designs.
Figure 27:
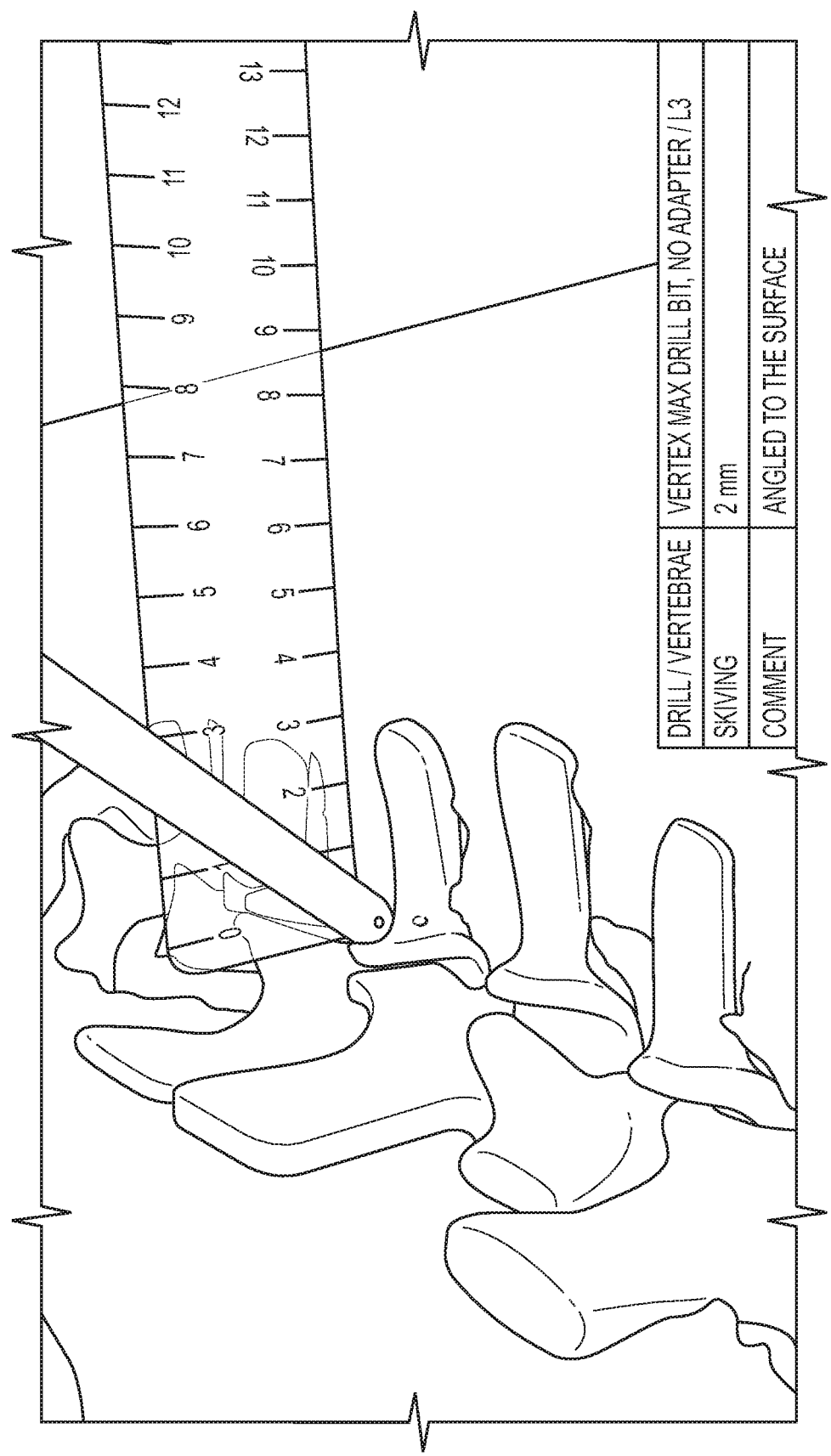
FIG. 27 is a still photograph taken during an experiment performed using the disclosed technology and standard drill bits to measure the amount of skiving experienced with different drill bit designs.
Figure 28:
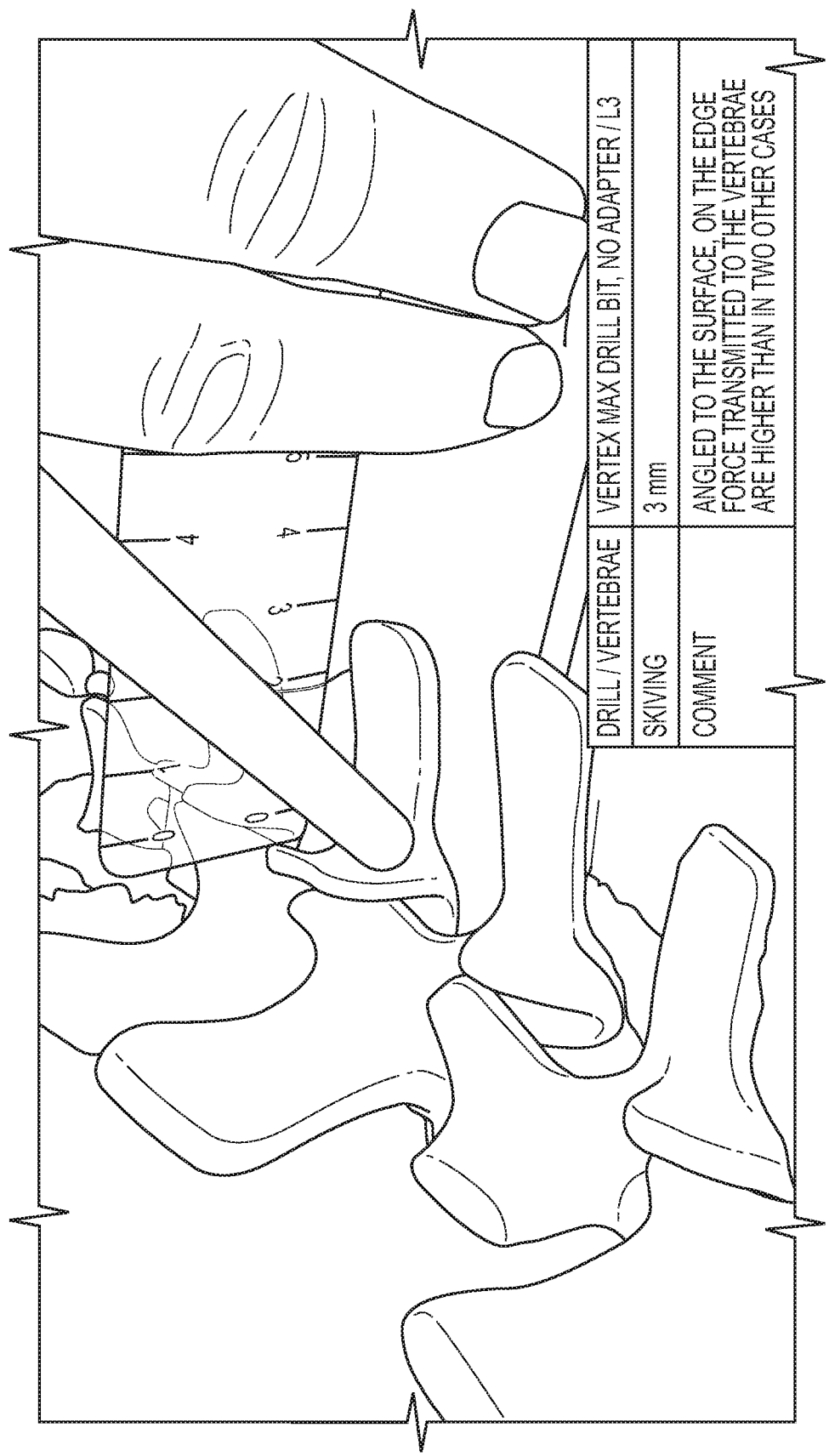
FIG. 28 is a still photograph taken during an experiment performed using the disclosed technology and standard drill bits to measure the amount of skiving experienced with different drill bit designs.
Figure 29:
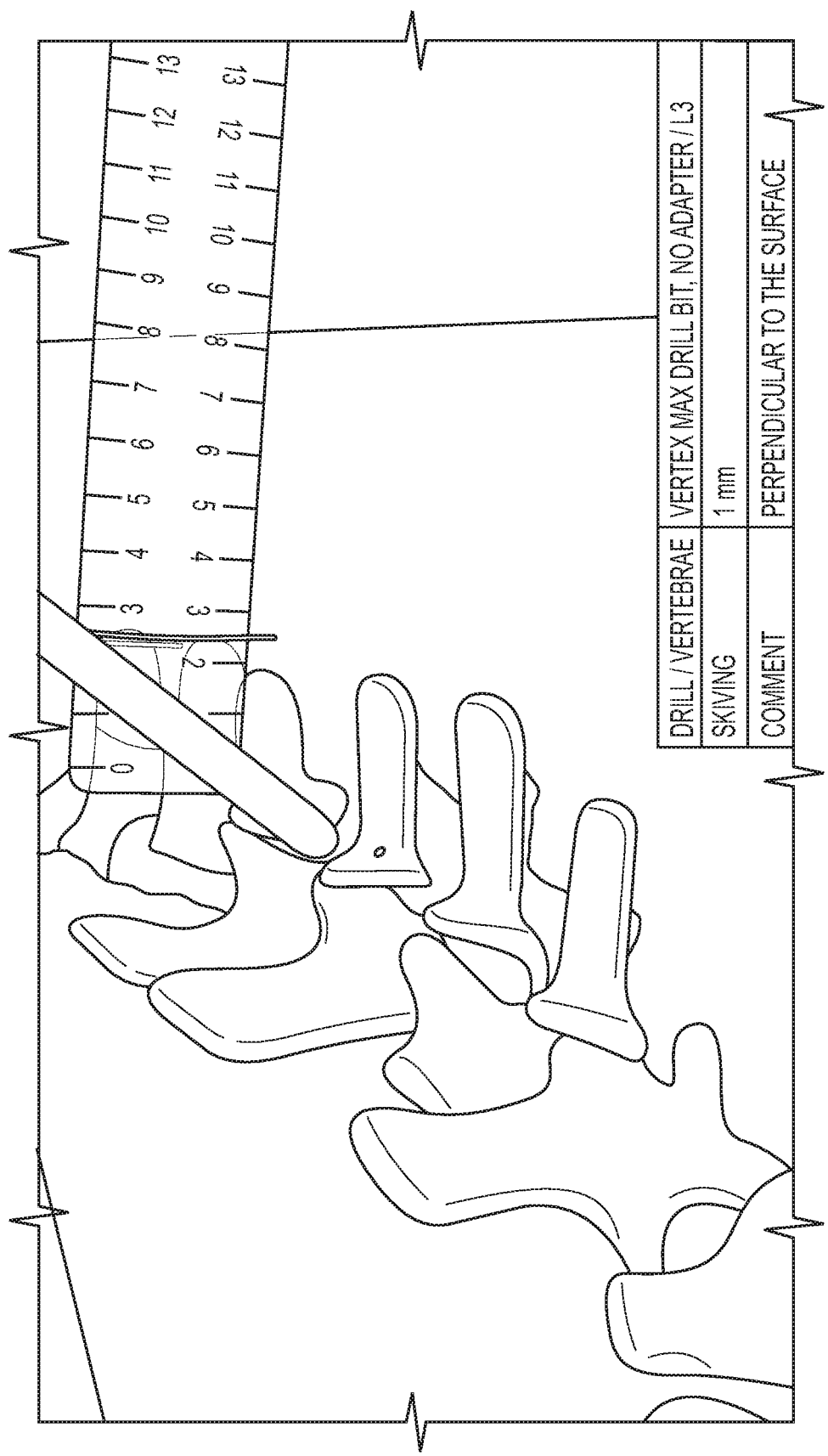
FIG. 29 is a still photograph taken during an experiment performed using the disclosed technology and standard drill bits to measure the amount of skiving experienced with different drill bit designs.
Figure 30:
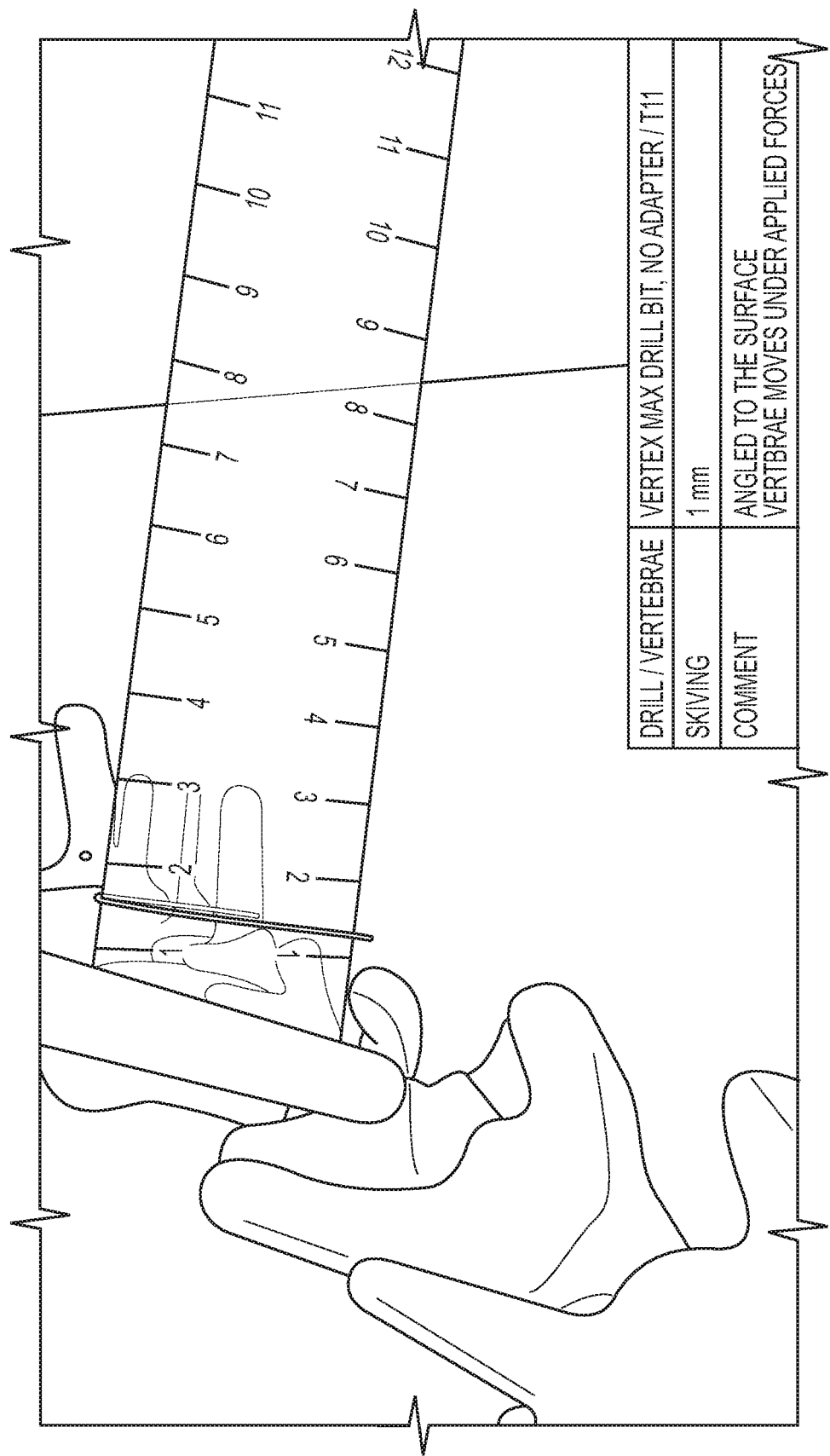
FIG. 30 is a still photograph taken during an experiment performed using the disclosed technology and standard drill bits to measure the amount of skiving experienced with different drill bit designs.

FIG. 5 is a photograph of different types of drill bits tested during this experiment. An anti-skid drill-bit in accordance with the disclosed technology is shown as drill bit 502. It comprises a body similar to a standard drill bit and a flat end (rather than a pointy end) in accordance with an embodiment of the invention. Drill bit 504 (e.g., Drill Bit for Universal Drill Bit Guide by Medtronic of Minneapolis, Minn.) and drill bit 506 (e.g., Vertex® Max Drill Bit by Medtronic of Minneapolis, Minn.) are commercially available drill bits.

FIGS. 6 through 30 a images from a series of drilling movies captured during the experiment. Recording was done using a high-frequency camera (128 fps) for greater precision. The visible ruler in the background allowed for estimating displacements of various elements. All drilling was done by the surgeon. Trajectories were planned in the way that emphasizes possible skiving situations while being clinically relevant. Such situations are: angles surface (i.e. not perpendicular to the drill bit axis), on the bone edge, close to other existing hole.

FIGS. 6 through 15 are images captured during experiments conducted with drill bit 504. Experiments with drill bit 504 (a standard drill bit represented by a small diameter, sharp drill bit) illustrated no skiving if drill bit is perpendicular to the drilled surface. However, there was significant skiving (+5 mm) on angled surfaces which can lead to imprecise drilled holes and extra-pedicular holes (i.e., holes outside pedicle either medial (spinal canal, can lead to paralysis) or lateral (vascular system, can lead to death)).

FIGS. 16 through 25 are images captured during experiments conducted with drill bit 502 (flat head, big diameter) which was constructed in accordance with an embodiment of this invention. Experiments with anti-skiving drill bit 502 illustrated acceptable skiving (≤1 mm) in drilling to all surfaces (perpendicular and angled). Experiments showed that the anti-skive drill bit 502 can drill in proximity of previous holes without falling into them and the bit 502 can jitter on the flat surface before penetrating into bone (i.e., ski before penetrating into bone). With optimized drill bit shape (e.g., the drill bit shown in FIG. 32A or FIG. 32B), the performance of this function shall improve.

FIGS. 26 through 30 are images captured during experiments conducted with drill bit 506 (represented by Vertex Max drill bit in the experiment). Experiments with anti-skiving drill bit 506 found less skiving than for standard drill bit 504, but greater skiving than the anti-skiving drill bit 502. Additionally, the drill bit transmitted higher forces to the vertebrae. Thus, as shown in the experiments, the disclosed technology provides drill bits that reduce or eliminate unwanted skiving to less than conventional drill bits.

Figure 31:
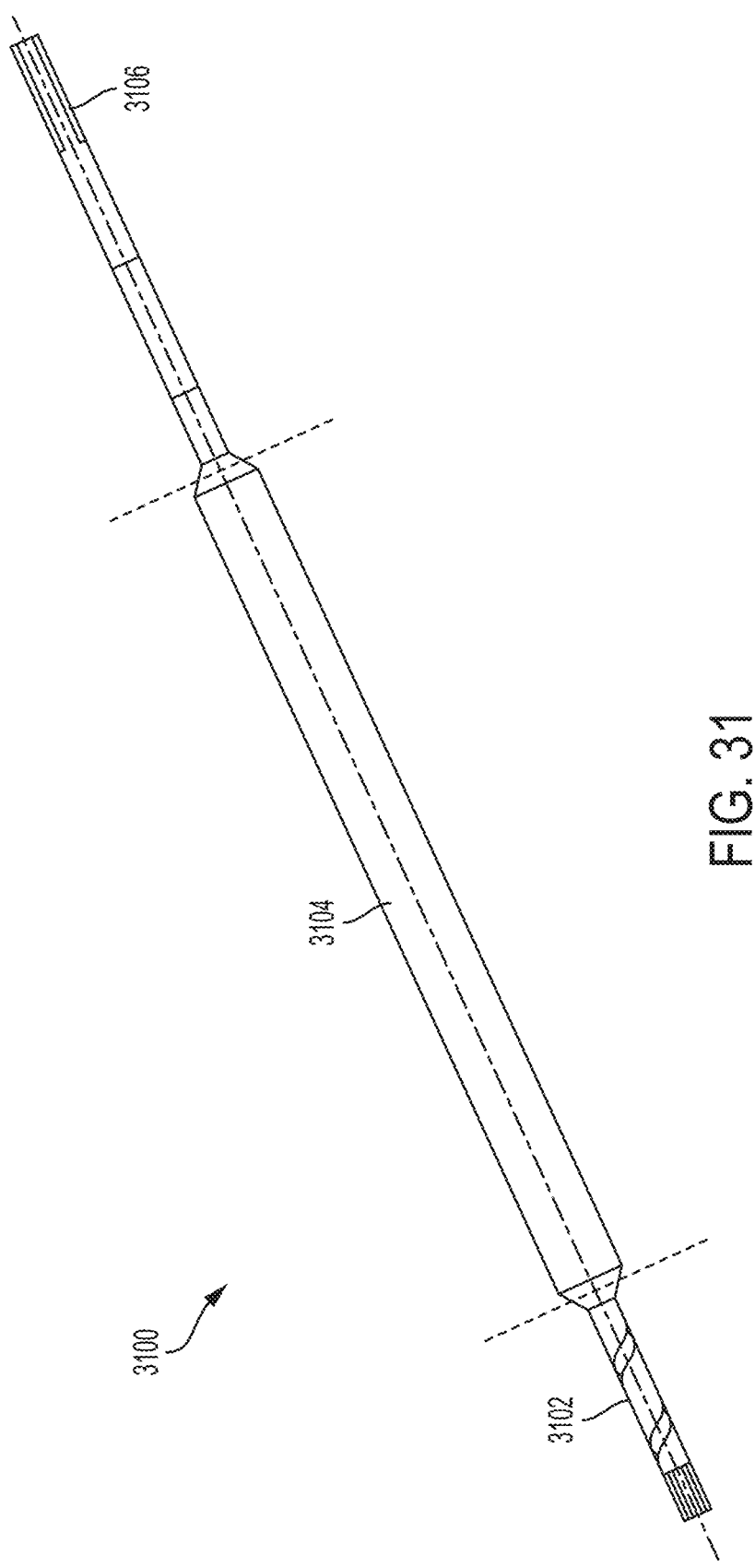
FIG. 31 illustrates an anti-skive drill bit in accordance with embodiments of the disclosed technology.

FIGS. 31 through 35C illustrate anti-skive drill bits in accordance with embodiments of the disclosed technology. In certain embodiments, as illustrated in FIG. 31, a drill bit 3100 in accordance with an embodiment of the disclosed technology includes a drilling part 3102 for creating a hole and evacuate material as the hole is created, a guiding part 3104 that interacts with a guide (e.g., held by a robot), and an attachment part 3106 (e.g., a shank) that can be inserted into and/or securely held by a drill. As discussed above, the drill bit 3100 has a milling head 3108.

Figure 32A:
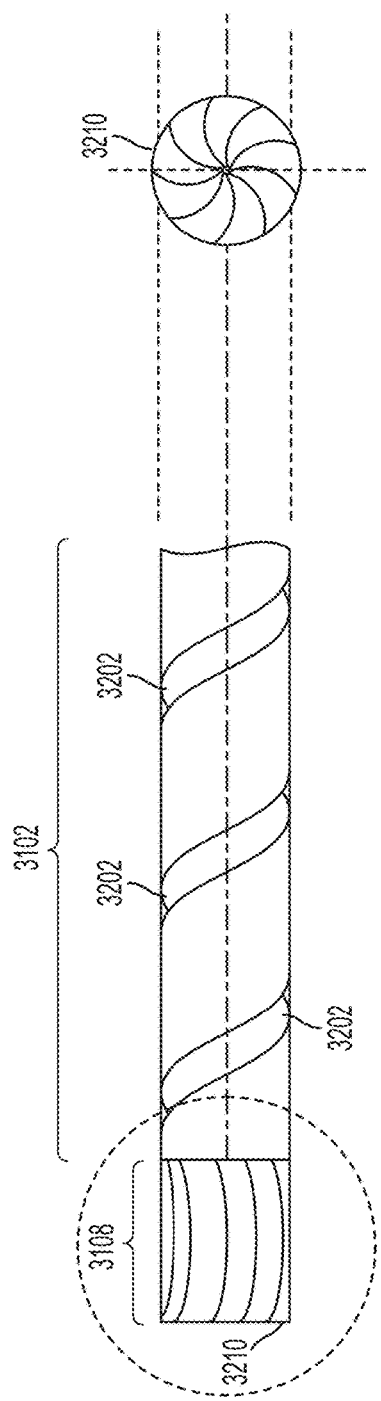
FIG. 32A and FIG. 32B illustrate anti-skive drill bits in accordance with embodiments of the disclosed technology.
Figure 32B:
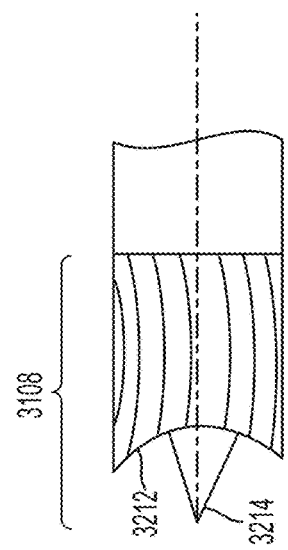

In certain embodiments, as shown in FIGS. 32A and 32B, the drilling part 3102 has flutes 3202 along the side of the body. These flutes 3202 evacuate material as a hole is drilled. The front face 3210 may be flat and/or have front-cutting surfaces 3210. Additionally, a portion of the body 3108 between the front face and the flutes can have side-cutting surfaces (e.g., milling faces). An alternative front face device includes a concave shape 3212 with a spike 3214 to better guide on flat faces of bone. The spike 3214, in this embodiment, is centered on the front face.

Figure 33A:
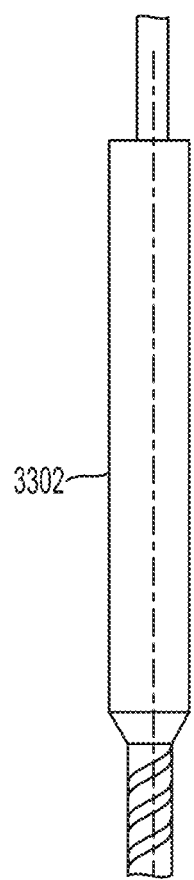
FIG. 33A and FIG. 33B illustrate anti-skive drill bits in accordance with embodiments of the disclosed technology.
Figure 33B:
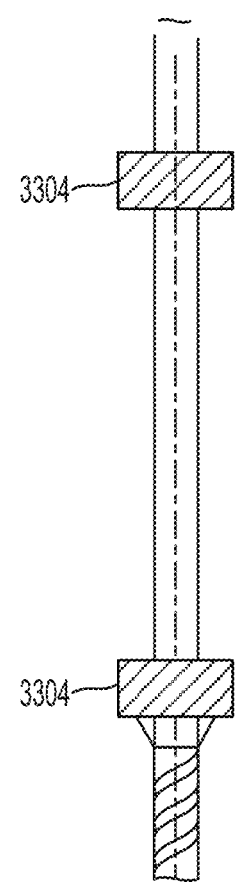

In certain embodiments, as shown in FIGS. 33A and 33B, the drill bit includes a guiding part 3104 that interacts with a guide (e.g., held by a robot). The guiding part 3104 is sized to fit into a guide without an adapter. The guiding part 3104 may consisting of a single cylindrical body 3302 as shown in FIG. 33A along the length of the drill bit that has a diameter to fit into a guide. In an alternative embodiment, the guiding part includes two cylindrical parts 3304 as shown in FIG. 33B, each with a diameter to fit into a guide. The two guiding parts are separated by a portion of the drill bit body extending therebetween with a smaller diameter than the guiding parts.

Figure 34:
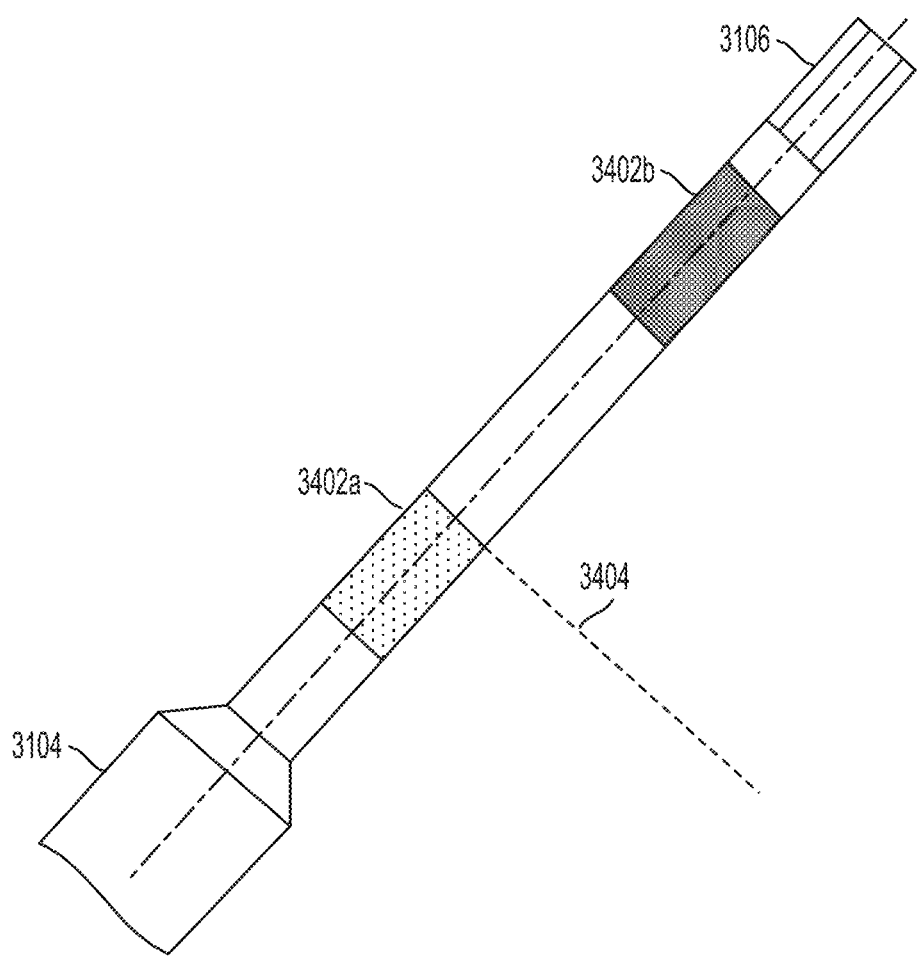
FIG. 34 illustrates an anti-skive drill bit in accordance with embodiments of the disclosed technology.

In certain embodiments, as shown in FIG. 34, between the drill attachment part 3106 of the drill bit and the guide part 3104 of the drill bit, the body of the drill bit has markings 3402*a-b* to assist a user in preparing holes in a bone. The markings 3402*a-b* can be notches, colorings, bands, or other indicators. The marking 3402*a* indicates when to start drill rotation (e.g., before contact with bone). An additional marking 3402*b* indicates when to stop drill rotation and/or stop depth penetration in the bone. The top side of the marking 3402*a* can indicate when the drill bit will begin exiting the guide. In certain embodiments, depth control can include a separate depth controller 3506 that attaches to the drill bit 3502 as shown in FIG. 35A, FIG. 35B, and FIG. 35C. The depth controller 3506 can sit on one or more notches 3508 on the drill bit 3502 and be tightened to control the depth the drill bit 3502 will extend beyond drill bit guide 3604, thereby controlling the depth of penetration in the patient.

Figure 36:
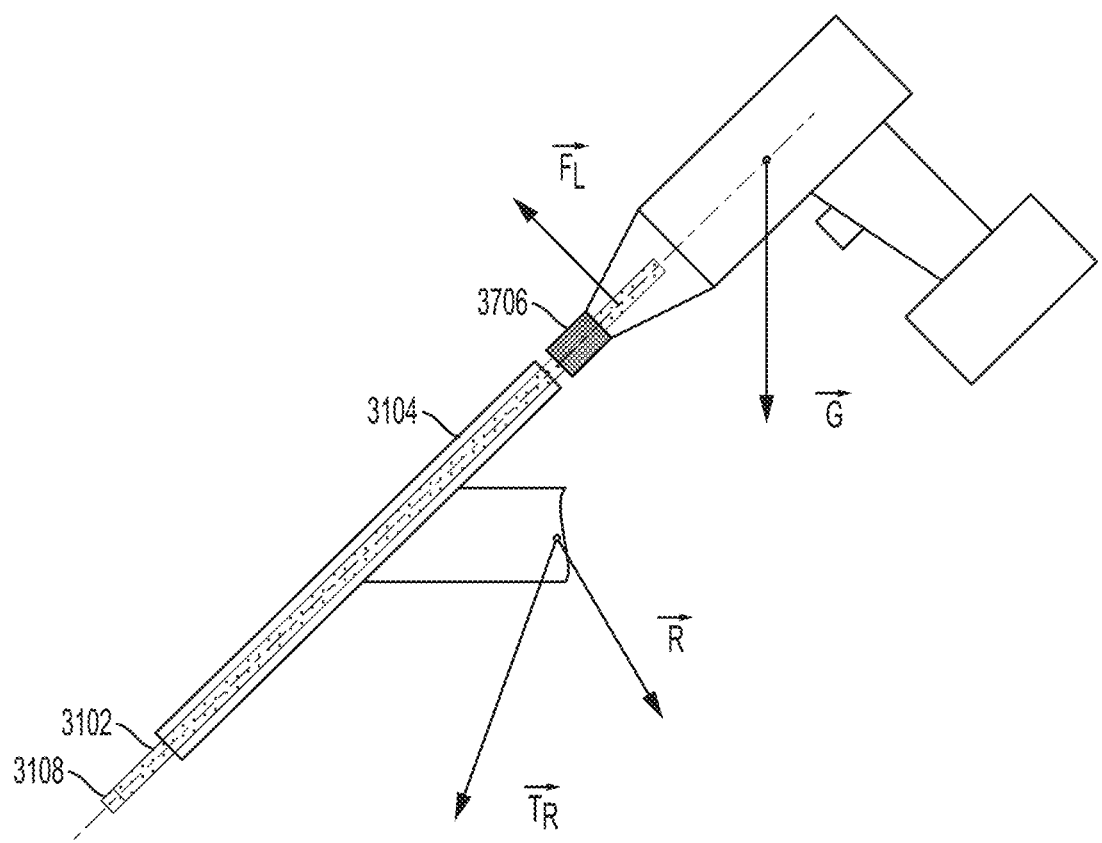
FIG. 36 illustrates a problem solved by use of a compliant part as described in relation to FIGS. 37A through 39C.

FIG. 36 illustrates a set-up for describing the problem solved by a compliant part as described in relation to FIGS. 37A through 39C. A drill guide is held by the robot represented by robot attachment. A drill bit is fixed to the surgical drill which gives drill bit rotation. Typically the surgical drill is hand held by the surgeon. A surgeon inserts drill bit into guide and drills hole in patient anatomy/bone (could be any bone, including vertebrae, cranial, and/or standard orthopedic surgery).

A surgical drill can have significant weight (e.g., a few kilograms even) which makes gravitation force G shown in FIG. 36 high. Additionally, drill rotation as well as forces applied by surgeon give forces $F_L$. These forces generate high reactions at the robot attachment represented by reaction force R and torque $T_R$. These high reactions put high load on robot part and guided instruments. Additionally, they can introduce imprecisions when guiding. To solve these problems, in certain embodiments, a compliant part (e.g., on or part of the drill bit) is used which allows the insertion movement while transmitting less reaction forces from the drill and drill bit system to the robot and guide.

Figure 38:
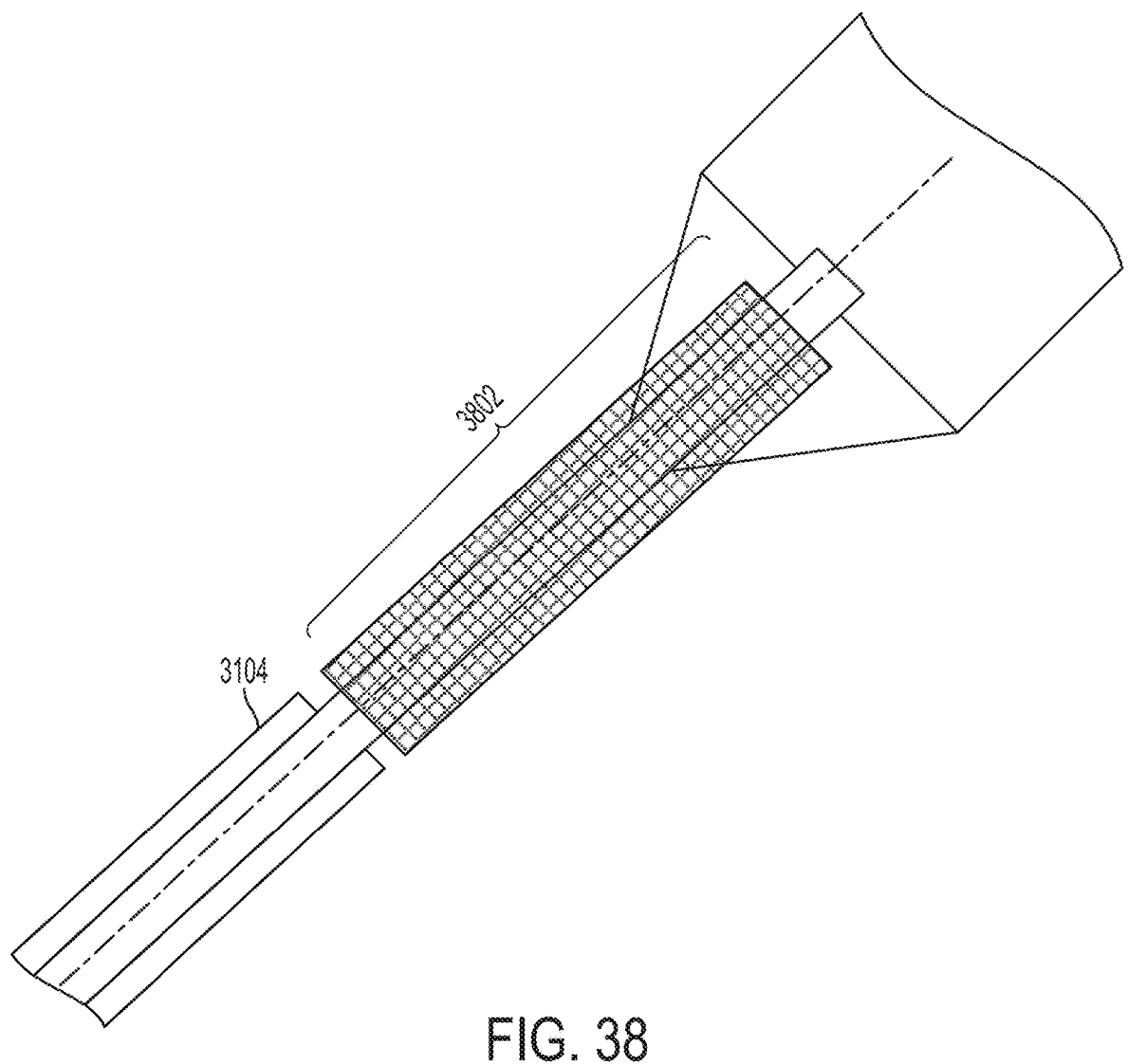
FIG. 38 illustrates an example compliant part in accordance with an embodiment of the invention.

FIG. 37A and FIG. 37B are illustrations of portions of drill bits in accordance with embodiment s of the invention. In this example, the drill bit includes one or more compliant parts (e.g., made of rubber). In some cases, it is difficult to hold the drill in line with the guide. One or more compliant parts increases the tolerance to these errors. As shown in FIG. 37A, the compliant part 3706 is used to connect first portion 3104 of the drill bit to a second portion 3106 of the drill bit. In an alternative embodiment, as shown in FIG. 37B, the compliant part 3708 extends around and/or covers at least a portion of the drill attachment part of the drill bit. In certain embodiments, both compliant part 3706 and compliant part 3708 are used. FIG. 38 illustrates a zone 3802 where the compliant part can be placed along the shaft of the drill bit. In certain embodiments, the compliant part can be located on the drill bit shaft and/or on the interface between drill bit and surgical drill.

Figure 39A:
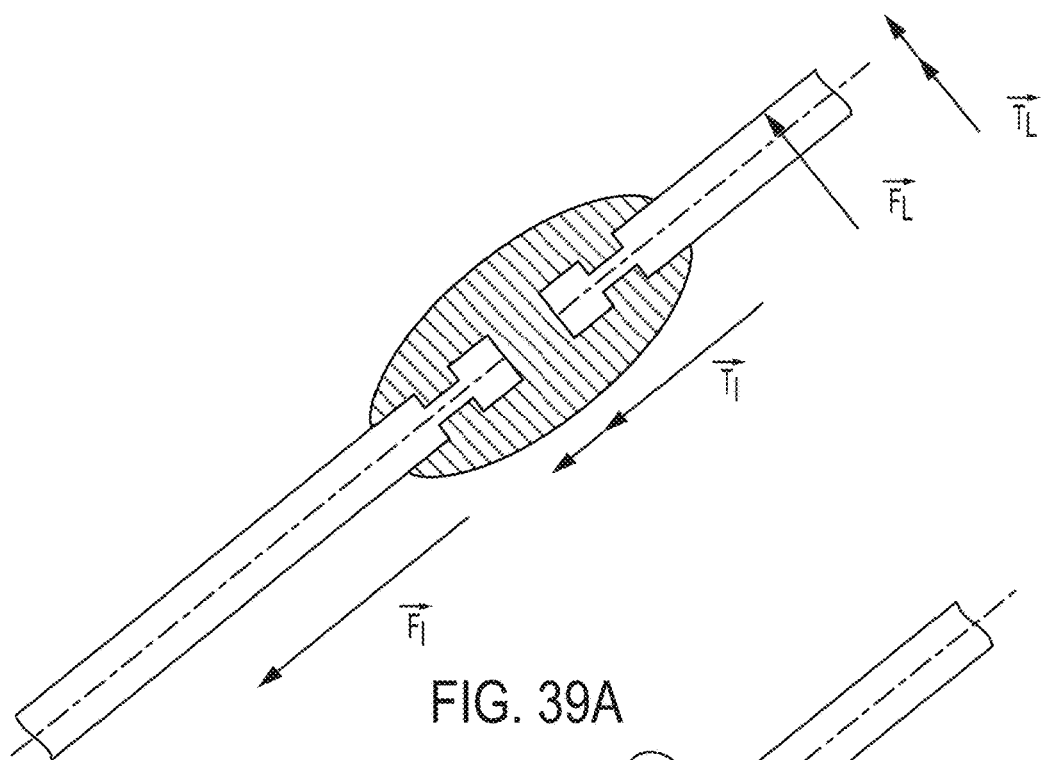
FIG. 39A, FIG. 39B, and FIG. 39C illustrate example compliant parts in accordance with an embodiment of the invention.
Figure 39B:
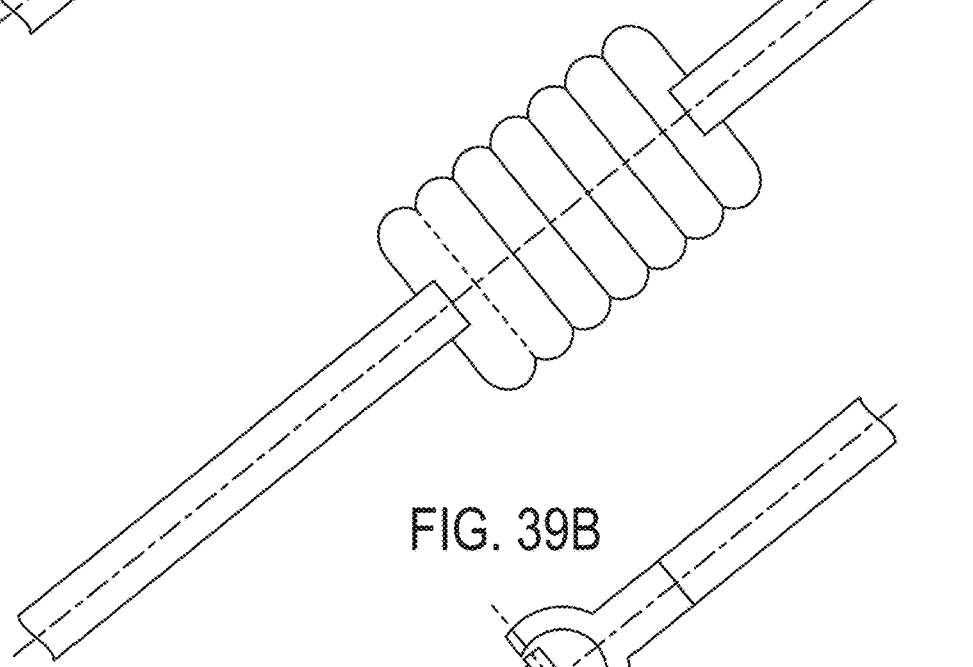
Figure 39C:
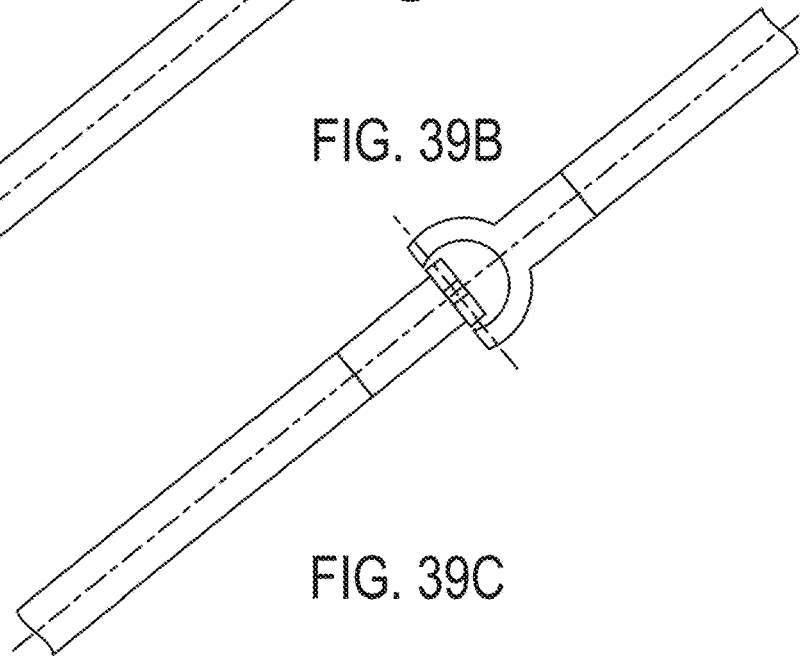

FIG. 39A, FIG. 39B, and FIG. 39C illustrate various embodiments of a drill bit that includes a compliant part. The embodiment shown in FIG. 39A uses a compliant part made of elastic material, such as rubber. The embodiment shown in FIG. 39B uses a bellow as the compliant part, such as a metal bellow, is used to provide compliance. The embodiment shown in FIG. 39C uses a standard universal joint is used to allow for compliance.

Figure 40:
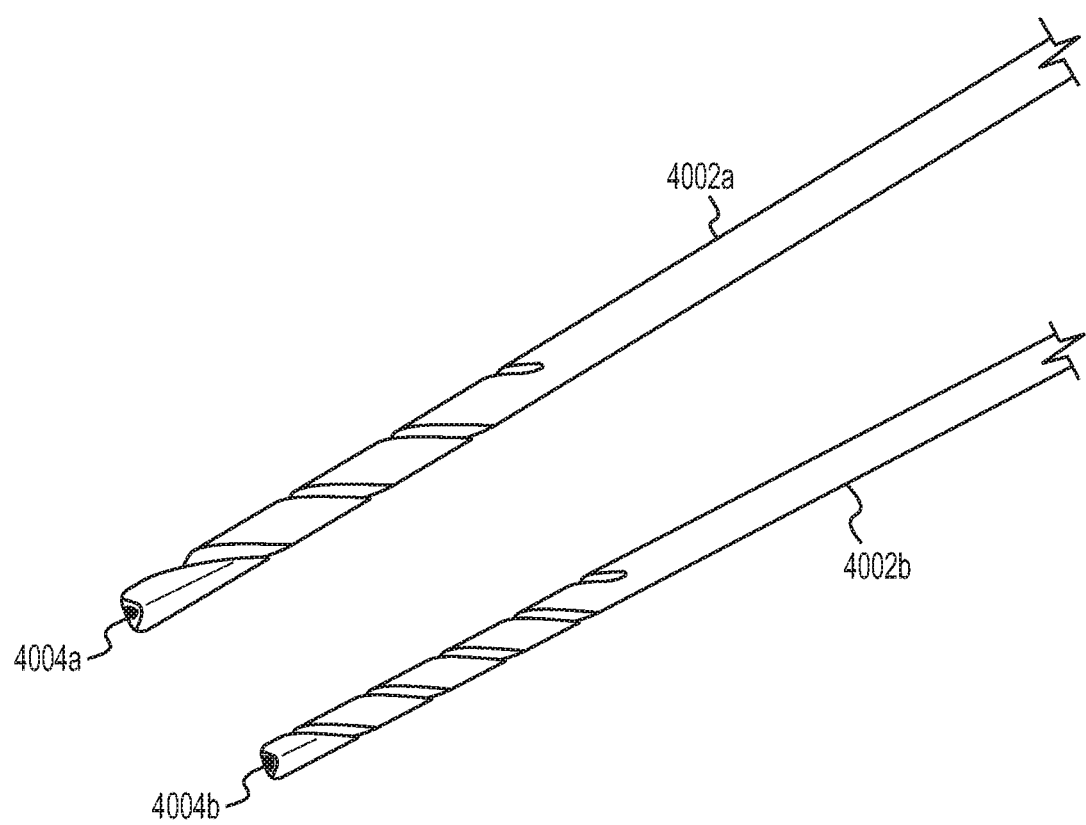
FIG. 40 is an illustration of cannulated drill bits.

FIG. 40 is an illustration of cannulated drill bits 4002*a* and 4002*b*. In certain embodiments, the drill bits disclosed herein are cannulated. In certain cases, surgeons prefer to use k-wires to provide guidance between various stages of the surgery. An example workflow is described in relation to, for example, FIG. 2A, FIG. 2B and FIG. 9A of U.S. Patent Application Publication No. 2016/0235492, filed Feb. 18, 2016, entitled "Systems and Methods for Performing Minimally Invasive Spinal Surgery with a Robotic Surgical System using a Percutaneous Technique", the contents of which are hereby incorporated by reference in their entirety. To implement such workflow, a cannulation 4004*a*, 4004*b* (i.e., a throughput hole adapted to the size of the k-wire, also called guide wire) can be created in the drill bit 4002*a*, 4002*b*.

In view of the structure, functions and apparatus of the systems and methods described here, in some implementations, a system and method for performing surgery with a robotic surgical system are provided. Having described certain implementations of methods and apparatus for supporting a robotic surgical system, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

What is claimed is:

1. An anti-skid surgical instrument for preparing a hole in bone tissue of a patient during surgery, the anti-skid surgical instrument having an elongate structure comprising:
   a mill head at the end of the elongate structure for removing bone tissue with reduced skidding of the surgical instrument upon contact of the anti-skid surgical instrument with the bone tissue, wherein the mill head is configured to be a concave face with a spike centered in the concave face and extending therefrom, and one or more side-cutting flutes about the longitudinal axis of the elongate structure for cutting into bone tissue;
   a shank configured to be inserted into a drill;
   a drilling portion between the mill head and the shank, the drilling portion having one or more drill flutes for evacuating removed bone tissue and a guiding part configured to be held by an end effector of a robotic arm; and
   a depth control.

2. The anti-skid surgical instrument of claim 1, wherein the drilling portion comprises one or more markings to indicate a depth penetration in the bone tissue.

3. The anti-skid surgical instrument of claim 1, wherein the drilling portion comprises one or more colors to indicate a depth penetration in the bone tissue.

4. The anti-skid surgical instrument of claim 1, wherein the depth control comprises a first portion indicating when to start rotation of the anti-skid surgical instrument and a second portion indicating when to at least one of stop rotation and stop depth penetration of the anti-ski surgical instrument.

5. The anti-skid surgical instrument of claim 1, wherein the depth control comprises a depth stop that adjustably attached to the anti-skid surgical instrument such that the depth of penetration of the anti-skid surgical instrument changes as a position of the depth stop is changed.

6. The anti-skid surgical instrument of claim 1, wherein the shank comprises one or more notches and the depth control engages at least one of the one or more notches when attached to the anti-skid surgical instrument.

7. The anti-skid surgical instrument of claim 1, comprising:
   a cannulation in the surgical instrument.

8. The anti-skid surgical instrument of claim 7, wherein the cannulation extends through the end of the elongate structure.

9. The anti-skid surgical instrument of claim 1, comprising:
   a compliant part that absorbs energy from the mill head.

10. The anti-skid surgical instrument of claim 1,
    wherein a diameter of the guiding part is greater than a diameter of the shank.

11. The anti-skid surgical instrument of claim 1, wherein the one or more drill flutes comprise at least two, three, four, six, eight, ten, or twenty flutes.

12. The anti-skid surgical instrument of claim 1, wherein one or more side cutting flutes comprise at least two, three, four, six, eight, ten, or twenty flutes.

13. The anti-skid surgical instrument of claim 1, wherein a longitudinal length of the drilling portion is greater than a longitudinal length of the mill head.

14. The anti-skid surgical instrument of claim 1, wherein a longitudinal length of the drilling portion is greater than a longitudinal length of the shank.

15. The anti-skid surgical instrument of claim 1, wherein the one or more drill flutes have a higher twist rate than the one or more side cutting flutes or the one or more drill flutes have a lower twist rate than the one or more side cutting flutes.

16. The anti-skid surgical instrument of claim 1, wherein the one or more drill flutes have a different twist rate than the one or more side cutting flutes.

17. The anti-skid surgical instrument of claim 1, wherein the surgery is spinal, orthopedic, dental, ear, nose, or throat surgery.

* * * * *